US009897611B2

(12) United States Patent
Honda et al.

(10) Patent No.: US 9,897,611 B2
(45) Date of Patent: Feb. 20, 2018

(54) MOLECULE LIBRARY CONSTRUCTED ON THE BASIS OF BACKBONE STRUCTURE OF MICROPROTEIN

(71) Applicant: NATIONAL INSTITUTE OF ADVANCED INDUSTRIAL SCIENCE AND TECHNOLOGY, Tokyo (JP)

(72) Inventors: Shinya Honda, Ibaraki (JP); Hideki Watanabe, Ibaraki (JP); Kazuhiko Yamasaki, Ibaraki (JP)

(73) Assignee: NATIONAL INSTITUTE OF ADVANCED INDUSTRIAL SCIENCE AND TECHNOLOGY, Chiyoda-ku, Tokyo (JP)

( * ) Notice: Subject to any disclaimer, the term of this patent is extended or adjusted under 35 U.S.C. 154(b) by 223 days.

(21) Appl. No.: 14/655,792

(22) PCT Filed: Dec. 9, 2013

(86) PCT No.: PCT/JP2013/007238
§ 371 (c)(1),
(2) Date: Jun. 26, 2015

(87) PCT Pub. No.: WO2014/103203
PCT Pub. Date: Jul. 3, 2014

(65) Prior Publication Data
US 2015/0377899 A1 Dec. 31, 2015

(30) Foreign Application Priority Data
Dec. 27, 2012 (JP) ................................ 2012-285734

(51) Int. Cl.
| | |
|---|---|
| *C12N 7/06* | (2006.01) |
| *G01N 33/68* | (2006.01) |
| *C12N 15/10* | (2006.01) |
| *C07K 7/06* | (2006.01) |

(52) U.S. Cl.
CPC .......... *G01N 33/6845* (2013.01); *C07K 7/06* (2013.01); *C12N 15/1034* (2013.01); *C12N 15/1044* (2013.01); *C12N 15/1093* (2013.01); *C07K 2319/00* (2013.01)

(58) Field of Classification Search
None
See application file for complete search history.

(56) References Cited

U.S. PATENT DOCUMENTS

| | | |
|---|---|---|
| 2003/0166003 A1 | 9/2003 | Cochran et al. |
| 2010/0145008 A1 | 6/2010 | Pecorari et al. |
| 2011/0152500 A1* | 6/2011 | Jon .................... A61K 49/0032 530/350 |

FOREIGN PATENT DOCUMENTS

| | | |
|---|---|---|
| EP | 2 141 243 A2 | 1/2010 |
| JP | 2006-503088 A | 1/2006 |
| JP | 2009-112282 A | 5/2009 |
| JP | 2009-183292 A | 8/2009 |
| JP | 2010-511691 A | 4/2010 |
| WO | 95/19374 A1 | 7/1995 |
| WO | 00/63243 A1 | 10/2000 |

OTHER PUBLICATIONS

Zoller et al., "Miniproteins as Phage Display-Scaffolds for Clinical Applications", Molecules, 2011, vol. 16, pp. 2467-2485.
Mandal et al., "Chemical synthesis and X-ray structure of a heterochiral {D-protein antagonist plus vascular endothelial growth factor} protein complex by racemic crystallography", PNAS, 2012, vol. 109, No. 37, pp. 14779-14784.
Enemark et al., "Turn-directed folding dynamics of beta-hairpin-forming de novo decapeptide Chignolin", Phys. Chem. Chem. Phys., 2012, vol. 14, pp. 12442-12450.
Kuhrova et al., "Force-Field Dependence of Chignolin Folding and Misfolding: Comparison with Experiment and Redesign", Biophysical Journal, 2012, vol. 102, pp. 1897-1906.
Graeff et al., "MicroProtein-Mediated Recruitment of CONSTANS into a TOPLESS Trimeric Complex Represses Flowering in *Arabidopsis*", PLOS Genetics, 2016, pp. 1-22.
Watanabe et al., "Tracing Primordial Protein Evolution through Structurally Guided Stepwise Segment Elongation", The Journal of Biological Chemistry, 2014, vol. 289, No. 6, pp. 3394-3404.
Watanabe et al., "Adaptive Assembly: Maximizing the Potential of a Given Functional Peptide with a Tailor-Made Protein Scaffold", Chemistry & Biology, 2015, vol. 22, pp. 1165-1173.
Communication dated Aug. 30, 2016, issued by the European Patent Office in counterpart European application No. 13867307.4.
Daniel A. Bonsor, et al., "Dissecting Protein-Protein Interactions Using Directed Evolution", Biochemistry, 2011, pp. 2394-2402, vol. 50, No. 13.
H Kaspar Binz, et al., "Engineering novel binding proteins from nonimmunoglobulin domains", Nature Biotechnology, Oct. 2005, pp. 1257-1268, vol. 23, No. 10.
Ralf J. Hosse, et al., "A new generation of protein display scaffolds for molecular recognition", Protein Science, 2006, pp. 14-27, vol. 15.
Bjorn Nilsson, et al., "A synthetic IgG-binding domain based on staphylococcal protein A", Protein Engineering, 1987, pp. 107-113, vol. 1, No. 2.
Karin Nord, et al., "A combinatorial library of an a-helical bacterial receptor domain", Protein Engineering, 1995, pp. 601-608, vol. 8, No. 6.
Karin Nord, et al., "Binding proteins selected from combinatorial libraries of an α-helical bacterial receptor domain", Nature Biotechnology, Aug. 1997, pp. 772-777, vol. 15.

(Continued)

*Primary Examiner* — Christopher M Gross
(74) *Attorney, Agent, or Firm* — Sughrue Mion, PLLC

(57) ABSTRACT

Disclosed is a molecular library comprising a group of a plurality of molecules, wherein each member of the library is a polypeptide having a randomized sequence moiety and a microprotein moiety. The microprotein is a protein comprising an amino acid sequence of 30 or less amino acid residues having the ability to form a particular conformation by spontaneous folding in a solution and is, for example, chignolin comprising the amino acid sequence represented by SEQ ID NO: 1. Also, disclosed is a method for identifying a novel functional molecule using the library of the present invention.

10 Claims, 19 Drawing Sheets

(56) References Cited

OTHER PUBLICATIONS

Torun Engfeldt, et al., "Chemical Synthesis of Triple-Labelled Three-Helix Bundle Binding Proteins for Specific Fluorescent Detection of Unlabelled Protein", ChemBioChem, 2005, pp. 1043-1050, vol. 6.

Thuy Tran, et al., "(99m)Tc-maEEE-Z(HER2:342), an Affibody Molecule-Based Tracer for the Detection of HER2 Expression in Malignant Tumors", Bioconjugate Chem, 2007, pp. 1956-1964, vol. 18.

Akiko Koide, et al., "The Fibronectin Type III Domain as a Scaffold for Novel Binding Proteins", J Mol Biol., 1998, pp. 1141-1151, vol. 284.

Anna Tramontano, et al., "The Making of the Minibody: an Engineered β-protein for the Display of Conformationally Constrained Peptides", Journal of Molecular Recognition, 1994, pp. 9-24, vol. 7.

Elisabetta Bianchi, et al., "High Level Expression and Rational Mutagenesis of a Designed Protein, the Minibody, From an Insoluble to a Soluble Molecule", J Mol Biol, 1994, pp. 649-659, vol. 236.

Stephen J. McConnell, "Tendamistat as a Scaffold for Conformationally Constrained Phage Peptide Libraries", J Mol Biol, 1995, pp. 460-470, vol. 250.

Jung Ku, et al., "Alternate protein frameworks for molecular recognition", Proc Natl Acad Sci USA, Jul. 1995, pp. 6552-6556, vol. 92.

Jiang Qian, et al., "Protein Family and Fold Occurrence in Genomes: Power-law Behaviour and Evolutionary Model", J. Mol. Biol., 2001, pp. 673-681, vol. 313.

David G. Myszka, et al., "Design and Characterization of an Intramolecular Antiparallel Coiled Coil Peptide", Biochemistry, 1994, pp. 2363-2372, vol. 33.

H. Kaspar Binz, "Designing Repeat Proteins: Well-expressed, Soluble and Stable Proteins from Combinatorial Libraries of Consensus Ankyrin Repeat Proteins", J. Mol. Biol., 2003, pp. 489-503, vol. 332.

Joshua Silverman, et al., "Multivalent avimer proteins evolved by exon shuffling of a family of human receptor domains", Nature Biotechnology, Dec. 2005, pp. 1556-1561, vol. 23, No. 12.

Simon E. Hufton, et al., "Development and application of cytotoxic T lymphocyte-associated antigen 4 as a protein scaffold for the generation of novel binding ligands", FEBS Letters, 2000, pp. 225-231, vol. 475.

Aaron L. Nelson, et al., "Development trends for therapeutic antibody fragments", Nature Biotechnology, Apr. 2009, pp. 331-337, vol. 27, No. 4.

Achim Knappik, et al., "Fully Synthetic Human Combinatorial Antibody Libraries (HuCAL) Based on Modular Consensus Frameworks and CDRs Randomized with Trinucleotides", J. Mol. Biol., 2000, pp. 57-86, vol. 296.

Shinya Honda, et al., "10 Residue Folded Peptide Designed by Segment Statistics", Structure, Aug. 2004, pp. 1507-1518, vol. 12, No. 8.

Shinya Honda, et al., "Crystal Structure of a Ten-Amino Acid Protein", Journal of the American Chemical Society, 2008, pp. 15327-15331, vol. 130, No. 46.

Shinya Honda, "Discovery of chignolin, a "protein" consisting of only ten amino acids", Protein, Nucleic acid and Enzyme (PNE), 2005, pp. 427-433, vol. 50, No. 5.

Shinya Honda, "Minimal design of protein: Structure and fluctuation of super chignolin", Journal of the Biophysical Society of Japan, 2009, pp. 126-129, vol. 49, No. 3.

Zihao Cheng, et al., "An engineered tryptophan zipper-type peptide as a molecular recognition scaffold", Journal of Peptide Science, Aug. 15, 2009, pp. 523-532, vol. 15, No. 8.

Richard E. Herman, et al., "The Trp Cage Motif as a Scaffold for the Display of a Randomized Peptide Library on Bacteriophage T7", The Journal of Biological Chemistry, Mar. 30, 2007, pp. 9813-9824, vol. 282, No. 13.

Hideki Watanabe, et al., "Small artificial protein design using minute protein as components", Institute of Advanced Industrial Science and Technology, biomedical research division, May 31, 2013, 5 pages, 1P-128.

International Search Report for PCT/JP2013/07238 dated Jan. 14, 2014 [PCT/ISA/210].

\* cited by examiner (A)

(B)

SEQUENCE LISTING

```
<160> NUMBER OF SEQ ID NOS: 73

<210> SEQ ID NO 1
<211> LENGTH: 10
<212> TYPE: PRT
<213> ORGANISM: Artificial Sequence
<220> FEATURE:
```

```
<223> OTHER INFORMATION: chignolin

<400> SEQUENCE: 1

Gly Tyr Asp Pro Glu Thr Gly Thr Trp Gly
1               5                   10

<210> SEQ ID NO 2
<211> LENGTH: 10
<212> TYPE: PRT
<213> ORGANISM: Artificial Sequence
<220> FEATURE:
<223> OTHER INFORMATION: chignolin mutant
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 2

Xaa Tyr Asp Pro Xaa Thr Gly Thr Trp Xaa
1               5                   10

<210> SEQ ID NO 3
<211> LENGTH: 9
<212> TYPE: PRT
<213> ORGANISM: Artificial Sequence
<220> FEATURE:
<223> OTHER INFORMATION: chignolin mutant

<400> SEQUENCE: 3

Tyr Tyr Asp Pro Glu Thr Gly Thr Trp
1               5

<210> SEQ ID NO 4
<211> LENGTH: 9
<212> TYPE: PRT
<213> ORGANISM: Artificial Sequence
<220> FEATURE:
<223> OTHER INFORMATION: chignolin mutant

<400> SEQUENCE: 4

Tyr Asp Pro Glu Thr Gly Thr Trp Tyr
1               5

<210> SEQ ID NO 5
<211> LENGTH: 8
<212> TYPE: PRT
<213> ORGANISM: Artificial Sequence
<220> FEATURE:
<223> OTHER INFORMATION: chignolin mutant
<220> FEATURE:
<221> NAME/KEY: misc_feature
<222> LOCATION: (4)..(4)
<223> OTHER INFORMATION: Xaa can be any naturally occurring amino acid

<400> SEQUENCE: 5

Tyr Asp Pro Xaa Thr Gly Thr Trp
1               5

<210> SEQ ID NO 6
<211> LENGTH: 22
<212> TYPE: PRT
```

```
<213> ORGANISM: Artificial Sequence
<220> FEATURE:
<223> OTHER INFORMATION: chignolin library
<220> FEATURE:
<221> NAME/KEY: misc_feature
<222> LOCATION: (9)..(9)
<223> OTHER INFORMATION: Xaa can be any naturally occurring amino acid
<220> FEATURE:
<221> NAME/KEY: misc_feature
<222> LOCATION: (14)..(21)
<223> OTHER INFORMATION: Xaa can be any naturally occurring amino acid

<400> SEQUENCE: 6

Gly Gly Gly Gly Ser Tyr Asp Pro Xaa Thr Gly Thr Trp Xaa Xaa Xaa
1               5                   10                  15

Xaa Xaa Xaa Xaa Xaa Gly
            20

<210> SEQ ID NO 7
<211> LENGTH: 99
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (53)..(53)
<223> OTHER INFORMATION: k is g or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (56)..(56)
<223> OTHER INFORMATION: k is g or t
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (59)..(59)
<223> OTHER INFORMATION: k is g or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (62)..(62)
<223> OTHER INFORMATION: k is g or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (65)..(65)
<223> OTHER INFORMATION: k is g or t
<220> FEATURE:
<221> NAME/KEY: misc_feature
<222> LOCATION: (66)..(67)
<223> OTHER INFORMATION: n is a, c, g, or t
```

```
<220> FEATURE:
<221> NAME/KEY: misc_feature
<222> LOCATION: (68)..(68)
<223> OTHER INFORMATION: k is g or t
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (71)..(71)
<223> OTHER INFORMATION: k is g or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (74)..(74)
<223> OTHER INFORMATION: k is g or t

<400> SEQUENCE: 7
aagggaattc tggcggtggt ggcagctatg atccgnnkac cggcacctgg nnknnknnkn      60
nknnknnknn knnkggttaa tagaagcttc cgcgaggag                            99

<210> SEQ ID NO 8
<211> LENGTH: 17
<212> TYPE: PRT
<213> ORGANISM: Artificial Sequence
<220> FEATURE:
<223> OTHER INFORMATION: Selected sequence

<400> SEQUENCE: 8

Tyr Asp Pro Arg Thr Gly Thr Trp Arg Ser Ser Ile Ala Tyr Gly Gly
1               5                   10                  15

Gly

<210> SEQ ID NO 9
<211> LENGTH: 30
<212> TYPE: PRT
<213> ORGANISM: Artificial Sequence
<220> FEATURE:
<223> OTHER INFORMATION: chignolin library
<220> FEATURE:
<221> NAME/KEY: misc_feature
<222> LOCATION: (6)..(13)
<223> OTHER INFORMATION: Xaa can be any naturally occurring amino acid

<400> SEQUENCE: 9

Gly Gly Gly Gly Ser Xaa Xaa Xaa Xaa Xaa Xaa Xaa Xaa Tyr Asp Pro
1               5                   10                  15

Arg Thr Gly Thr Trp Arg Ser Ser Ile Ala Tyr Gly Gly Gly
            20                  25                  30

<210> SEQ ID NO 10
<211> LENGTH: 134
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
```

-continued

```
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t

<400> SEQUENCE: 10
gtgatgctcg gggatccgaa ttctggcggt ggtggcagcn nknnknnknn knnknnknnk      60
nnktatgatc cgcgtaccgg cacctggcgt tcttctattg cttatggtgg gggttaatag    120
aagcttccgc gagg                                                      134

<210> SEQ ID NO 11
<211> LENGTH: 87
<212> TYPE: DNA
<213> ORGANISM: Artificial Sequence
<220> FEATURE:
<223> OTHER INFORMATION: oligo DNA
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
```

<220> FEATURE:
<221> NAME/KEY: misc_feature
<222> LOCATION: (43)..(44)
<223> OTHER INFORMATION: n is a, c, g, or t
<220> FEATURE:
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t

<400> SEQUENCE: 11
gtgatgctcg gggatccgaa ttctggcggt ggtggcagcn nknnknnknn knnknnknnk    60
nnktatgatc cgcgtaccgg cacctgg                                       87

<210> SEQ ID NO 12
<211> LENGTH: 71
<212> TYPE: DNA
<213> ORGANISM: Artificial Sequence
<220> FEATURE:
<223> OTHER INFORMATION: oligo DNA

<400> SEQUENCE: 12
cctcgcggaa gcttctatta accccccacca taagcaatag aagaacgcca ggtgccggta    60
cgcggatcat a                                                        71

<210> SEQ ID NO 13
<211> LENGTH: 25

```
<212> TYPE: PRT
<213> ORGANISM: Artificial Sequence
<220> FEATURE:
<223> OTHER INFORMATION: Selected sequence, 2A1

<400> SEQUENCE: 13

Gly Val Val Arg Gln Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 14
<211> LENGTH: 25
<212> TYPE: PRT
<213> ORGANISM: Artificial Sequence
<220> FEATURE:
<223> OTHER INFORMATION: Control pepteide, 2A1Gly

<400> SEQUENCE: 14

Gly Val Val Arg Gln Trp Ser Gly Gly Gly Ser Gly Gly Gly
1               5                   10                  15

Arg Ser Ser Ile Ala Tyr Gly Gly Gly
            20                  25

<210> SEQ ID NO 15
<211> LENGTH: 37
<212> TYPE: PRT
<213> ORGANISM: Artificial Sequence
<220> FEATURE:
<223> OTHER INFORMATION: chignolin library
<220> FEATURE:
<221> NAME/KEY: misc_feature
<222> LOCATION: (28)..(37)
<223> OTHER INFORMATION: Xaa can be any naturally occurring amino acid

<400> SEQUENCE: 15

Gly Gly Gly Gly Ser Asp Ala Ala Trp His Leu Gly Glu Leu Val Trp
1               5                   10                  15

Ala Thr Tyr Tyr Asp Pro Glu Thr Gly Thr Trp Xaa Xaa Xaa Xaa Xaa
            20                  25                  30

Xaa Xaa Xaa Xaa Xaa
        35

<210> SEQ ID NO 16
<211> LENGTH: 159
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (106)..(107)
<223> OTHER INFORMATION: n is a, c, g, or t
<220> FEATURE:
<221> NAME/KEY: misc_feature
<222> LOCATION: (108)..(108)
<223> OTHER INFORMATION: k is g or t
<220> FEATURE:
<221> NAME/KEY: misc_feature
<222> LOCATION: (109)..(110)
<223> OTHER INFORMATION: n is a, c, g, or t
<220> FEATURE:
<221> NAME/KEY: misc_feature
<222> LOCATION: (111)..(111)
<223> OTHER INFORMATION: k is g or t
<220> FEATURE:
<221> NAME/KEY: misc_feature
<222> LOCATION: (112)..(113)
<223> OTHER INFORMATION: n is a, c, g, or t
```

```
<220> FEATURE:
<221> NAME/KEY: misc_feature
<222> LOCATION: (114)..(114)
<223> OTHER INFORMATION: k is g or t
<220> FEATURE:
<221> NAME/KEY: misc_feature
<222> LOCATION: (115)..(116)
<223> OTHER INFORMATION: n is a, c, g, or t
<220> FEATURE:
<221> NAME/KEY: misc_feature
<222> LOCATION: (117)..(117)
<223> OTHER INFORMATION: k is g or t
<220> FEATURE:
<221> NAME/KEY: misc_feature
<222> LOCATION: (118)..(119)
<223> OTHER INFORMATION: n is a, c, g, or t
<220> FEATURE:
<221> NAME/KEY: misc_feature
<222> LOCATION: (120)..(120)
<223> OTHER INFORMATION: k is g or t
<220> FEATURE:
<221> NAME/KEY: misc_feature
<222> LOCATION: (121)..(122)
<223> OTHER INFORMATION: n is a, c, g, or t
<220> FEATURE:
<221> NAME/KEY: misc_feature
<222> LOCATION: (123)..(123)
<223> OTHER INFORMATION: k is g or t
<220> FEATURE:
<221> NAME/KEY: misc_feature
<222> LOCATION: (124)..(125)
<223> OTHER INFORMATION: n is a, c, g, or t
<220> FEATURE:
<221> NAME/KEY: misc_feature
<222> LOCATION: (126)..(126)
<223> OTHER INFORMATION: k is g or t
<220> FEATURE:
<221> NAME/KEY: misc_feature
<222> LOCATION: (127)..(128)
<223> OTHER INFORMATION: n is a, c, g, or t
<220> FEATURE:
<221> NAME/KEY: misc_feature
<222> LOCATION: (129)..(129)
<223> OTHER INFORMATION: k is g or t
<220> FEATURE:
<221> NAME/KEY: misc_feature
<222> LOCATION: (130)..(131)
<223> OTHER INFORMATION: n is a, c, g, or t
<220> FEATURE:
<221> NAME/KEY: misc_feature
<222> LOCATION: (132)..(132)
<223> OTHER INFORMATION: k is g or t
<220> FEATURE:
<221> NAME/KEY: misc_feature
<222> LOCATION: (133)..(134)
<223> OTHER INFORMATION: n is a, c, g, or t
<220> FEATURE:
<221> NAME/KEY: misc_feature
<222> LOCATION: (135)..(135)
<223> OTHER INFORMATION: k is g or t

<400> SEQUENCE: 16
gtgatgctcg gggatccgaa ttcgggagga gggggatcag atgcagcgtg gcatctggga      60
gaactggtgt gggcaaccta ttatgatccg gaaaccggca cctggnnknn knnknnknnk    120
nnknnknnkn nknnktaata gaagcttccg cgaggtctg                           159

<210> SEQ ID NO 17
<211> LENGTH: 78
<212> TYPE: DNA
<213> ORGANISM: Artificial Sequence
<220> FEATURE:
<223> OTHER INFORMATION: oligo DNA

<400> SEQUENCE: 17
```
gtgatgctcg gggatccgaa ttcgggagga gggggatcag atgcagcgtg gcatctggga        60
gaactggtgt gggcaacc                                                      78

<210> SEQ ID NO 18
<211> LENGTH: 99
<212> TYPE: DNA
<213> ORGANISM: Artificial Sequence
<220> FEATURE:
<223> OTHER INFORMATION: oligo DNA
<220> FEATURE:
<221> NAME/KEY: misc_feature
<222> LOCATION: (25)..(25)
<223> OTHER INFORMATION: m is a or c
<220> FEATURE:
<221> NAME/KEY: misc_feature
<222> LOCATION: (26)..(27)
<223> OTHER INFORMATION: n is a, c, g, or t
<220> FEATURE:
<221> NAME/KEY: misc_feature
<222> LOCATION: (28)..(28)
<223> OTHER INFORMATION: m is a or c
<220> FEATURE:
<221> NAME/KEY: misc_feature
<222> LOCATION: (29)..(30)
<223> OTHER INFORMATION: n is a, c, g, or t
<220> FEATURE:
<221> NAME/KEY: misc_feature
<222> LOCATION: (31)..(31)
<223> OTHER INFORMATION: m is a or c
<220> FEATURE:
<221> NAME/KEY: misc_feature
<222> LOCATION: (32)..(33)
<223> OTHER INFORMATION: n is a, c, g, or t
<220> FEATURE:
<221> NAME/KEY: misc_feature
<222> LOCATION: (34)..(34)
<223> OTHER INFORMATION: m is a or c
<220> FEATURE:
<221> NAME/KEY: misc_feature
<222> LOCATION: (35)..(36)
<223> OTHER INFORMATION: n is a, c, g, or t
<220> FEATURE:
<221> NAME/KEY: misc_feature
<222> LOCATION: (37)..(37)
<223> OTHER INFORMATION: m is a or c
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (40)..(40)
<223> OTHER INFORMATION: m is a or c
<220> FEATURE:
<221> NAME/KEY: misc_feature
<222> LOCATION: (41)..(42)
<223> OTHER INFORMATION: n is a, c, g, or t
<220> FEATURE:
<221> NAME/KEY: misc_feature
<222> LOCATION: (43)..(43)
<223> OTHER INFORMATION: m is a or c
<220> FEATURE:
<221> NAME/KEY: misc_feature
<222> LOCATION: (44)..(45)
<223> OTHER INFORMATION: n is a, c, g, or t
<220> FEATURE:
<221> NAME/KEY: misc_feature
<222> LOCATION: (46)..(46)
<223> OTHER INFORMATION: m is a or c
<220> FEATURE:
<221> NAME/KEY: misc_feature
<222> LOCATION: (47)..(48)
<223> OTHER INFORMATION: n is a, c, g, or t
<220> FEATURE:
<221> NAME/KEY: misc_feature
<222> LOCATION: (49)..(49)
<223> OTHER INFORMATION: m is a or c -continued

```
<220> FEATURE:
<221> NAME/KEY: misc_feature
<222> LOCATION: (50)..(51)
<223> OTHER INFORMATION: n is a, c, g, or t
<220> FEATURE:
<221> NAME/KEY: misc_feature
<222> LOCATION: (52)..(52)
<223> OTHER INFORMATION: m is a or c
<220> FEATURE:
<221> NAME/KEY: misc_feature
<222> LOCATION: (53)..(54)
<223> OTHER INFORMATION: n is a, c, g, or t

<400> SEQUENCE: 18
cagacctcgc ggaagcttct attamnmmn mnmmnmnnm nmnnccaggt      60 gccggtttcc ggatcataat aggttgccca caccagttc                99

<210> SEQ ID NO 19
<211> LENGTH: 32
<212> TYPE: PRT
<213> ORGANISM: Artificial Sequence
<220> FEATURE:
<223> OTHER INFORMATION: Selected sequence

<400> SEQUENCE: 19

Asp Ala Ala Trp His Leu Gly Glu Leu Val Trp Ala Thr Tyr Tyr Asp
1               5                   10                  15

Pro Glu Thr Gly Thr Trp Ala Pro Asp Trp Arg Leu Met Gln Gly Gln
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: Selected sequence

<400> SEQUENCE: 20

Asp Ala Ala Trp His Leu Gly Glu Leu Val Trp Ala Thr Tyr Tyr Asp
1               5                   10                  15

Pro Glu Thr Gly Thr Trp Gln Pro Asp Trp Leu Tyr Met Thr Thr Arg
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: Selected sequence

<400> SEQUENCE: 21

Asp Ala Ala Trp His Leu Gly Glu Leu Val Trp Ala Thr Tyr Tyr Asp
1               5                   10                  15

Pro Glu Thr Gly Thr Trp Leu Pro Asp Trp Gln Thr Met Ala Gln Lys
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: Selected sequence, pep24

<400> SEQUENCE: 22

Asp Ala Ala Trp His Leu Gly Glu Leu Val Trp Ala Thr Tyr Tyr Asp
1               5                   10                  15
```

Pro Glu Thr Gly Thr Trp Glu Pro Asp Trp Gln Arg Met Leu Gly Gln
            20                  25                  30

<210> SEQ ID NO 23
<211> LENGTH: 56
<212> TYPE: PRT
<213> ORGANISM: Artificial Sequence
<220> FEATURE:
<223> OTHER INFORMATION: chignolin library
<220> FEATURE:
<221> NAME/KEY: misc_feature
<222> LOCATION: (6)..(15)
<223> OTHER INFORMATION: Xaa can be any naturally occurring amino acid

<400> SEQUENCE: 23

Gly Gly Gly Gly Ser Xaa Xaa Xaa Xaa Xaa Xaa Xaa Xaa Xaa Tyr
1               5                   10                  15

Asp Pro Glu Thr Gly Thr Trp Tyr Asp Ala Ala Trp His Leu Gly Glu
            20                  25                  30

Leu Val Trp Ala Thr Tyr Tyr Asp Pro Glu Thr Gly Thr Trp Ala Pro
        35                  40                  45

Asp Trp Arg Leu Met Gln Gly Gln
    50                  55

<210> SEQ ID NO 24
<211> LENGTH: 56
<212> TYPE: PRT
<213> ORGANISM: Artificial Sequence
<220> FEATURE:
<223> OTHER INFORMATION: chignolin library
<220> FEATURE:
<221> NAME/KEY: misc_feature
<222> LOCATION: (6)..(15)
<223> OTHER INFORMATION: Xaa can be any naturally occurring amino acid

<400> SEQUENCE: 24

Gly Gly Gly Gly Ser Xaa Xaa Xaa Xaa Xaa Xaa Xaa Xaa Xaa Tyr
1               5                   10                  15

Asp Pro Glu Thr Gly Thr Trp Tyr Asp Ala Ala Trp His Leu Gly Glu
            20                  25                  30

Leu Val Trp Ala Thr Tyr Tyr Asp Pro Glu Thr Gly Thr Trp Gln Pro
        35                  40                  45

Asp Trp Leu Tyr Met Thr Thr Arg
    50                  55

<210> SEQ ID NO 25
<211> LENGTH: 56
<212> TYPE: PRT
<213> ORGANISM: Artificial Sequence
<220> FEATURE:
<223> OTHER INFORMATION: chignolin library
<220> FEATURE:
<221> NAME/KEY: misc_feature
<222> LOCATION: (6)..(15)
<223> OTHER INFORMATION: Xaa can be any naturally occurring amino acid

<400> SEQUENCE: 25

Gly Gly Gly Gly Ser Xaa Xaa Xaa Xaa Xaa Xaa Xaa Xaa Xaa Tyr
1               5                   10                  15

Asp Pro Glu Thr Gly Thr Trp Tyr Asp Ala Ala Trp His Leu Gly Glu
            20                  25                  30

Leu Val Trp Ala Thr Tyr Tyr Asp Pro Glu Thr Gly Thr Trp Leu Pro
        35                  40                  45

Asp Trp Gln Thr Met Ala Gln Lys
    50                  55

<210> SEQ ID NO 26
<211> LENGTH: 56
<212> TYPE: PRT
<213> ORGANISM: Artificial Sequence
<220> FEATURE:
<223> OTHER INFORMATION: chignolin library
<220> FEATURE:
<221> NAME/KEY: misc_feature
<222> LOCATION: (6)..(15)
<223> OTHER INFORMATION: Xaa can be any naturally occurring amino acid

<400> SEQUENCE: 26

Gly Gly Gly Gly Ser Xaa Xaa Xaa Xaa Xaa Xaa Xaa Xaa Xaa Xaa Tyr
1               5                   10                  15

Asp Pro Glu Thr Gly Thr Trp Tyr Asp Ala Ala Trp His Leu Gly Glu
            20                  25                  30

Leu Val Trp Ala Thr Tyr Tyr Asp Pro Glu Thr Gly Thr Trp Glu Pro
        35                  40                  45

Asp Trp Gln Arg Met Leu Gly Gln
    50                  55

<210> SEQ ID NO 27
<211> LENGTH: 199
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (29)..(29)
<223> OTHER INFORMATION: k is g or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: k is g or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (41)..(41)
<223> OTHER INFORMATION: k is g or t
<220> FEATURE:
<221> NAME/KEY: misc_feature
<222> LOCATION: (42)..(43)

<223> OTHER INFORMATION: n is a, c, g, or t
<220> FEATURE:
<221> NAME/KEY: misc_feature
<222> LOCATION: (44)..(44)
<223> OTHER INFORMATION: k is g or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (47)..(47)
<223> OTHER INFORMATION: k is g or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (50)..(50)
<223> OTHER INFORMATION: k is g or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (53)..(53)
<223> OTHER INFORMATION: k is g or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (56)..(56)
<223> OTHER INFORMATION: k is g or t

<400> SEQUENCE: 27
aaaagaattc gggaggaggg ggatcannkn nknnknnknn knnknnknnk nnknnktacg    60
accccgagac gggcacgtgg tacgatgcag cgtggcatct gggagaactg gtgtgggcaa   120
cctattatga tccggaaacc gggacctggg ctcctgattg gcggcttatg cagggtcagt   180
agtagaagct tccgcgggg                                                199

<210> SEQ ID NO 28
<211> LENGTH: 199
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (29)..(29)
<223> OTHER INFORMATION: k is g or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: k is g or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (41)..(41)
<223> OTHER INFORMATION: k is g or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (44)..(44)
<223> OTHER INFORMATION: k is g or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (47)..(47)
<223> OTHER INFORMATION: k is g or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (50)..(50)
<223> OTHER INFORMATION: k is g or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (53)..(53)
<223> OTHER INFORMATION: k is g or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (56)..(56)
<223> OTHER INFORMATION: k is g or t

<400> SEQUENCE: 28
aaaagaattc gggaggaggg ggatcannkn nknnknnknn knnknnknnk nnknnktacg    60
accccgagac gggcacgtgg tacgatgcag cgtggcatct gggagaactg gtgtgggcaa   120
cctattatga tccggaaacc gggacctggc agccggattg gttgtatatg actactcggt   180
agtagaagct tccgcgggg                                                199

<210> SEQ ID NO 29
<211> LENGTH: 199
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (27)..(28)
<223> OTHER INFORMATION: n is a, c, g, or t
<220> FEATURE:

```
<221> NAME/KEY: misc_feature
<222> LOCATION: (29)..(29)
<223> OTHER INFORMATION: k is g or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: k is g or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (41)..(41)
<223> OTHER INFORMATION: k is g or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (44)..(44)
<223> OTHER INFORMATION: k is g or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (47)..(47)
<223> OTHER INFORMATION: k is g or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (50)..(50)
<223> OTHER INFORMATION: k is g or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (53)..(53)
<223> OTHER INFORMATION: k is g or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (56)..(56)
<223> OTHER INFORMATION: k is g or t

<400> SEQUENCE: 29
aaaagaattc gggaggaggg ggatcannkn nknnknnknn knnknnknnk nnknnktacg      60
```
accccgagac gggcacgtgg tacgatgcag cgtggcatct gggagaactg gtgtgggcaa    120
cctattatga tccggaaacc gggacctggc ttcctgattg cagacgatg gcgcagaagt    180 agtagaagct tccgcgggg                                                 199

```
<210> SEQ ID NO 30
<211> LENGTH: 199
<212> TYPE: DNA
<213> ORGANISM: Artificial Sequence
<220> FEATURE:
<223> OTHER INFORMATION: chignolin library gene
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (29)..(29)
<223> OTHER INFORMATION: k is g or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: k is g or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (41)..(41)
<223> OTHER INFORMATION: k is g or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature
<222> LOCATION: (44)..(44)
<223> OTHER INFORMATION: k is g or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (47)..(47)
<223> OTHER INFORMATION: k is g or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (50)..(50)
<223> OTHER INFORMATION: k is g or t
<220> FEATURE:
```

<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (53)..(53)
<223> OTHER INFORMATION: k is g or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (56)..(56)
<223> OTHER INFORMATION: k is g or t

<400> SEQUENCE: 30
aaaagaattc gggaggaggg ggatcannkn nknnknnknn knnknnknnk nnknnktacg    60
accccgagac gggcacgtgg tacgatgcag cgtggcatct gggagaactg gtgtgggcaa   120
cctattatga tccggaaacc gggacctggg agcctgattg gcagaggatg ctggggcagt   180
agtagaagct tccgcgggg                                                199

<210> SEQ ID NO 31
<211> LENGTH: 99
<212> TYPE: DNA
<213> ORGANISM: Artificial Sequence
<220> FEATURE:
<223> OTHER INFORMATION: oligo DNA
<220> FEATURE:
<221> NAME/KEY: misc_feature
<222> LOCATION: (27)..(28)
<223> OTHER INFORMATION: n is a, c, g, or t
<220> FEATURE:
<221> NAME/KEY: misc_feature
<222> LOCATION: (29)..(29)
<223> OTHER INFORMATION: k is g or t
<220> FEATURE:
<221> NAME/KEY: misc_feature
<222> LOCATION: (30)..(31)
<223> OTHER INFORMATION: n is a, c, g, or t
<220> FEATURE:
<221> NAME/KEY: misc_feature
<222> LOCATION: (32)..(32)
<223> OTHER INFORMATION: k is g or t
<220> FEATURE:
<221> NAME/KEY: misc_feature
<222> LOCATION: (33)..(34)
<223> OTHER INFORMATION: n is a, c, g, or t
<220> FEATURE:
<221> NAME/KEY: misc_feature
<222> LOCATION: (35)..(35)
<223> OTHER INFORMATION: k is g or t
<220> FEATURE:
<221> NAME/KEY: misc_feature
<222> LOCATION: (36)..(37)
<223> OTHER INFORMATION: n is a, c, g, or t
<220> FEATURE:
<221> NAME/KEY: misc_feature
<222> LOCATION: (38)..(38)
<223> OTHER INFORMATION: k is g or t
<220> FEATURE:
<221> NAME/KEY: misc_feature
<222> LOCATION: (39)..(40)
<223> OTHER INFORMATION: n is a, c, g, or t
<220> FEATURE:
<221> NAME/KEY: misc_feature
<222> LOCATION: (41)..(41)
<223> OTHER INFORMATION: k is g or t
<220> FEATURE:
<221> NAME/KEY: misc_feature
<222> LOCATION: (42)..(43)
<223> OTHER INFORMATION: n is a, c, g, or t
<220> FEATURE:
<221> NAME/KEY: misc_feature

```
<222> LOCATION: (44)..(44)
<223> OTHER INFORMATION: k is g or t
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (47)..(47)
<223> OTHER INFORMATION: k is g or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (50)..(50)
<223> OTHER INFORMATION: k is g or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (53)..(53)
<223> OTHER INFORMATION: k is g or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (56)..(56)
<223> OTHER INFORMATION: k is g or t

<400> SEQUENCE: 31
aaaagaattc gggaggaggg ggatcannkn nknnknnknn knnknnknnk nnknnktacg     60
accccgagac gggcacgtgg tacgatgcag cgtggcatc                            99

<210> SEQ ID NO 32
<211> LENGTH: 49
<212> TYPE: DNA
<213> ORGANISM: Artificial Sequence
<220> FEATURE:
<223> OTHER INFORMATION: oligo DNA

<400> SEQUENCE: 32
ataggttgcc cacaccagtt ctcccagatg ccacgctgca tcgtaccac                 49

<210> SEQ ID NO 33
<211> LENGTH: 99
<212> TYPE: DNA
<213> ORGANISM: Artificial Sequence
<220> FEATURE:
<223> OTHER INFORMATION: oligo DNA

<400> SEQUENCE: 33
gggagaactg gtgtgggcaa cctattatga tccggaaacc gggacctggg ctcctgattg     60
gcggcttatg cagggtcagt agtagaagct tccgcgggg                            99

<210> SEQ ID NO 34
<211> LENGTH: 99
<212> TYPE: DNA
<213> ORGANISM: Artificial Sequence
<220> FEATURE:
<223> OTHER INFORMATION: oligo DNA

<400> SEQUENCE: 34
gggagaactg gtgtgggcaa cctattatga tccggaaacc gggacctggc agccggattg     60
```
gttgtatatg actactcggt agtagaagct ccgcgggg                                    99

<210> SEQ ID NO 35
<211> LENGTH: 99
<212> TYPE: DNA
<213> ORGANISM: Artificial Sequence
<220> FEATURE:
<223> OTHER INFORMATION: oligo DNA

<400> SEQUENCE: 35
gggagaactg gtgtgggcaa cctattatga tccggaaacc gggacctggc ttcctgattg      60
gcagacgatg gcgcagaagt agtagaagct ccgcgggg                              99

<210> SEQ ID NO 36
<211> LENGTH: 99
<212> TYPE: DNA
<213> ORGANISM: Artificial Sequence
<220> FEATURE:
<223> OTHER INFORMATION: oligo DNA

<400> SEQUENCE: 36
gggagaactg gtgtgggcaa cctattatga tccggaaacc gggacctggg agcctgattg      60
gcagaggatg ctggggcagt agtagaagct ccgcgggg                              99

<210> SEQ ID NO 37
<211> LENGTH: 51
<212> TYPE: PRT
<213> ORGANISM: Artificial Sequence
<220> FEATURE:
<223> OTHER INFORMATION: Selected sequence

<400> SEQUENCE: 37

Ser Asn Phe Val Arg Ser Pro Ser Ala Trp Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 38
<211> LENGTH: 51
<212> TYPE: PRT
<213> ORGANISM: Artificial Sequence
<220> FEATURE:
<223> OTHER INFORMATION: Selected sequence

<400> SEQUENCE: 38

Gly Pro Tyr Asn Ile Pro Asp Ser Ala Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 39
<211> LENGTH: 51
<212> TYPE: PRT
<213> ORGANISM: Artificial Sequence -continued

```
<220> FEATURE:
<223> OTHER INFORMATION: Selected sequence

<400> SEQUENCE: 39

Val Pro Pro Arg Phe Ser Ser Ala Gln Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 40
<211> LENGTH: 51
<212> TYPE: PRT
<213> ORGANISM: Artificial Sequence
<220> FEATURE:
<223> OTHER INFORMATION: Selected sequence, p17

<400> SEQUENCE: 40

Ile Ser Ala Phe Ser Pro Gly Arg Gly Val Tyr Asp Pro Glu Thr Gly
1               5                   10                  15

Thr Trp Tyr Asp Ala Ala Trp His Leu Gly Glu Leu Val Trp Ala Thr
            20                  25                  30

Tyr Tyr Asp Pro Glu Thr Gly Thr Trp Glu Pro Asp Trp Gln Arg Met
        35                  40                  45

Leu Gly Gln
    50

<210> SEQ ID NO 41
<211> LENGTH: 216
<212> TYPE: PRT
<213> ORGANISM: Artificial Sequence
<220> FEATURE:
<223> OTHER INFORMATION: Selected sequence

<400> SEQUENCE: 41

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
        130                 135                 140

Ala Leu Glu Val Leu Phe Gln Gly Pro Gly Tyr Gln Asp Pro Asn Ser
145                 150                 155                 160
```

```
Gly Gly Gly Gly Ser Ser Asn Phe Val Arg Ser Pro Ser Ala Trp Tyr
            165                 170                 175

Asp Pro Glu Thr Gly Thr Trp Tyr Asp Ala Ala Trp His Leu Gly Glu
        180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 42
<211> LENGTH: 216
<212> TYPE: PRT
<213> ORGANISM: Artificial Sequence
<220> FEATURE:
<223> OTHER INFORMATION: Selected sequence

<400> SEQUENCE: 42

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
 50                 55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
        115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Gly Pro Tyr Asn Ile Pro Asp Ser Ala Val Tyr
            165                 170                 175

Asp Pro Glu Thr Gly Thr Trp Tyr Asp Ala Ala Trp His Leu Gly Glu
        180                 185                 190

Leu Val Trp Ala Thr Tyr Tyr Asp Pro Glu Thr Gly Thr Trp Glu Pro
        195                 200                 205

Asp Trp Gln Arg Met Leu Gly Gln
    210                 215

<210> SEQ ID NO 43
<211> LENGTH: 216
<212> TYPE: PRT
<213> ORGANISM: Artificial Sequence
<220> FEATURE:
<223> OTHER INFORMATION: Selected sequence

<400> SEQUENCE: 43

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30
```

```
Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Val Pro Pro Arg Phe Ser Ser Ala Gln Tyr
                165                 170                 175

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
210                 215

<210> SEQ ID NO 44
<211> LENGTH: 216
<212> TYPE: PRT
<213> ORGANISM: Artificial Sequence
<220> FEATURE:
<223> OTHER INFORMATION: Selected sequence

<400> SEQUENCE: 44

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Asn Pro Pro Thr
            115                 120                 125

Pro Thr Pro Ser Ser Gly Ser Gly His His His His His His Ser Ala
130                 135                 140

Ala Leu Glu Val Leu Phe Gln Gly Pro Gly Tyr Gln Asp Pro Asn Ser
145                 150                 155                 160

Gly Gly Gly Gly Ser Ile Ser Ala Phe Ser Pro Gly Arg Gly Val Tyr
                165                 170                 175
```

Asp Pro Glu Thr Gly Thr Trp Tyr Asp Ala Ala Trp His Leu Gly Glu
            180                 185                 190

Leu Val Trp Ala Thr Tyr Tyr Asp Pro Glu Thr Gly Thr Trp Glu Pro
            195                 200                 205

Asp Trp Gln Arg Met Leu Gly Gln
        210                 215

<210> SEQ ID NO 45
<211> LENGTH: 205
<212> TYPE: PRT
<213> ORGANISM: Artificial Sequence
<220> FEATURE:
<223> OTHER INFORMATION: Selected sequence

<400> SEQUENCE: 45

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Thr Ser Gly Gly Gly Ser Asn Asn Pro Pro Thr
        115                 120                 125

Pro Thr Pro Ser Ser Gly Ser Gly His His His His His Ser Ala
    130                 135                 140

Ala Leu Glu Val Leu Phe Gln Gly Pro Gly Ile Ser Ala Phe Ser Pro
145                 150                 155                 160

Gly Arg Gly Val Tyr Asp Pro Glu Thr Gly Thr Trp Tyr Asp Ala Ala
                165                 170                 175

Trp His Leu Gly Glu Leu Val Trp Ala Thr Tyr Tyr Asp Pro Glu Thr
            180                 185                 190

Gly Thr Trp Glu Pro Asp Trp Gln Arg Met Leu Gly Gln
        195                 200                 205

<210> SEQ ID NO 46
<211> LENGTH: 618
<212> TYPE: DNA
<213> ORGANISM: Artificial Sequence
<220> FEATURE:
<223> OTHER INFORMATION: oligo DNA

<400> SEQUENCE: 46
atgagcgata aaattattca cctgactgac gacagttttg acacggatgt actcaaagcg      60 gacgggcga tcctcgtcga tttctgggca gagtggtgcg gtccgtgcaa aatgatcgcc     120
ccgattctgg atgaaatcgc tgacgaatat cagggcaaac tgaccgttgc aaaactgaac     180
atcgatcaaa accctggcac tgcgccgaaa tatggcatcc gtggtatccc gactctgctg     240
ctgttcaaaa acggtgaagt ggcggcaacc aaagtgggtg cactgtctaa aggtcagttg     300

```
aaagagttcc tcgacgctaa cctggccggt tctggttctg gccatactag tggtggtggc    360
ggttctaata acaatcctcc tactcctact ccatctagtg gttctggtca tcaccatcac    420
catcactccg cggctcttga agtcctcttt cagggacccg gcattagtgc gttttctccg    480
gggcgtgggg tgtacgaccc cgagacgggc acgtggtacg atgcagcgtg gcatctggga    540
gaactggtgt gggcaaccta ttatgatccg gaaaccggga cctgggagcc tgattggcag    600
aggatgctgg ggcagtag                                                  618
```

```
<210> SEQ ID NO 47
<211> LENGTH: 54
<212> TYPE: PRT
<213> ORGANISM: Artificial Sequence
<220> FEATURE:
<223> OTHER INFORMATION: Selected sequence, p17_2

<400> SEQUENCE: 47

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Trp
        35                  40                  45

Gln Arg Met Leu Gly Gln
    50

<210> SEQ ID NO 48
<211> LENGTH: 20
<212> TYPE: PRT
<213> ORGANISM: Artificial Sequence
<220> FEATURE:
<223> OTHER INFORMATION: Trp-cage protein

<400> SEQUENCE: 48

Asn Leu Tyr Ile Gln Trp Leu Lys Asp Gly Gly Pro Ser Ser Gly Arg
1               5                   10                  15

Pro Pro Pro Ser
            20

<210> SEQ ID NO 49
<211> LENGTH: 28
<212> TYPE: PRT
<213> ORGANISM: Artificial Sequence
<220> FEATURE:
<223> OTHER INFORMATION: FSD-1

<400> SEQUENCE: 49

Glu Gln Tyr Thr Ala Lys Tyr Lys Gly Arg Thr Phe Arg Asn Glu Lys
1               5                   10                  15

Glu Leu Arg Asp Phe Ile Glu Lys Phe Lys Gly Arg
            20                  25

<210> SEQ ID NO 50
<211> LENGTH: 18
<212> TYPE: PRT
<213> ORGANISM: Artificial Sequence
<220> FEATURE:
<223> OTHER INFORMATION: lanthanide-binding peptide
<220> FEATURE:
<221> NAME/KEY: MISC_FEATURE
<222> LOCATION: (18)..(18)
<223> OTHER INFORMATION: Xaa can be any naturally occurring amino acid

<400> SEQUENCE: 50
```

Tyr Ile Asp Thr Asn Asn Asp Gly Trp Tyr Glu Gly Asp Glu Leu Leu
1               5                   10                  15

Ala Xaa

<210> SEQ ID NO 51
<211> LENGTH: 25
<212> TYPE: PRT
<213> ORGANISM: Artificial Sequence
<220> FEATURE:
<223> OTHER INFORMATION: Selected sequence, 2A1_Q5R

<400> SEQUENCE: 51

Gly Val Val Arg Arg Trp Ser Gly Tyr Asp Pro Arg Thr Gly Thr Trp
1               5                   10                  15

Arg Ser Ser Ile Ala Tyr Gly Gly Gly
            20                  25

<210> SEQ ID NO 52
<211> LENGTH: 25
<212> TYPE: PRT
<213> ORGANISM: Artificial Sequence
<220> FEATURE:
<223> OTHER INFORMATION: Selected sequence, 2A1_W6A

<400> SEQUENCE: 52

Gly Val Val Arg Gln Ala Ser Gly Tyr Asp Pro Arg Thr Gly Thr Trp
1               5                   10                  15

Arg Ser Ser Ile Ala Tyr Gly Gly Gly
            20                  25

<210> SEQ ID NO 53
<211> LENGTH: 25
<212> TYPE: PRT
<213> ORGANISM: Artificial Sequence
<220> FEATURE:
<223> OTHER INFORMATION: Selected sequence, 2A1_S7A

<400> SEQUENCE: 53

Gly Val Val Arg Gln Trp Ala Gly Tyr Asp Pro Arg Thr Gly Thr Trp
1               5                   10                  15

Arg Ser Ser Ile Ala Tyr Gly Gly Gly
            20                  25

<210> SEQ ID NO 54
<211> LENGTH: 25
<212> TYPE: PRT
<213> ORGANISM: Artificial Sequence
<220> FEATURE:
<223> OTHER INFORMATION: Selected sequence, 2A1_R17A

<400> SEQUENCE: 54

Gly Val Val Arg Gln Trp Ser Gly Tyr Asp Pro Arg Thr Gly Thr Trp
1               5                   10                  15

Ala Ser Ser Ile Ala Tyr Gly Gly Gly
            20                  25

<210> SEQ ID NO 55
<211> LENGTH: 25
<212> TYPE: PRT
<213> ORGANISM: Artificial Sequence
<220> FEATURE:
<223> OTHER INFORMATION: Selected sequence, 2A1_S18A

<400> SEQUENCE: 55

Gly Val Val Arg Gln Trp Ser Gly Tyr Asp Pro Arg Thr Gly Thr Trp
1               5                   10                  15

Arg Ala Ser Ile Ala Tyr Gly Gly Gly
            20                  25

<210> SEQ ID NO 56
<211> LENGTH: 25
<212> TYPE: PRT
<213> ORGANISM: Artificial Sequence
<220> FEATURE:
<223> OTHER INFORMATION: Selected sequence, 2A1_S19A

<400> SEQUENCE: 56

Gly Val Val Arg Gln Trp Ser Gly Tyr Asp Pro Arg Thr Gly Thr Trp
1               5                   10                  15

Arg Ser Ala Ile Ala Tyr Gly Gly Gly
            20                  25

<210> SEQ ID NO 57
<211> LENGTH: 25
<212> TYPE: PRT
<213> ORGANISM: Artificial Sequence
<220> FEATURE:
<223> OTHER INFORMATION: Selected sequence, 2A1_I20A

<400> SEQUENCE: 57

Gly Val Val Arg Gln Trp Ser Gly Tyr Asp Pro Arg Thr Gly Thr Trp
1               5                   10                  15

Arg Ser Ser Ala Ala Tyr Gly Gly Gly
            20                  25

<210> SEQ ID NO 58
<211> LENGTH: 30
<212> TYPE: PRT
<213> ORGANISM: Artificial Sequence
<220> FEATURE:
<223> OTHER INFORMATION: gliycine library
<220> FEATURE:
<221> NAME/KEY: misc_feature
<222> LOCATION: (6)..(13)
<223> OTHER INFORMATION: Xaa can be any naturally occurring amino acid

<400> SEQUENCE: 58

Gly Gly Gly Gly Ser Xaa Xaa Xaa Xaa Xaa Xaa Xaa Xaa Gly Gly Gly
1               5                   10                  15

Ser Gly Gly Gly Gly Arg Ser Ser Ile Ala Tyr Gly Gly Gly
            20                  25                  30

<210> SEQ ID NO 59
<211> LENGTH: 134
<212> TYPE: DNA
<213> ORGANISM: Artificial Sequence
<220> FEATURE:
<223> OTHER INFORMATION: glycine library gene
<220> FEATURE:
<221> NAME/KEY: misc_feature
<222> LOCATION: (40)..(41)
<223> OTHER INFORMATION: n is a, c, g, or t
<220> FEATURE:
<221> NAME/KEY: misc_feature
<222> LOCATION: (42)..(42)
<223> OTHER INFORMATION: k is g or t
<220> FEATURE:
<221> NAME/KEY: misc_feature
<222> LOCATION: (43)..(44)
<223> OTHER INFORMATION: n is a, c, g, or t
<220> FEATURE:

```
<221> NAME/KEY: misc_feature
<222> LOCATION: (45)..(45)
<223> OTHER INFORMATION: k is g or t
<220> FEATURE:
<221> NAME/KEY: misc_feature
<222> LOCATION: (46)..(47)
<223> OTHER INFORMATION: n is a, c, g, or t
<220> FEATURE:
<221> NAME/KEY: misc_feature
<222> LOCATION: (48)..(48)
<223> OTHER INFORMATION: k is g or t
<220> FEATURE:
<221> NAME/KEY: misc_feature
<222> LOCATION: (49)..(50)
<223> OTHER INFORMATION: n is a, c, g, or t
<220> FEATURE:
<221> NAME/KEY: misc_feature
<222> LOCATION: (51)..(51)
<223> OTHER INFORMATION: k is g or t
<220> FEATURE:
<221> NAME/KEY: misc_feature
<222> LOCATION: (52)..(53)
<223> OTHER INFORMATION: n is a, c, g, or t
<220> FEATURE:
<221> NAME/KEY: misc_feature
<222> LOCATION: (54)..(54)
<223> OTHER INFORMATION: k is g or t
<220> FEATURE:
<221> NAME/KEY: misc_feature
<222> LOCATION: (55)..(56)
<223> OTHER INFORMATION: n is a, c, g, or t
<220> FEATURE:
<221> NAME/KEY: misc_feature
<222> LOCATION: (57)..(57)
<223> OTHER INFORMATION: k is g or t
<220> FEATURE:
<221> NAME/KEY: misc_feature
<222> LOCATION: (58)..(59)
<223> OTHER INFORMATION: n is a, c, g, or t
<220> FEATURE:
<221> NAME/KEY: misc_feature
<222> LOCATION: (60)..(60)
<223> OTHER INFORMATION: k is g or t
<220> FEATURE:
<221> NAME/KEY: misc_feature
<222> LOCATION: (61)..(62)
<223> OTHER INFORMATION: n is a, c, g, or t
<220> FEATURE:
<221> NAME/KEY: misc_feature
<222> LOCATION: (63)..(63)
<223> OTHER INFORMATION: k is g or t

<400> SEQUENCE: 59
gtgatgctcg gggatccgaa ttctggcggt ggtggcagcn nknnknnknn knnknnknnk      60
nnkggagggg gaagtggggg cggagggcgt tcttctattg cttatggtgg gggttaatag     120
aagcttccgc gagg                                                       134

<210> SEQ ID NO 60
<211> LENGTH: 54
<212> TYPE: PRT
<213> ORGANISM: Artificial Sequence
<220> FEATURE:
<223> OTHER INFORMATION: Selected sequence, p17_P46A

<400> SEQUENCE: 60

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Ala Asp Trp
        35                  40                  45
```

Gln Arg Met Leu Gly Gln
    50

<210> SEQ ID NO 61
<211> LENGTH: 54
<212> TYPE: PRT
<213> ORGANISM: Artificial Sequence
<220> FEATURE:
<223> OTHER INFORMATION: Selected sequence, p17_D47A

<400> SEQUENCE: 61

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Ala Trp
        35                  40                  45

Gln Arg Met Leu Gly Gln
    50

<210> SEQ ID NO 62
<211> LENGTH: 54
<212> TYPE: PRT
<213> ORGANISM: Artificial Sequence
<220> FEATURE:
<223> OTHER INFORMATION: Selected sequence, p17_W48A

<400> SEQUENCE: 62

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Ala
        35                  40                  45

Gln Arg Met Leu Gly Gln
    50

<210> SEQ ID NO 63
<211> LENGTH: 54
<212> TYPE: PRT
<213> ORGANISM: Artificial Sequence
<220> FEATURE:
<223> OTHER INFORMATION: Selected sequence, p17_R50A

<400> SEQUENCE: 63

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Trp
        35                  40                  45

Gln Ala Met Leu Gly Gln
    50

<210> SEQ ID NO 64
<211> LENGTH: 54
<212> TYPE: PRT
<213> ORGANISM: Artificial Sequence
<220> FEATURE:
<223> OTHER INFORMATION: Selected sequence, p17_M51A

<400> SEQUENCE: 64

Gly Pro Gly Ile Ser Ala Phe Ser Pro Gly Arg Gly Val Tyr Asp Pro
1               5                   10                  15

Glu Thr Gly Thr Trp Tyr Asp Ala Ala Trp His Leu Gly Glu Leu Val
            20                  25                  30

Trp Ala Thr Tyr Tyr Asp Pro Glu Thr Gly Thr Trp Glu Pro Asp Trp
        35                  40                  45

Gln Arg Ala Leu Gly Gln
        50

<210> SEQ ID NO 65
<211> LENGTH: 618
<212> TYPE: DNA
<213> ORGANISM: Artificial Sequence
<220> FEATURE:
<223> OTHER INFORMATION: oligo DNA

<400> SEQUENCE: 65

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggaggc tgattggcag   600
aggatgctgg ggcagtag                                                 618
```

<210> SEQ ID NO 66
<211> LENGTH: 618
<212> TYPE: DNA
<213> ORGANISM: Artificial Sequence
<220> FEATURE:
<223> OTHER INFORMATION: oligo DNA

<400> SEQUENCE: 66

```
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggagcc tgcttggcag   600
aggatgctgg ggcagtag                                                 618
```

<210> SEQ ID NO 67
<211> LENGTH: 618

```
<212> TYPE: DNA
<213> ORGANISM: Artificial Sequence
<220> FEATURE:
<223> OTHER INFORMATION: oligo DNA

<400> SEQUENCE: 67
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggagcc tgatgcgcag   600
aggatgctgg ggcagtag                                                  618

<210> SEQ ID NO 68
<211> LENGTH: 618
<212> TYPE: DNA
<213> ORGANISM: Artificial Sequence
<220> FEATURE:
<223> OTHER INFORMATION: oligo DNA

<400> SEQUENCE: 68
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
ctgttcaaaa acggtgaagt ggcggcaacc aaagtgggtg cactgtctaa aggtcagttg   300
aaagagttcc tcgacgctaa cctggccggt tctggttctg gccatactag tggtggtggc   360
ggttctaata acaatcctcc tactcctact ccatctagtg gttctggtca tcaccatcac   420
catcactccg cggctcttga agtcctcttt cagggacccg gcattagtgc gttttctccg   480
gggcgtgggg tgtacgaccc cgagacgggc acgtggtacg atgcagcgtg gcatctggga   540
gaactggtgt gggcaaccta ttatgatccg gaaaccggga cctgggagcc tgattggcag   600
gcgatgctgg ggcagtag                                                  618

<210> SEQ ID NO 69
<211> LENGTH: 618
<212> TYPE: DNA
<213> ORGANISM: Artificial Sequence
<220> FEATURE:
<223> OTHER INFORMATION: oligo DNA

<400> SEQUENCE: 69
atgagcgata aaattattca cctgactgac gacagttttg acacggatgt actcaaagcg    60
gacggggcga tcctcgtcga tttctgggca gagtggtgcg gtccgtgcaa aatgatcgcc   120
ccgattctgg atgaaatcgc tgacgaatat cagggcaaac tgaccgttgc aaaactgaac   180
atcgatcaaa accctggcac tgcgccgaaa tatggcatcc gtggtatccc gactctgctg   240
```

```
ctgttcaaaa acggtgaagt ggcggcaacc aaagtgggtg cactgtctaa aggtcagttg      300
aaagagttcc tcgacgctaa cctggccggt tctggttctg gccatactag tggtggtggc      360
ggttctaata acaatcctcc tactcctact ccatctagtg gttctggtca tcaccatcac      420
catcactccg cggctcttga agtcctcttt cagggacccg gcattagtgc gttttctccg      480
gggcgtgggg tgtacgaccc cgagacgggc acgtggtacg atgcagcgtg gcatctggga      540
gaactggtgt gggcaaccta ttatgatccg gaaaccggga cctgggagcc tgattggcag      600
agggcgctgg ggcagtag                                                    618
```

```
<210> SEQ ID NO 70
<211> LENGTH: 10
<212> TYPE: PRT
<213> ORGANISM: Artificial Sequence
<220> FEATURE:
<223> OTHER INFORMATION: chignolin
<220> FEATURE:
<221> NAME/KEY: MISC_FEATURE
<222> LOCATION: (1)..(1)
<223> OTHER INFORMATION: Xaa may be any amino acid and may be absent or
      repeated infinite number of times
<220> FEATURE:
<221> NAME/KEY: MISC_FEATURE
<222> LOCATION: (1)..(10)
<223> OTHER INFORMATION: amino acid residues may be repeated at least 2
      times
<220> FEATURE:
<221> NAME/KEY: MISC_FEATURE
<222> LOCATION: (5)..(5)
<223> OTHER INFORMATION: Xaa may be any amino acid
<220> FEATURE:
<221> NAME/KEY: MISC_FEATURE
<222> LOCATION: (10)..(10)
<223> OTHER INFORMATION: Xaa may be any amino acid and may be absent or
      repeated infinite number of times

<400> SEQUENCE: 70

Xaa Tyr Asp Pro Xaa Thr Gly Thr Trp Xaa
1               5                   10

<210> SEQ ID NO 71
<211> LENGTH: 8
<212> TYPE: PRT
<213> ORGANISM: Artificial Sequence
<220> FEATURE:
<223> OTHER INFORMATION: chignolin

<400> SEQUENCE: 71

Tyr Asp Pro Arg Thr Gly Thr Trp
1               5

<210> SEQ ID NO 72
<211> LENGTH: 8
<212> TYPE: PRT
<213> ORGANISM: Artificial Sequence
<220> FEATURE:
<223> OTHER INFORMATION: linker

<400> SEQUENCE: 72

Gly Gly Gly Ser Gly Gly Gly Gly
1               5

<210> SEQ ID NO 73
<211> LENGTH: 11
<212> TYPE: PRT
<213> ORGANISM: Artificial Sequence
<220> FEATURE:
<223> OTHER INFORMATION: chignolin
```

```
<400> SEQUENCE: 73

Tyr Gln Asp Pro Asn Ser Gly Gly Gly Ser
1               5                   10
```

MOLECULE LIBRARY CONSTRUCTED ON THE BASIS OF BACKBONE STRUCTURE OF MICROPROTEIN

CROSS REFERENCE TO RELATED APPLICATIONS

This application is a National Stage of International Application No. PCT/JP2013/007238, filed on Dec. 9, 2013, which claims priority from Japanese Patent Application No. 2012-285734, filed on Dec. 27, 2012, the contents of all of which are incorporated herein by reference in their entirety.

TECHNICAL FIELD

The present invention relates to a molecular library of polypeptides having the backbone structure of a microprotein, and a method for identifying a novel functional molecule using the library.

BACKGROUND ART

There exists a technological domain generally called evolutionary molecular engineering (or in vitro evolution) as methods for highly functionalizing biopolymers such as naturally occurring proteins or nucleic acids or methods for creating molecules having novel functions (Non Patent Literature 1). In recent years, the utilization of this technique has been expanded as basic technology for the development of biopharmaceutical products and diagnostic testing drugs.

For evolutionary molecular engineering targeting proteins and polypeptides, the constitution of an initial library is element technology crucial for success or failure of the creation of novel molecules (Non Patent Literatures 2 and 3). The forms of molecules constituting this initial library are broadly divided into two types. One of the two types is short-chain peptides of approximately 10 residues in length. In this case, almost the whole sequences of the molecules are randomized. Another type is relatively long-chain polypeptides with the backbone structure (fold) of a particular protein as a scaffold, and these molecules have a partially randomized sequence. Each of the short-chain peptide library and the protein backbone-type library has advantages and disadvantages as described below.

The short-chain peptide library is relatively easy to construct or screen. When peptides of 7 to 10 residues are randomized, the molecular diversity is theoretically on the scale of $20^7$ to $20^{10}$, i.e., $10^9$ to $10^{13}$ orders. Such a library size permits preparation and screening of the library using an existing technique. Various display techniques widely used in screening can also be easily applied to small molecular weights. On the other hand, the short-chain peptides are generally composed of highly flexible molecules and fail to stably form a particular three-dimensional structure in a solution. The short-chain peptides are therefore disadvantageous in that the specific binding between the peptide and a target receptor, the peptide and a target enzyme, etc., is low stable thermodynamically and high-affinity molecules or high-specificity molecules are difficult to obtain.

The protein backbone-type library employs the backbone structure of a particular natural protein (or artificial protein) as a scaffold. In many cases, the protein is selected from those having a known three-dimensional conformation. In the protein backbone-type library, not the whole molecule, but only a partial region is randomized. The other moieties maintain their particular sequences, which are often natural sequences. This is because the randomization of the whole region cannot be expected to form the inherent three-dimensional structure. For this purpose, an amino acid residue that contributes to the structure stabilization of the original protein is preserved with reference to conformation data or the like, while a loop region or the like positioned on the surface side of the molecule is often randomized. A plurality of loop regions may be randomized. In recent years, the backbone structure of an artificial protein consisting of an artificially designed sequence, rather than the natural protein, has sometimes been used as a scaffold.

The concept of the protein backbone-type library mimics the molecular structural patterns of antibodies (immunoglobulins). Specifically, the randomized moieties correspond to antibody variable regions, and the other moieties that maintain their natural sequences correspond to constant regions. As with antibodies, which recognize antigens via their variable regions, the protein backbone-type library is aimed at acquiring new functions via the randomized moieties.

Unlike the case of the short-chain peptide library, each randomized sequence introduced to the protein backbone is limited by possible conformations because both ends thereof are fixed to the robust backbone structure. The resulting library can be expected to circumvent the disadvantages attributed to the flexibility of the molecule. On the other hand, this library has no choice but to have a relatively enormous molecular size. In association with this, the degree of difficulty in research and development, production cost for practical use, reduced storage stability, etc., are pointed out as disadvantages. In addition, the limited conformations rather incur a potential risk for infeasible active structures.

Meanwhile, a molecular library based on a cyclic oligopeptide backbone is also known as a library of polypeptides having a small molecular weight and a stable structure. The cyclization of an oligopeptide, however, requires introduction of a functional group and complicated chemical reaction operation and complicates synthesis steps. Also, an oligopeptide cyclized through the oxidation reaction of cysteine is disadvantageous in that this oligopeptide is generally difficult to use in a reduced environment such as the inside of cells.

As mentioned above, the protein backbone-type library requires selecting a natural protein (or artificial protein) for use as a scaffold. Various proteins exceeding 40 types have been utilized so far (Non Patent Literatures 2 and 3). Table 1 shows main libraries, and some of them will be listed below as examples.

TABLE 1

Table 1. Features of main protein backbone-type libraries
(partial modification of excerpts from Non Patent Literature 2)

| Name of protein backbone | Size of whole molecule (the number of residues) | Size of randomized region (the number of residues) | Remarks |
|---|---|---|---|
| Immunoglobulin G | 1200 | 50-60 | Widely used as antibody drug |
| Antibody Fab fragment | 450 | 50-60 | |
| β-lactamase | 265 | 12 | |
| T-cell receptor | 250 | 5 (changeable) | |
| Green fluorescent protein | 238 | 18 | |
| Antibody Fv fragment | 200-250 | 50-60 | |
| Ankyrin repeat | 67 + 33n | 7n | |
| Carbohydrate-binding module (CBM4-2) | 168 | 12 | |
| Lipocalin | 160-180 | 16 | |
| Staphylococcal nuclease | 149 | 16 | |
| Ecotin | 142 | 20 | |
| Cytotoxic T-lymphocyte antigen 4 (CTLA-4) | 136 | 6 | |
| Thioredoxin | 108 | 20 | |
| Cytochrome b562 | 106 | 9 | |
| Src homology domain 2 (SH2) | 100 | 5 | |
| Fibronectin type 3 | 94 | 10 (changeable) | |
| Tendamistat | 74 | 6-8 | Having cyclic backbone |
| Minibody | 61 | 12 | |
| Src homology domain 3 (SH3) | 60 | 12 | |
| Affibody | 58 | 13 | Under development as pharmaceutical or diagnostic drug |
| Bovine pancreatic trypsin inhibitor | 58 | 5 | Having cyclic backbone |
| Lipoprotein-associated coagulation inhibitor | 58 | 9 | Having cyclic backbone |
| Human pancreatic secretory trypsin inhibitor | 56 | 8 | Having cyclic backbone |
| WW domain | 52 | 8 | |
| Phage envelope protein pVIII | 50 | 6 | |
| Human-derived trypsin inhibitor | 46 | 5 | Having cyclic backbone |
| A-domain | 35n-40n | 30n | Having cyclic backbone |
| Cellulose-binding domain | 36 | 11 | Having cyclic backbone |
| Insect-derived defensin A peptide | 29 | 7 | Having cyclic backbone |
| Gourd trypsin inhibitor II | 28 | 6 | Having cyclic backbone |
| Zinc finger | 26 | 5 | Having cyclic backbone |
| Scorpion toxin | 25-40 | 4 | Having cyclic backbone |
| Cyclized peptide backbone | 12 | 4 | Having cyclic backbone |

Affibody (Non Patent Literatures 4, 5, and 6 and Patent Literatures 1 and 2) having, as a protein backbone, protein Z modified from the antibody-binding domain of staphylococcal protein A (SPA) is a protein of 58 residues (6.5 kDa) that maintains high stability and solubility independently of intramolecular disulfide cross-link and permits large-scale production in a microbial expression system. In addition, its chemical production is also carried out by solid-phase synthesis (Non Patent Literature 7). A molecular library is prepared by rendering 13 residues on the helix variable. In this way, binding molecules have been obtained so far against dozens of types of target proteins. Affibody under most advanced research as a diagnostic reagent is high-affinity Affibody against a cell surface receptor HER-2, and this Affibody is applied as an imaging molecule for tumor diagnosis (Non Patent Literature 8).

Fibronectin type 3 domain is a small protein domain composed of β-sheet. Binding molecules against a plurality of targets such as ubiquitin have been obtained from a library in which the amino acid residues of two or three loop regions are randomized (Non Patent Literature 9 and Patent Literature 3).

Minibody is an artificial protein designed by the removal of three β-strands from the heavy chain variable domains of a monoclonal antibody (Non Patent Literature 10). This protein is 61 residues long and has two loops. These two loop regions are randomized. Although its low solubility (10 μM) has been perceived as a problem for practical use, variant-type Minibody that has attained high solubility (350 μM) as a result of mutagenesis has been reported (Non Patent Literature 11).

Tendamistat composed of 74 residues has six strands in β-sheet sandwich connected by two disulfide bonds (Non Patent Literature 12). This backbone contains three loops. Randomization has been attempted so far only for two of these loops.

Cytochrome b562 is a protein domain having a 4-helix bundle structure composed of 106 residues. A molecule binding with an equilibrium dissociation constant of 290 nM to low-molecular hapten has been obtained by the randomization of 9 amino acid residues in two loops (Non Patent Literature 13).

Oligonucleotide/oligosaccharide-binding fold (OB-fold) is a backbone structure constituted by five-stranded β-barrel capped by amphipathic α-helix (Patent Literature 4). The OB-fold is the 28th most common typical fold in the analysis of 20 or more genomic sequences (Non Patent Literature 14).

Cyclized β-turn peptide backbone is a low-molecular protein backbone having a stabilized conformation in a solution as a result of promoting the secondary structure formation of the peptide by disulfide-constrained cyclization (Patent Literature 5).

A protein backbone based on a coiled coil structure containing disulfide cross-link has been designed in order to stabilize the α-helix of a short-chain peptide. A coiled coil protein backbone containing an arginine-glycine-aspartic acid (RGD) sequence exhibits competitive inhibitory activity against fibrinogen (Non Patent Literature 15).

An artificial protein based on ankyrin repeat protein (designed AR protein, DARPin) is a giant protein having a repeat structure (Non Patent Literature 16). The repeat unit is a small domain of 33 residues and is composed of β-turn and antiparallel helix and loop without disulfide bonds.

A-domain (Non Patent Literature 17) is a backbone structure that is observed as a repeat unit. This structure is confirmed in cell surface receptors of various species and constituted by a linkage of domains each composed of 35 to 40 amino acid residues.

Cytotoxic T-lymphocyte antigen 4 (CTLA-4) is a helper T-cell surface receptor belonging to the immunoglobulin superfamily and acquires affinity for integrin by the introduction of a recognition sequence to hypervariable loop (Non Patent Literature 18).

Antibodies (immunoglobulins) are proteins that are used most widely as binding molecules having high specificity. Immunoglobulin G is a macromolecule having a molecular weight of approximately 150,000 and consisting of 12 subunits. An antigen-binding fragment (Fab) having a region containing an antigen-binding site by enzyme treatment, a variable region fragment (Fv) consisting of a heavy chain variable region (VH) and a light chain variable region (VL) prepared by a genetic engineering approach, a single-chain antibody (scFv) comprising VH and VL linked through a peptide linker, and the like are also frequently used as units of binding molecules (Non Patent Literature 19). A molecular library HuCAL has been reported in which the frameworks of an antibody variable region are used as a protein backbone of an artificial antibody independent of natural immune repertoire and complementarity-determining regions are randomized (Non Patent Literature 20).

CITATION LIST

Patent Literature

Patent Literature 1: International Publication No. WO/1995/019374
Patent Literature 2: International Publication No. WO/2000/063243
Patent Literature 3: Japanese Patent Laid-Open No. 2009-183292
Patent Literature 4: Japanese Patent Laid-Open No. 2010-511691
Patent Literature 5: National Publication of International Patent Application No. 2006-503088

Non Patent Literature

Non Patent Literature 1: Bonsor D A, Sundberg E J. (2011) Dissecting protein-protein interactions using directed evolution. Biochemistry. 50(13) 2394-402.
Non Patent Literature 2: Binz H K, Amstutz P, Pluckthun A. (2005) Engineering novel binding proteins from nonimmunoglobulin domains. Nat Biotechnol. 23, 1257-1268.
Non Patent Literature 3: Hosse R J, Rothe A and Power B E. (2006) A new generation of protein display scaffolds for molecular recognition. Protein Sci. 15, 14-27.
Non Patent Literature 4: Nilsson B, Moks T, Jansson B, Abrahmsen L, Elmblad A, Holmgren E, Henrichson C, Jones T A and Uhlen M. (1987) A synthetic IgG-binding domain based on staphylococcal protein A. Protein Eng. 1, 107-113.
Non Patent Literature 5: Nord K, Nilsson J, Nilsson B, Uhlen M and Nygren P A. (1995) A combinatorial library of an alpha-helical bacterial receptor domain. Protein Eng. 8, 601-608.
Non Patent Literature 6: Nord K, Gunneriusson E, Ringdahl J, Stahl S, Uhlen M and Nygren P A. (1997) Binding proteins selected from combinatorial libraries of an alpha-helical bacterial receptor domain. Nat Biotechnol. 15, 772-777.
Non Patent Literature 7: Engfeldt T, Renberg B, Brumer H, Nygren P A and Karlstrom A E. (2005) Chemical synthesis of triple-labelled three-helix bundle binding proteins for specific fluorescent detection of unlabelled protein. Chembiochem. 6(6) 1043-1050.
Non Patent Literature 8: Tran T, Engfeldt T, Orlova A, Sandstrom M, Feldwisch J, Abrahmsen L, Wennborg A, Tolmachev V and Karlstrom A E. (2007) (99m)Tc-maEEE-Z(HER2:342), an Affibody molecule-based tracer for the detection of HER2 expression in malignant tumors. Bioconjug Chem. 18(6) 1956-1964.
Non Patent Literature 9: Koide A, Bailey C W, Huang X and Koide S. (1998) The fibronectin type III domain as a scaffold for novel binding proteins. J Mol Biol. December 284, 1141-1151.
Non Patent Literature 10: Tramontano A, Bianchi E, Venturini S, Martin F, Pessi A and Sollazzo M. (1994) The making of the minibody: an engineered beta-protein for the display of conformationally constrained peptides. J Mol Recognit. 7, 9-24.
Non Patent Literature 11: Bianchi E, Venturini S, Pessi A, Tramontano A and Sollazzo M. (1994) High level expression and rational mutagenesis of a designed protein, the minibody. From an insoluble to a soluble molecule. J Mol Biol. 236(2) 649-659.
Non Patent Literature 12: McConnell S J and Hoess R H. (1995) Tendamistat as a scaffold for conformationally constrained phage peptide libraries. J Mol Biol. 250, 460-470.
Non Patent Literature 13: Ku J and Schultz P G. (1995) Alternate protein frameworks for molecular recognition. Proc Natl Acad Sci USA. 92, 6552-6556.
Non Patent Literature 14: Qian J, Luscombe N M and Gerstein M. (2001) Protein family and fold occurrence in genomes: power-law behaviour and evolutionary model. J Mol Biol. 313, 673-681.
Non Patent Literature 15: Myszka D G and Chaiken I M. (1994) Design and characterization of an intramolecular antiparallel coiled coil peptide. Biochemistry. 33, 2363-2372.
Non Patent Literature 16: 1Binz H K, Stumpp M T, Forrer P, Amstutz P and Pluckthun A. (2003) Designing repeat proteins: well-expressed, soluble and stable proteins from combinatorial libraries of consensus ankyrin repeat proteins. J Mol Biol. 332, 489-503.
Non Patent Literature 17: Silverman J, Liu Q, Bakker A, To W, Duguay A, Alba B M, Smith R, Rivas A, Li P, Le H, Whitehorn E, Moore K W, Swimmer C, Perlroth V, Vogt M, Kolkman J and Stemmer W P. (2005) Multivalent avimer proteins evolved by exon shuffling of a family of human receptor domains. Nat Biotechnol. 23, 1556-1561.

Non Patent Literature 18: Hufton S E, van Neer N, van den Beuken T, Desmet J, Sablon E and Hoogenboom H R. (2000) Development and application of cytotoxic T lymphocyte-associated antigen 4 as a protein scaffold for the generation of novel binding ligands. FEBS Lett. 475, 225-231.

Non Patent Literature 19: Nelson A L and Reichert J M. (2009) Development trends for therapeutic antibody fragments. Nat Biotechnol. 27(4) 331-337.

Non Patent Literature 20: Knappik A, Ge L, Honegger A, Pack P, Fischer M, Wellnhofer G, Hoess A, Wolle J, Pluckthun A and Virnekas B. (2000) Fully synthetic human combinatorial antibody libraries (HuCAL) based on modular consensus frameworks and CDRs randomized with trinucleotides. J Mol Biol. 296(1) 57-86.

Non Patent Literature 21: Honda, S. Yamasaki, Y. Sawada, and H. Morii (2004) 10-residue folded peptide designed by segment statistics Structure 12(8) 1507-1518.

Non Patent Literature 22: Honda, S., Akiba, T., Kato, Y. S., Sawada, Y., Sekijima, M., Ishimura, M., Ooishi, A., Watanabe, H., Odahara, T. and Harata, K. (2008) Crystal Structure of a Ten-Amino Acid Protein J. Am. Chem. Soc., 130(46), 15327-15331.

Non Patent Literature 23: Shinya Honda ""Protein" of 10 amino acids, discovery of chignolin", Protein, Nucleic acid and Enzyme (PNE), 50 (5), 427-433 (2005).

Non Patent Literature 24: Shinya Honda "Minimal Design of Protein: Structure and wobbling of super chignolin", Journal of the Biophysical Society of Japan, 49 (3), 126-129 (2009).

SUMMARY OF INVENTION

Technical Problem

An object of the present invention is to provide a molecular library of molecules having a small molecular weight and a stable structure, and a method for identifying a novel molecule by use of the library.

Solution to Problem

The present inventors have conducted diligent studies to attain the object and consequently successfully developed a molecular library of polypeptides having a small molecular weight and a stable conformation by use of the backbone structure of a microprotein such as chignolin. The present inventors have also demonstrated that a polypeptide molecule capable of binding to a target substance can be identified using the library. The present invention has been completed on the basis of these findings.

Chignolin is an artificial microprotein that was developed by National Institute of Advanced Industrial Science and Technology (AIST) and is composed of only 10 amino acids (Non Patent Literatures 21 and 22). Chignolin forms a particular three-dimensional structure by spontaneous folding in a solution in spite of its size as small as a local region of a natural protein. At the moment, chignolin has the smallest molecular weight as a linear polypeptide with a noncyclic backbone exhibiting such properties and is recognized as the "smallest protein" (Non Patent Literatures 23 and 24). Nonetheless, a protein backbone-type library using chignolin or a chignolin-like microprotein as a scaffold has not yet been known.

Specifically, the present invention encompasses the following:

[1] A molecular library comprising a group of a plurality of molecules, wherein each member of the library is a polypeptide having a randomized sequence moiety and a microprotein moiety.

[2] The molecular library according to [1], wherein the microprotein is a protein comprising a linear polypeptide of 30 or less amino acid residues having the ability to form a particular conformation by spontaneous folding in a solution.

[3] The molecular library according to [1] or [2], wherein the microprotein is chignolin comprising the following amino acid sequence:
Gly Tyr Asp Pro Glu Thr Gly Thr Trp Gly (SEQ ID NO: 1)
or a chignolin variant comprising an amino acid sequence derived from the amino acid sequence by the deletion, substitution, insertion, or addition of one or several amino acid residues.

[4] The molecular library according to [3], wherein the microprotein is a chignolin variant comprising any of the following amino acid sequences:
Xaa Tyr Asp Pro Xaa Thr Gly Thr Trp Xaa (SEQ ID NO: 2)
Tyr Tyr Asp Pro Glu Thr Gly Thr Trp Trp (SEQ ID NO: 3)
Tyr Asp Pro Glu Thr Gly Thr Trp Tyr (SEQ ID NO: 4)
Tyr Asp Pro Xaa Thr Gly Thr Trp (SEQ ID NO: 5)
wherein Xaa represents an arbitrary amino acid residue.

[5] The molecular library according to any of [1] to [4], wherein each member of the library is a polypeptide molecule comprising the following amino acid sequence:
$(Xaa)_n$-Tyr-Asp-Pro-Xaa-Thr-Gly-Thr-Trp-$(Xaa)_m$ SEQ ID NO: 70
wherein Xaa represents an arbitrary amino acid residue, n represents an integer of 0 or larger, and m represents an integer of 0 or larger, provided that n and m are not both 0.

[6] The molecular library according to any of [1] to [4], wherein each member of the library is a polypeptide molecule comprising the following amino acid sequence:
$-[(Xaa)_n$-Tyr-Asp-Pro-Xaa-Thr-Gly-Thr-Trp-$(Xaa)_m]_k-$ (SEQ ID No: 701)
wherein Xaa represents an arbitrary amino acid residue, k represents an integer of 2 or larger, each n independently represents an integer of 0 or larger, and each m independently represents an integer of 0 or larger.

[7] The molecular library according to any of [1] to [6], wherein each member of the library further comprises a fixed sequence moiety.

[8] The library according to [7], wherein the fixed sequence moiety comprises a whole or partial amino acid sequence of a known polypeptide, or a whole or partial amino acid sequence of a polypeptide selected from the molecular library according to any of [1] to [6].

[9] The molecular library according to any of [1] to [8], wherein the polypeptide as each member of the library is present in a form associated with a polynucleotide encoding this polypeptide.

[10] The molecular library according to [9], wherein the polypeptide as each member of the library is linked to the polynucleotide encoding this polypeptide.

[11] The molecular library according to [9], wherein the polypeptide as each member of the library is displayed on the surface layer of a bacteriophage, and the polynucleotide encoding this polypeptide is incorporated in the bacteriophage.

[12] A polynucleotide library comprising a group of polynucleotides encoding members of the molecular library according to any of [1] to [11].

[13] A method for identifying a polypeptide molecule capable of binding to a target substance, comprising the following steps (a) to (c):
(a) contacting a library according to any of [7] to [11] with the target substance;
(b) selecting a member binding to the target substance from the library; and
(c) determining the amino acid sequence of the selected member.
[14] The method according to [13], wherein the determination of the amino acid sequence is carried out by the sequencing of the polynucleotide associated with the polypeptide.
[15] The method according to [13] or [14], wherein the target substance is a human immunoglobulin.

Advantageous Effects of Invention

A novel functional molecule having a small molecular weight can be prepared by use of the molecular library of the present invention. Chignolin forms a particular three-dimensional structure (β-hairpin structure) by a spontaneous folding in a solution state. At the moment, chignolin has the smallest molecular weight as a linear polypeptide exhibiting such properties and is recognized as the "smallest protein". As shown in Table 1, the length of 10 residues of chignolin is exceedingly small in size in consideration of at least approximately 50 or more residues of the proteins adopted in the known protein backbone-type libraries except for those having a cyclic backbone. Thus, the novel functional molecule that can be identified using the molecular library of the present invention has a lower molecular weight than that of a molecule that can be identified using any of the known protein backbone-type libraries. Specifically, a novel small protein with the drastically decreased number of amino acid residues can be prepared. A molecule having less than 50 amino acid residues is easily produced at a large scale by chemical synthesis and can be inexpensively prepared as compared with conventional methods dependent on cell culture. Reduced production cost can therefore be expected. In addition, the molecular library of the present invention is free from cyclization operation usually used in oligopeptide structure stabilization, because a spontaneously folding microprotein is incorporated therein. Thus, the molecule identified by selection from the library can be conveniently synthesized without the need of introduction of a functional group, complicated chemical reaction operation, and management for cyclization. An oligopeptide cyclized through the oxidation reaction of cysteine is generally difficult to use in a reduced environment such as the inside of cells. By contrast, the molecule identified from the molecular library of the present invention is free from such problems.

Figure 1:
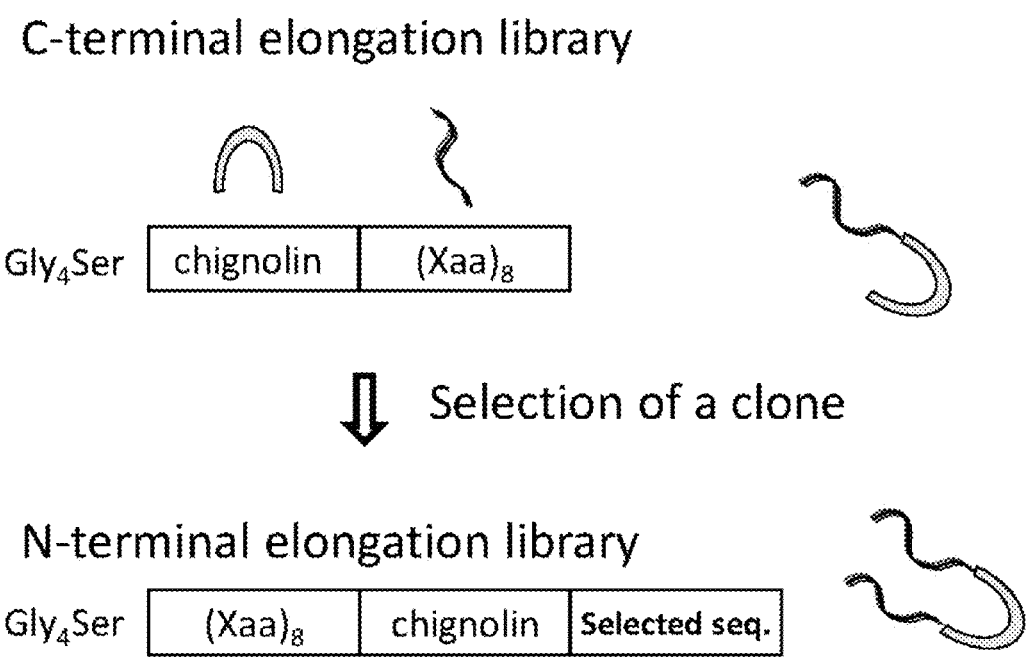
FIG. 1 shows the summary of design of a molecular library in which a microprotein chignolin variant is incorporated.

The present specification encompasses the contents described in the specification of Japanese Patent Application No. 2012-285734 on which the priority of the present application is based.

DESCRIPTION OF EMBODIMENTS

The present invention relates to a molecular library of polypeptides having the backbone structure of a microprotein, and a method for identifying a novel functional molecule using the library. In the present invention, the molecular library of polypeptides means an assembly of a plurality of polypeptides differing in amino acid sequence, and is constituted by a population of preferably $10^3$ or more types of polypeptide molecules, more preferably $10^6$ or more types of polypeptide molecules, most preferably $10^9$ or more types of polypeptide molecules.

The "function" of the functional molecule intended by the present invention refers to every function known about natural biopolymers, such as binding affinity, recognizing properties, catalytic activity, and inhibitory activity. The novel functional molecule having these "functions" can be applied for the purpose of developing pharmaceutical products, testing drugs, research reagents, agricultural chemicals, enzymes, sensors, coagulants, scavengers, separating agents, inhibitors, etc. In this context, when a novel molecule having binding affinity for a certain target substance is to be identified, the target substance is not particularly limited by its type and includes not only biopolymers but nonbiological molecules or nonnatural nonbiological materials, for example, proteins, saccharides, glycoproteins, nucleic acids, and low-molecular compounds (Reference 1). Examples thereof include receptors, cell surface antigens, antibodies, hormones, DNAs, RNAs, and virus surface antigens.

A feature of the molecular library of the present invention is that each member constituting the library has a backbone structure based on a microprotein. In general, the functions of biopolymers such as proteins are known to be improved by the stabilization of their conformations (References 2 and 3). The functions improved by structure stabilization are not particularly limited and include every function known about natural biopolymers, such as binding affinity, recognizing properties, catalytic activity, and inhibitory activity. Thus, if the structure stabilization of the novel functional molecule can be achieved by the incorporation of a microprotein, its functions may be effectively improved. As described later in detail in Example 1, a molecular library constituted by polypeptide molecules comprising a sequence moiety of a microprotein was prepared and then used to identify a novel molecule having binding affinity for a target substance. It was demonstrated that the identified novel molecule forms a stable conformation and also exhibits remarkable improvement in binding affinity.

A feature of the molecular library of the present invention is that each member constituting the library is a polypeptide comprising a sequence moiety of a microprotein. In this context, the microprotein refers to a protein consisting of an amino acid sequence of 30 or less amino acid residues, preferably 20 or less amino acid residues, more preferably 10 or less amino acid residues and having the ability to form a particular conformation by spontaneous folding in a solution.

One preferred example of the microprotein includes chignolin comprising the amino acid sequence represented by SEQ ID NO: 1.
Gly Tyr Asp Pro Glu Thr Gly Thr Trp Gly (SEQ ID NO: 1)
Chignolin is an artificial protein that was developed by National Institute of Advanced Industrial Science and Technology (AIST), and forms a particular three-dimensional structure by spontaneous folding in a solution (References 4 and 5). At the moment, chignolin has the smallest molecular weight as a linear polypeptide with a noncyclic backbone exhibiting such properties and is recognized as the "smallest protein" (References 6 and 7). Thus, a molecular library that adopts chignolin as the microprotein, i.e., a molecular library based on the backbone structure of chignolin, is one of the particularly preferred modes for carrying out the present invention.

Alternatively, a chignolin variant may be adopted instead of chignolin. In this context, the chignolin variant refers to a molecule comprising an amino acid sequence derived from the amino acid sequence represented by SEQ ID NO: 1 by the deletion, substitution, insertion, or addition of one or several amino acid residues. Many theoretical studies have been made on chignolin (References 8 to 12) and revealed that Tyr at position 2, Asp at position 3, Pro at position 4, Thr at position 6, Gly at position 7, Thr at position 8, and Trp at position 9 are important for the formation of the particular three-dimensional structure. Thus, an oligopeptide comprising any of the following amino acid sequences:
Xaa Tyr Asp Pro Xaa Thr Gly Thr Trp Xaa (SEQ ID NO: 2)
Tyr Tyr Asp Pro Glu Thr Gly Thr Trp (SEQ ID NO: 3)
Tyr Asp Pro Glu Thr Gly Thr Trp Tyr (SEQ ID NO: 4)
Tyr Asp Pro Xaa Thr Gly Thr Trp (SEQ ID NO: 5)
wherein Xaa represents an arbitrary amino acid residue is one of the preferred forms of the chignolin variant.

Each member of the molecular library of the present invention has a microprotein moiety that constitutes the backbone structure, and a randomized sequence moiety added to the N or C terminus, or both, of the microprotein. In the randomized sequence moiety, at least a partial amino acid sequence is randomized. The randomization refers to the preparation of an assembly of polypeptides in which 2 or more types of amino acid residues are assigned to an arbitrary given position of the polypeptides. In the randomized sequence moiety, all possible amino acid residues may be present with the same or different probabilities at the given position, or selected 2 or more types of particular amino acid residues may be present at the given position. For example, 20 types of amino acid residues can each be present with a probability of 5% at the particular position in the sequences. The probability of the presence of each amino acid residue is not limited to 5% and can be varied. Alternatively, the amino acid sequences, only at the particular position, of the polypeptides may be randomized, and the sequences of the remaining positions may be fixed. The amino acids may be natural amino acids or nonnatural amino acids. The randomized sequence is not limited by its chain length and is preferably constituted by 40 or less, more preferably 20 or less amino acid residues, in total including both terminal residues.

In a preferred embodiment of the present invention, each member of the library is a polypeptide molecule comprising the following amino acid sequence:
(Xaa)$_n$-Tyr-Asp-Pro-Xaa-Thr-Gly-Thr-Trp-(Xaa)$_m$
wherein Xaa represents an arbitrary amino acid residue, n represents an integer of 0 or larger, and m represents an integer of 0 or larger, provided that n and m are not both 0. Each of n and m is an integer of preferably 1 to 20, more preferably 3 to 15, further preferably 5 to 10. Also preferably, the total of n and m is 40 or less, more preferably 20 or less.

In another preferred embodiment of the present invention, each member of the library may comprise two or more microprotein moieties. One example of such a library can include a library, each member of which is a polypeptide molecule comprising the following amino acid sequence unit:
-[(Xaa)$_n$-Tyr-Asp-Pro-Xaa-Thr-Gly-Thr-Trp-(Xaa)$_m$]$_k$-
wherein Xaa represents an arbitrary amino acid residue, k represents an integer of 2 or larger, each n independently represents an integer of 0 or larger, and each m independently represents an integer of 0 or larger. Preferably, k is 2 to 4. In each unit, n and m are each independently an integer of preferably 1 to 20, more preferably 3 to 15, further preferably 5 to 10. Also preferably, the total of n and m in each unit is 40 or less, more preferably 20 or less.

In addition to chignolin, 20-residue Trp-cage protein (amino acid sequence: NLYIQWLKDGGPSSGRPPPS (SEQ ID NO: 48), Reference: Neidigh J W, Fesinmeyer R M, Andersen N H. (2002) Designing a 20-residue protein. Nat Struct Biol. 9 (6): 425-430) and 28-residue FSD-1 (amino acid sequence: EQYTAKYKGRTFRNEKELRD-FIEKFKGR (SEQ ID NO: 49), Reference: Sarisky C A, Mayo S L. (2001) The beta-beta-alpha fold: explorations in sequence space. J Mol Biol. 307 (5): 1411-1418) are known as spontaneously folding proteins of 30 or less amino acid residues. An 18-residue peptide that folds via a metal ion (amino acid sequence: YIDTNNDGWYEGDELLAX (SEQ ID NO: 50), Reference: Nitz M, Sherawat M, Franz K J, Peisach E, Allen K N, Imperiali B. (2004) Structural origin of the high affinity of a chemically evolved lanthanide-binding peptide. Angew Chem Int Ed Engl. 43 (28): 3682-3685) has also been reported. Also see the category "Small proteins" (http://scop.mrc-lmb.cam.ac.uk/scop/data/scop.b-.h.html) or the category "Designed proteins" (http://scop-.mrc-lmb.cam.ac.uk/scop/data/scop.b.bb.html) of the spontaneously folding protein classification database SCOP. Any of these proteins can be used as the microprotein according to the present invention.

The randomized sequence moiety may be added to the microprotein by a plurality of stages. FIG. 1 and Example 1 described later show one example of the design of a molecular library in which a microprotein chignolin variant is incorporated. The molecular library is designed in stages. At the first stage, an elongation library is prepared such that the C terminus of the chignolin variant (in the diagram, indicated as chignolin) is elongated with an 8-residue-long random region and a glycine residue [(Xaa)$_8$Gly]. Subsequently, each clone is selected for a target, and its amino acid sequence is identified. At the second stage, an elongation library is prepared such that the identified amino acid sequence (in the diagram, indicated as Selected seq.) is linked to the C terminus of the chignolin variant while the N terminus thereof is elongated with an 8-residue-long random region. This library is used to select and identify each functional molecule again. The randomized sequence addition step and the functional molecule selection step are thus repetitively carried out because search for appropriate sequence space is achieved by the elongation of the functional molecule in stages, resulting in the increased expectations of conformation stabilization and improvement in function for the obtained molecule. This is one of the particularly preferred modes for carrying out the present invention. In Example 1 described later, the C terminus was first elongated, and the N terminus was subsequently elongated. This order has no scientific necessity, and elongation in the opposite order is not excluded as long as the molecular library of the present invention is used. In Example 1 described later, the randomized sequence of approximately 8 residues in length was added. As with the existing protein backbone-type libraries, which adopt randomized sequences having various lengths (Table 1), elongation using other residue lengths is not excluded. Since the size (diversity) of the library depends on the length of the residues to be randomized, the optimum length can be appropriately selected according to the display method of the library or the selection method used.

Each member of the library of the present invention may further comprise a fixed sequence moiety having a particular sequence, in addition to the microprotein moiety and the randomized sequence moiety. Specifically, the library of the present invention may be in the form of a library of fusion proteins with a peptide or a protein having a particular sequence. As shown later in Example 2, for example, an amino acid sequence of approximately 13 residues known to have low binding affinity for a particular target substance is added to the N terminus of a chignolin variant comprising the amino acid sequence represented by SEQ ID NO: 3. Then, a randomized sequence of approximately 10 residues in length is added to the C terminus thereof to prepare library. This library may be used to select a novel functional molecule having high binding affinity for the target substance.

A sequence known or predicted to have some function, such as a biologically active peptide, a sequence motif, an epitope, a paratope, an affinity tag, or a fragment positioned at the interface of a protein-protein complex, is preferably used as the particular sequence to be added. Alternatively, a particular sequence having an unknown function may be added. In the section 1) of Example 2 described later, the particular sequence was added to the N terminus of the chignolin variant. However, the addition thereof to the C terminus is not excluded.

Figure 7:
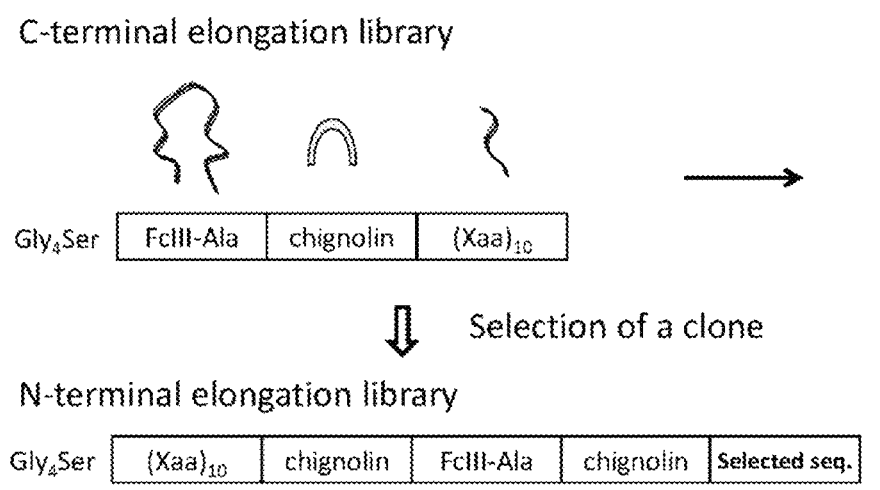
FIG. 7 shows the summary of design of a molecular library in which a particular sequence and a microprotein chignolin variant are incorporated.
Figure 7:
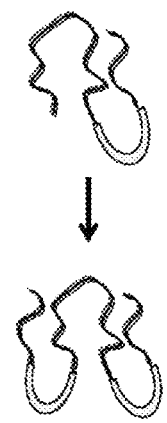
Figure 8:
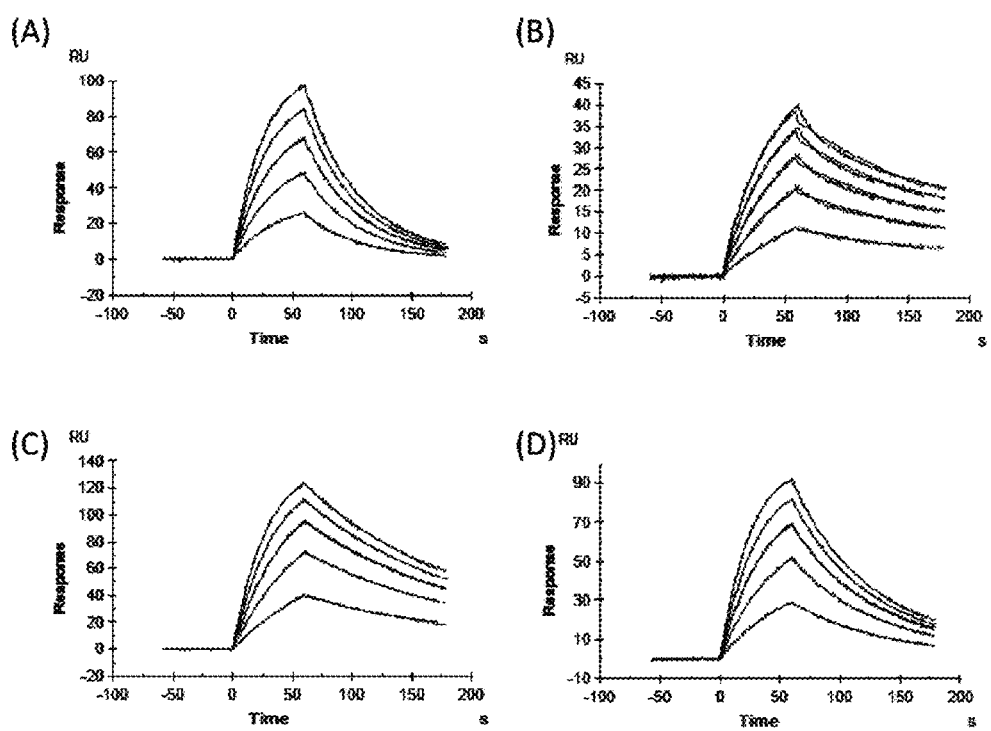
FIG. 8(A) shows results of the binding affinity analysis of pep11 peptide for a human Fc region by surface plasmon resonance. The diagram depicts the binding curve of each pep11 peptide diluted to a concentration of 500, 400, 300, 200, or 100 nM for the human Fc region immobilized on a sensor chip.
FIG. 8(B) shows results of the binding affinity analysis of pep14 peptide for a human Fc region by surface plasmon resonance. The diagram depicts the binding curve of each pep14 peptide diluted to a concentration of 500, 400, 300, 200, or 100 nM for the human Fc region immobilized on a sensor chip.
FIG. 8(C) shows results of the binding affinity analysis of pep21 peptide for a human Fc region by surface plasmon resonance. The diagram depicts the binding curve of each pep21 peptide diluted to a concentration of 500, 400, 300, 200, or 100 nM for the human Fc region immobilized on a sensor chip.
FIG. 8(D) shows results of the binding affinity analysis of pep24 peptide for a human Fc region by surface plasmon resonance. The diagram depicts the binding curve of each pep24 peptide diluted to a concentration of 500, 400, 300, 200, or 100 nM for the human Fc region immobilized on a sensor chip.

As shown later in Example 3, this method of adding the particular sequence may be combined with the aforementioned method involving elongation in stages to prepare a novel functional molecule. FIG. 7 shows one example of such a method. The molecular library containing a particular sequence moiety is designed in stages. At the first stage, an elongation library is prepared such that a chignolin variant (in the diagram, indicated as chignolin) and a 10-residue-long random region $(Xaa)_{10}$ are added to the C terminus of a particular sequence (in the diagram, indicated as FcIII-Ala). Subsequently, each clone is selected for a target, and its amino acid sequence is identified. At the second stage, an elongation library is prepared such that the identified amino acid sequence (in the diagram, indicated as Selected seq.) and a chignolin variant are linked to the C terminus of the particular sequence while the N terminus of the particular sequence is elongated with a chignolin variant and a 10-residue-long random region.

For identifying a polypeptide having the function of interest by evolutionary molecular engineering (or in vitro evolution), it is required that the genotype and phenotype of this polypeptide molecule should be associated with each other (Reference 13). Specifically, each polypeptide constituting the molecular library is present in a form associated with a polynucleotide encoding this polypeptide. In this context, the term "associated" means that the polypeptide and a polynucleotide encoding this polypeptide are present in a manner where the polypeptide and the polynucleotide can be associated with each other on a one-to-one basis. Such an association technique is also called display technology, and many techniques are known in the art.

In a preferred embodiment, the polypeptide as each member of the library is linked to the polynucleotide encoding this polypeptide. In another preferred embodiment, the polypeptide as each member of the library is displayed on the surface layer of a bacteriophage, and the polynucleotide encoding this polypeptide is incorporated in the bacteriophage.

By use of such a polypeptide-polynucleotide library, the amino acid sequence of the polypeptide having the function of interest can be easily determined by the sequencing of the polynucleotide associated therewith. By use of the molecular library of polypeptides in a form associated with their polynucleotides, a group of target-bound polypeptides is selected, and a group of polynucleotides encoding these polypeptides can then be recovered and amplified, followed by transcription and translation to produce a second polypeptide molecular library. Each individual member polypeptide of this second molecular library has the same microprotein moiety and randomized moiety as those of the original molecular library. Nonetheless, it is expected that the functions (e.g., affinity for the target) as the whole library are improved and the sequence diversity of the randomized moiety is decreased. Similarly, third and fourth molecular libraries can be produced. In this way, the library formation and the selection can be carried out in multiple stages to obtain an assembly of polypeptides having higher affinity for the target.

In the present invention, the method for synthesizing the polynucleotide encoding each polypeptide constituting the molecular library, the form of the library, the display method of the library, the method for immobilizing a target substance, the method for selecting a binding molecule, the method for identifying the sequence of a molecule having binding affinity, and the method for confirming the functions of the binding molecule include all technically applicable forms among forms generally known to those skilled in the art, as described below in detail.

The molecular library of the present invention can be produced manually or automatically using an ordinary peptide synthesis technique. Alternatively, the polynucleotide encoding the polypeptide as each member of the molecular library may be produced as a library, and the polypeptide can be expressed in a cell-free system or in bacterial or animal cells to produce the molecular library of the present invention. Specifically, the present invention also provides a molecular library of polynucleotides as an assembly of polynucleotides encoding the polypeptides of the aforementioned polypeptide molecular library of the present invention. Each member of the polynucleotide library may further have a sequence necessary for phage infection, a sequence for the expression of the polypeptide, a vector sequence for the amplification of the polynucleotide in a bacterium or the like, a linker or adaptor sequence for the addition of these sequences, etc., in addition to the sequence encoding the polypeptide.

Examples of the method for synthesizing the polynucleotide include organic synthesis and enzymatic synthesis methods (Reference 14). In recent years, long-chain polynucleotides have also been synthesized by organic synthesis (Reference 15). Examples of the enzymatic synthesis methods include polymerase chain reaction (PCR) (Reference 16), rolling circle amplification (RCA) (Reference 17), and loop-mediated amplification (LAMP) (Reference 18). In Example 1 described later, the enzymatic synthesis and amplification of organically synthesized DNAs by PCR were shown as an example of the synthesis method. However, other methods including the aforementioned techniques are not excluded.

The molecular library of the present invention can be used in various in vitro or in vivo methods for the purpose of identifying a polypeptide having the function of interest. A plurality of techniques have previously been reported as to library forms or display methods of libraries. Typical examples of the methods routinely used include a filamentous phage display method (Reference 19), a λ phage display method (Reference 20), a T7 phage display method (Reference 21), a ribosome display method (Reference 22), an mRNA display method (Reference 23), a yeast surface display method (Reference 24), an E. coli thioredoxin display method (Reference 25), yeast two-hybrid screening (Reference 26), and high-throughput screening using a protein array technique (Reference 27). In Example 1 described later, the T7 phage display method was shown as an example. However, display methods in other forms including the aforementioned techniques are not excluded.

In another aspect, the present invention provides a method for identifying a polypeptide molecule capable of binding to a target substance using the molecular library of the present invention. In this method, the library of the present invention is first contacted with the target substance. The contact of the molecular library with the target can be carried out by the addition of the molecular library and the target into an appropriate buffer solution followed by incubation for a predetermined time. The conditions for the contact can be set such that a polypeptide having high affinity for the target remains bound with the target substance, whereas a polypeptide having low affinity for the target is not bound thereto. Such conditions can be selected in consideration of the properties of the target, use of the polypeptide to be selected according to the present invention, the degree of predicted nonspecific binding, etc. In the case of selection by a plurality of stages, the conditions for the contact may be changed on a stage basis.

Next, target substance-unbound polypeptides are removed from the polypeptide library to select a target substance-bound polypeptide. For facilitating this selection step, it is convenient to immobilize either the polypeptide library or the target on a solid phase. Any solid phase known in the art, such as a resin column, a glass or plastic plate, beads, porous particles, a membrane, or magnetic particles, can be used. Examples of the immobilization method include a chemical binding method via Lys residues or the N-terminal amino groups of polypeptides, a chemical binding method via the thiol groups of Cys residues, a chemical binding method via carboxyl groups, a method by metal-ligand bonds, a method using affinity tags, physical adsorption, a method using protein splicing with intein, a method via DNA complementary strands, and a method via avidin-biotin (Reference 28). In Examples 1 and 2 described later, the chemical binding via Lys residues and the avidin-biotin method were shown as examples of the immobilization method. However, other methods including the aforementioned techniques are not excluded.

Examples of the method for selecting the molecule having binding affinity for the target substance include a method using magnetic beads (Reference 29), a method using a plate (Reference 30), a method using Immunotube (Reference 31), a method by flow cytometry (Reference 32), a method using a column (Reference 33), and a method by centrifugation (Reference 34). In Example 1 described later, the method using magnetic beads was shown as an example. However, other methods including the aforementioned techniques are not excluded.

The polypeptide thus selected is recovered, and its amino acid sequence can be determined to identify the polypeptide binding to the target substance. In a particularly preferred embodiment, the amino acid sequence of the polypeptide is determined by the sequencing of the polynucleotide encoding this polypeptide. Examples of the method for identifying the sequence of the polynucleotide include a dideoxy method, a Maxam-Gilbert method, Pyrosequencing®, a single-molecule detection method using exonuclease (Reference 35), and second-generation parallel DNA sequencing (Reference 36). In Example 1 described later, the dideoxy method was shown as an example. However, other methods including the aforementioned techniques are not excluded.

The polypeptide thus identified can be applied, as a substance capable of binding to the particular target substance, for the purpose of developing pharmaceutical products, testing drugs, research reagents, agricultural chemicals, enzymes, sensors, coagulants, scavengers, separating agents, inhibitors, etc. Examples of the method for preparing the polypeptide include an organic chemical synthesis method, a method based on gene recombination (Reference 37), and a method involving expression in the form of a fusion protein linked to an arbitrary protein (Reference 38). In Examples 1 and 2 described later, the preparation by organic chemical synthesis was shown. In Example 3, the preparation by cellular expression as a fusion protein and the preparation of the polypeptide of interest by the protease cleavage of the fusion protein were shown. However, other methods including the aforementioned techniques are not excluded.

Examples of the method for confirming the functions of the identified molecule having binding affinity include enzyme-linked immunosorbent assay (ELISA), a surface plasmon resonance (SPR) method, isothermal titration calorimetry (ITC), quartz crystal microbalance (QCM), atomic force microscopy (Reference 39), a pulldown method (Reference 40), electrophoresis (Reference 41), and fluorescence polarization assay (Reference 42). In Example 1 described later, the enzyme-linked immunosorbent assay and the surface plasmon resonance method were shown as examples. However, other methods including the aforementioned techniques are not excluded.

For example, the method of Szostak et al. used for searching for a novel molecule having RNA ligase activity as an example of the selection of a catalytically active molecule (Reference 2) is known as a method for selecting a molecule having a function other than binding affinity or a method for confirming the function. In the present invention, these methods also include all technically applicable forms among forms generally known to those skilled in the art.

REFERENCE

Reference 1; Seker U O and Demir H V. (2011) Molecules. 16(2) 1426-1451.
Reference 2; Seelig B and Szostak J W (2007) Selection and evolution of enzymes from a partially randomized non-catalytic scaffold. Nature. 448(7155) 828-831.
Reference 3; Salgado E N, Ambroggio X I, Brodin J D, Lewis R A, Kuhlman B and Tezcan F A. (2010) Metal templated design of protein interfaces. Proc Natl Acad Sci USA. 107(5) 1827-1832.

Reference 4; Honda, S. Yamasaki, Y. Sawada, and H. Morii (2004) 10-residue folded peptide designed by segment statistics Structure 12(8) 1507-1518.

Reference 5; Honda, S., Akiba, T., Kato, Y. S., Sawada, Y., Sekijima, M., Ishimura, M., Ooishi, A., Watanabe, H., Odahara, T. and Harata, K. (2008) Crystal Structure of a Ten-Amino Acid Protein J. Am. Chem. Soc., 130(46), 15327-15331.

Reference 6; Shinya Honda ""Protein" of 10 amino acids, discovery of chignolin", Protein, Nucleic acid and Enzyme (PNE), 50 (5), 427-433 (2005).

Reference 7; Shinya Honda "Minimal Design of Protein: Structure and wobbling of super chignolin", Journal of the Biophysical Society of Japan, 49 (3), 126-129 (2009).

Reference 8; Satoh D, Shimizu K, Nakamura S and Terada T. (2006) Folding free-energy landscape of a 10-residue mini-protein, chignolin. FEBS Lett. 580(14) 3422-3426.

Reference 9; Xu W, Lai T, Yang Y and Mu Y. (2008) Reversible folding simulation by hybrid Hamiltonian replica exchange. J Chem Phys. 128(17) 175105.

Reference 10; Terada T, Satoh D, Mikawa T, Ito Y and Shimizu K. Understanding the roles of amino acid residues in tertiary structure formation of chignolin by using molecular dynamics simulation. (2008) Proteins. 73(3) 621-631.

Reference 11; Roy S, Goedecker S, Field M J, Penev E. (2009) A minima hopping study of all-atom protein folding and structure prediction. J Phys Chem B. 113(20) 7315-7321.

Reference 12; Hatfield M P, Murphy R F and Lovas S. (2010) Molecular dynamics analysis of the conformations of a beta-hairpin miniprotein. J Phys Chem B. March 114(8) 3028-3037.

Reference 13; Yuzuru Fushimi (1992), Beginning of evolutionary molecular engineering, Journal of the Biophysical Society of Japan, 32, 22-25

Reference 14; Osamu Ohara, Hisaaki Taniguchi, Tetsuo Ichikawa, Atsushi Inukai, Biological High-Performance Equipment—New Technical Manuals, Kyoritsu Shuppan Co., Ltd.

Reference 15; Smith H O, Hutchison C A 3rd, Pfannkoch C and Venter J C. (2003) Generating a synthetic genome by whole genome assembly: phiX174 bacteriophage from synthetic oligonucleotides. Proc Natl Acad Sci USA. 100(26) 15440-15445.

Reference 16; Mullis K B and Faloona F A. (1987) Specific synthesis of DNA in vitro via a polymerase-catalyzed chain reaction. Methods Enzymol. 155 335-350.

Reference 17; Baner J, Nilsson M, Mendel-Hartvig M and Landegren U. (1998) Signal amplification of padlock probes by rolling circle replication. Nucleic Acids Res. 26(22) 5073-5078.

Reference 18; Notomi T, Okayama H, Masubuchi H, Yonekawa T, Watanabe K, Amino N and Hase T. (2000) Loop-mediated isothermal amplification of DNA. Nucleic Acids Res. 28(12 E63)

Reference 19; Kehoe J W and Kay B K. (2005) Filamentous phage display in the new millennium. Chem Rev. 105(11) 4056-4072.

Reference 20; Cicchini C, Ansuini H, Amicone L, Alonzi T, Nicosia A, Cortese R, Tripodi M and Luzzago A. (2002) Searching for DNA-protein interactions by lambda phage display. J Mol Biol. 322(4) 697-706.

Reference 21; Danner S and Belasco J G. (2001) T7 phage display: a novel genetic selection system for cloning RNA-binding proteins from cDNA libraries. Proc Natl Acad Sci USA. 98(23) 12954-12959.

Reference 22; Hanes J and Pluckthun A. (1997) In vitro selection and evolution of functional proteins by using ribosome display. Proc Natl Acad Sci USA. 94(10) 4937-4942.

Reference 23; Wilson D S, Keefe A D and Szostak J W. (2001) The use of mRNA display to select high-affinity protein-binding peptides. Proc Natl Acad Sci USA. 98(7) 3750-3755.

Reference 24; Boder E T and Wittrup K D. (1997) Yeast surface display for screening combinatorial polypeptide libraries. Nat Biotechnol. 15(6) 553-557.

Reference 25; Lu Z, Murray K S, Van Cleave V, LaVallie E R, Stahl M L and McCoy J M. (1995) Expression of thioredoxin random peptide libraries on the *Escherichia coli* cell surface as functional fusions to flagellin: a system designed for exploring protein-protein interactions. Nat Biotechnology 13, 366-372.

Reference 26; Fields S and Song 0. (1989) A novel genetic system to detect protein-protein interactions. Nature. 340 (6230) 245-246.

Reference 27; Walter G, Bussow K, Cahill D, Lueking A and Lehrach H. (2000) Protein arrays for gene expression and molecular interaction screening. Curr Opin Microbiol. 3(3) 298-302.

Reference 28; Rusmini F, Zhong Z and Feijen J. (2007) Protein immobilization strategies for protein biochips. Biomacromolecules. 8(6) 1775-1789.

Reference 29; Backstrom A, Lundberg C, Kersulyte D, Berg D E, Boren T and Arnqvist A. (2004) Metastability of *Helicobacter pylori* bab adhesin genes and dynamics in Lewis b antigen binding. Proc Natl Acad Sci USA. 101(48) 16923-16928.

Reference 30; Begum N, Horiuchi S, Tanaka Y, Yamamoto N, Ichiyama K and Yamamoto N. (2002) New approach for generation of neutralizing antibody against human T-cell leukaemia virus type-I (HTLV-I) using phage clones. Vaccine. 20(9-10) 1281-1289.

Reference 31; Khuebachova M, Verzillo V, Skrabana R, Ovecka M, Vaccaro P, Panni S, Bradbury A and Novak M. (2002) Mapping the C terminal epitope of the Alzheimer's disease specific antibody MN423. J Immunol Methods. 262(1-2) 205-215.

Reference 32; Kronqvist N, Lofblom J, Jonsson A, Wernerus H and Stahl S. (2008) A novel affinity protein selection system based on staphylococcal cell surface display and flow cytometry. Protein Eng Des Sel. 21(4) 247-255.

Reference 33; Noppe W, Plieva F, Galaev I Y, Pottel H, Deckmyn H and Mattiasson B. (2009) Chromato-panning: an efficient new mode of identifying suitable ligands from phage display libraries. BMC Biotechnol. 9 21.

Reference 34; Watanabe H, Nakanishi T, Umetsu M and Kumagai I. (2008) Human anti-gold antibodies: biofunctionalization of gold nanoparticles and surfaces with anti-gold antibodies. J Biol Chem. 283(51) 36031-36038.

Reference 35; Franca L T, Carrilho E and Kist T B. (2002) A review of DNA sequencing techniques. Q Rev Biophys. 35(2) 169-200.

Reference 36; Shendure J and Ji H. (2008) Next-generation DNA sequencing. Nat Biotechnol. 26(10) 1135-1145.

Reference 37; Kenji Kangawa, Peptides and Drug Discovery, Medical Do

Reference 38; Tatsuya Moriyama, Knowhow of Protein Purification and Handling, Yodosha Co., Ltd.

Reference 39; Tairo Oshima, Koichi Suzuki, Yoshiaki Fujii, Takashi Muramatsu, Post-Sequencing Protein Experiment Methods 3, Tokyo Kagaku Dozin Co., Ltd.

Reference 40; Brymora A, Valova V A and Robinson P J. (2004) Protein-protein interactions identified by pulldown experiments and mass spectrometry. Curr Protoc Cell Biol. 17 Unit 17.5

Reference 41; Wittig I and Schagger H. (2009) Native electrophoretic techniques to identify protein-protein interactions. Proteomics. 9(23) 5214-23.

Reference 42; Park S H and Raines R T. (2004) Fluorescence polarization assay to quantify protein-protein interactions. Methods Mol Biol. 261 161-166

Hereinafter, the present invention will be described further specifically with reference to Examples. However, the technical scope of the present invention is not intended to be limited by these Examples.

Example 1

This Example describes a method comprising preparing a polypeptide library of molecules containing a microprotein as a backbone and using the library to identify a novel molecule having binding affinity for an Fc region, which is a portion of a constant region of human immunoglobulin G (IgG). The preparation of the library was carried out by a method involving elongation in stages to sequentially add random sequences.

1) Construction of C-Terminal Elongation Library

This section shows the construction of a library in which an 8-residue-long random sequence $(Xaa)_8$ was added to the C terminus of a chignolin variant consisting of the 8-residue-long amino acid sequence represented by SEQ ID NO: 5, and a 5-residue-long linker Gly Gly Gly Gly Ser was added to the N terminus thereof (FIG. 1). The T7 phage display method was used for one form in which each polynucleotide constituting the library and its expression product polypeptide were associated with each other.

First, a DNA (SEQ ID NO: 7) in which restriction enzyme sites EcoRI and HindIII were added to a DNA encoding the amino acid sequence represented by SEQ ID NO: 6 was designed as the polynucleotide encoding each polypeptide of the library. In this context, the arbitrary natural amino acid residue Xaa is encoded by a mixed base triplet NNK. In the sequence, N represents a mixed base A, C, G, or T, and K represents a mixed base G or T. The synthetic DNA of SEQ ID NO: 7 used was purchased from Rikaken Co., Ltd., and this DNA was amplified by polymerase chain reaction (PCR). The PCR was carried out using KOD DNA polymerase (Toyobo Co., Ltd.) under reaction conditions that followed the attached manual. The amplified DNA was digested with restriction enzymes EcoRI and HindIII and then ligated to the 3' end of g10 gene on the T7 phage genomic DNA. The T7 phage genomic DNA used was a sample attached to T7Select 10-3 Cloning Kit (Novagen/Merck KGaA), and the reaction conditions and procedures followed the attached T7Select® System Manual. The ligated T7 phage genomic DNA was used in the in vitro packaging of the T7 phage using T7Select Packaging Kit (Novagen/Merck KGaA). The reaction conditions followed T7Select® System Manual (Novagen/Merck KGaA). As a result, a phage library having DNAs encoding $5 \times 10^6$ types of polypeptides was constructed.

Subsequently, the phage library was amplified. First, an *E. coli* BLT5403 strain (Novagen/Merck KGaA) cultured until O.D. 600=1.0 in 200 ml of an LB medium was infected by the phage library and shake-cultured for 4 hours. The culture solution was centrifuged at 5000×g for 20 minutes to recover a medium supernatant containing amplified phages. To this supernatant, 20 ml of 5 M NaCl (Wako Pure Chemical Industries, Ltd.) and 35 ml of 50% polyethylene glycol (PEG) 8000 (Sigma-Aldrich Corp.) were added, and the mixture was stirred at 4° C. for 12 hours. This mixture was centrifuged at 14000×g for 20 minutes. The precipitate was suspended in 2 ml of a TBS-T buffer solution (50 mM Tris-HCl, 150 mM NaCl, and 0.01% (w/v) Tween 20®, pH 7.4). The suspension was filtered through a filter having a pore size of 0.22 μm to remove aggregates. The solution prepared by the above operation was used as the T7 phage display library, one form of the molecular library in which the polypeptide of SEQ ID NO: 6 was associated with the polynucleotide of SEQ ID NO: 7.

2) Selection for Human IgG Fc Region

Subsequently, use of the T7 phage display library constructed in the preceding section is shown in the steps of: contacting the library with the target substance human IgG Fc region; and selecting and recovering phages bound with the human IgG Fc region.

This section shows a method using magnetic beads as one example of the method for selecting molecules having binding affinity. First, 0.65 ml of Streptavidin MagneSphere® Paramagnetic Particles (Promega K.K.) used as avidin-immobilized magnetic beads was mixed with 20 μg of a biotin-labeled human IgG Fc region (Jackson ImmunoResearch Laboratories, Inc.) to immobilize the Fc region onto the magnetic beads via avidin-biotin bonds. The Fc region-immobilized magnetic beads were blocked by the addition of a blocking agent SuperBlock® T20 (TBS) Blocking Buffer (Thermo Fisher Scientific Inc.) thereto over 1 hour. The T7 phage display library solution (1 ml; $5 \times 10^{12}$ plaque forming units) prepared in the section 1) of Example 1 was contacted with the Fc region-immobilized magnetic beads for 1 hour so that phages displaying polypeptides exhibiting binding affinity for the Fc region were bound with the Fc region-immobilized magnetic beads. Then, the complexes of the polypeptide-exhibiting phages and the Fc region-immobilized magnetic beads were recovered by magnetic separation using MagneSphere® Technology Magnetic Separation Stand (Promega K.K.). To the recovered complexes, 1 ml of SuperBlock® T20 (TBS) Blocking Buffer (Thermo Fisher Scientific Inc.) was added, and the mixture was mixed for 10 minutes, followed by the removal of the supernatant by magnetic separation again to recover the complexes. This washing operation was carried out 10 times. After the washing, 1 ml of a TBS-T buffer solution containing 1% (w/v) sodium dodecyl sulfate (SDS) was added to the complexes recovered by magnetic separation, and the mixture was mixed for 10 minutes to elute phages displaying polypeptides having binding affinity from the Fc region-immobilized magnetic beads. An *E. coli* BLT5403 strain (Novagen/Merck KGaA) cultured until O.D. 600=1.0 in 200 ml of an LB medium was infected by each of the eluted phages and shake-cultured for 4 hours. The culture solution was centrifuged at 5000×g for 20 minutes to recover a medium supernatant containing amplified phages. To this supernatant, 20 ml of 5 M NaCl (Wako Pure Chemical Industries, Ltd.) and 35 ml of 50% polyethylene glycol (PEG) 8000 (Sigma-Aldrich Corp.) were added, and the mixture was stirred at 4° C. for 12 hours. This mixture was centrifuged at 14000×g for 20 minutes. The precipitate was suspended in 2 ml of a TBS-T buffer solution (50 mM Tris-HCl, 150 mM NaCl, and 0.01% (w/v) Tween 20®, pH 7.4). The suspension was filtered through a filter having a pore size of 0.22 μm to remove aggregates. In this way, a T7 phage solution was obtained. These "steps of: contacting the library with the target substance human IgG Fc region; and selecting and recovering phages bound with the human IgG Fc region" were repeated five times to enrich the phages displaying polypeptides exhibiting binding affinity.

3) Binding Affinity Test by ELISA and Identification of Affinity Polypeptide by Sequence Analysis Subsequently, the step of confirming the functions of a molecule having binding affinity from the enriched phage population by ELISA is shown.

Phage plaques were formed according to T7Select® System Manual (Novagen/Merck KGaA) from the population of the phages displaying polypeptides exhibiting binding affinity, enriched in the section 2) of Example 1. From each of these plaques, a phage displaying a single polypeptide was isolated. To MICROTEST® 96 (Becton, Dickinson and Company) used as a 96-well plate, 0.2 ml of a culture solution of an E. coli BL5403 strain cultured until O.D. 600=1.0 in an LB medium was added, and this strain was infected by each of 96 phages respectively isolated from their plaques and left standing at 37° C. for 12 hours to amplify the phages. The culture solution (10 µl) containing these phages was diluted with 90 µl of a TBS buffer solution (50 mM Tris-HCl, and 150 mM NaCl, pH 7.4), and this dilution was added to MEDISORP 96 well microplate (Nunc/Thermo Fisher Scientific Inc.) over 1 hour so that the phages were physically adsorbed onto the plate. The supernatant was removed, and the plate surface was blocked by the addition of 150 µl/well of SuperBlock® T20 (TBS) Blocking Buffer (Thermo Fisher Scientific Inc.) over 1 hour and then washed with a TBS-T buffer solution three times. A TBS-T buffer solution containing horseradish peroxidase (HRP)-labeled Fc region (Jackson ImmunoResearch Laboratories, Inc.) (0.2 µg/ml) was added thereto at 100 µl/well and left standing for 1 hour. After washing with a TBS-T buffer solution three times, ABTS One Component HRP Microwell Substrate (BioFX Laboratories, Inc.) was added thereto at 100 µl/well, and the binding affinity was detected as chromogenic reaction. Absorbance measurement employed an absorption microplate reader Sunrise R (Tecan Group Ltd.) to measure the absorbance at 415 nm. Top 16 phages having high binding affinity were analyzed for the DNA sequences of their polypeptide-encoding regions by the dideoxy method using ABI PRISM® 3100 (Applied Biosystems, Inc.). As a result, 13 phages each displaying a polypeptide comprising the amino acid sequence represented by SEQ ID NO: 8 and 3 phages exhibiting high sequence homology thereto were identified.

4) Preparation of N-Terminal Elongation Library

Subsequently, for the purpose of the stable conformation formation and high functionalization of a functional molecule by elongation in stages, a library was constructed in which the N terminus of the amino acid sequence (SEQ ID NO: 8) identified in the section 3) of Example 1 was elongated with an 8-residue-long random sequence $(Xaa)_8$ (FIG. 1).

First, a DNA (SEQ ID NO: 10) was designed which comprised a sequence in which restriction enzyme sites EcoRI and HindIII were added to a DNA region encoding the amino acid sequence represented by SEQ ID NO: 9 (in this context, the arbitrary natural amino acid residue Xaa is encoded by a mixed base triplet NNK; and in the sequence, N represents a mixed base A, C, G, or T, and K represents a mixed base G or T). Subsequently, two organically synthesized DNAs respectively consisting of the nucleotide sequences represented by SEQ ID NOs: 11 and 12 were purchased from Rikaken Co., Ltd., and these DNAs were used as templates in PCR to enzymatically synthesize and amplify the DNA of SEQ ID NO: 10. The PCR was carried out using KOD DNA polymerase (Toyobo Co., Ltd.) under reaction conditions that followed the attached manual.

According to similar procedures as in the section 1) of Example 1, the ligation of the amplified DNA to the T7 phage genomic DNA, the in vitro packaging of the phage, and the construction of a T7 phage display library were carried out. According to similar procedures as in the section 2) of Example 1, this phage library was used, and the "steps of: contacting the library with the Fc region; and selecting and recovering phages bound with this Fc region" were repeated six times to enrich the phages displaying polypeptides exhibiting binding affinity for the Fc region. According to similar procedures as in the section 3) of Example 1, molecules having binding affinity were subsequently confirmed from the enriched phage population by ELISA, followed by DNA sequence analysis by the dideoxy method. As a result of the DNA sequence analysis, a phage displaying a polypeptide comprising the amino acid sequence represented by SEQ ID NO: 13 with the convergence of the amino acid sequence confirmed (hereinafter, this phage is referred to as 2A1) was identified as a phage having binding affinity.

5) Binding Affinity Analysis of 2A1 Peptide

Subsequently, in order to confirm that the polypeptide displayed on the surface layer of the phage 2A1 was a novel molecule having binding affinity, the synthetic peptide consisting of the amino acid sequence represented by SEQ ID NO: 13 (hereinafter, this peptide is referred to as 2A1 peptide) was analyzed for its binding affinity by the surface plasmon resonance method.

Figure 2:
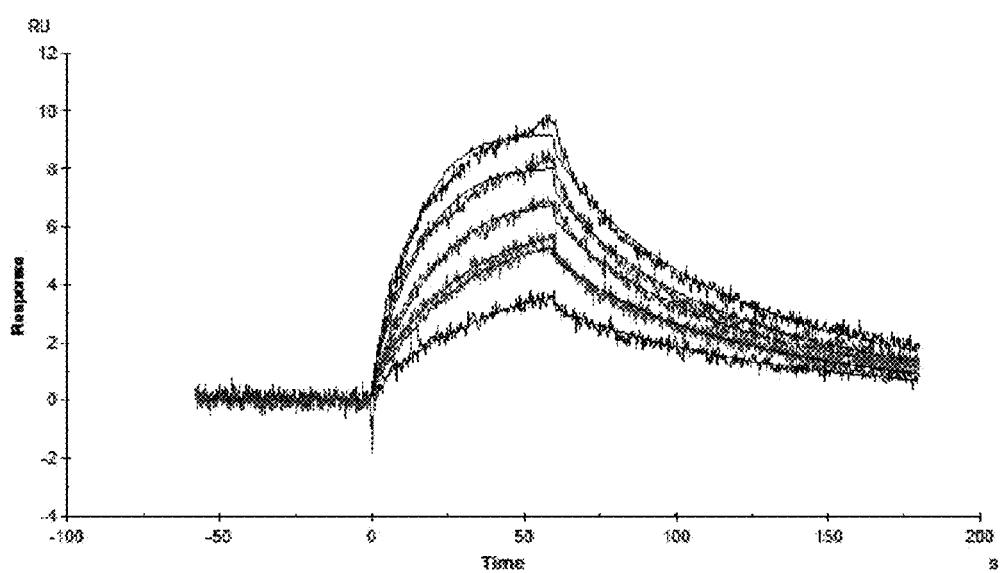
FIG. 2 shows results of the binding affinity analysis of 2A1 peptide for a human Fc region by surface plasmon resonance. The diagram depicts the binding curve of each 2A1 peptide diluted to a concentration of 100, 80, 60, 40, or 20 nM for Fc immobilized on a sensor chip.

The organically chemically synthesized 2A1 peptide was purchased from Bio-Synthesis Inc. The surface plasmon resonance measurement apparatus used was Biacore T100 (GE Healthcare Japan Corp.). A human Fc region manufactured by Jackson ImmunoResearch Laboratories, Inc. was immobilized onto a sensor chip CM5 (GE Healthcare Japan Corp.) by the amine coupling method using Amine Coupling Kit (GE Healthcare Japan Corp.). Subsequently, the 2A1 peptide was diluted to 100, 80, 60, 40, or 20 nM with an HBS-T buffer solution (10 mM HEPES, 150 mM NaCl, and 0.05% (v/v) Tween 20, pH 7.4), and each dilution was subjected to binding affinity analysis at a reaction temperature of 25° C. (FIG. 2). The measurement data was processed with Biacore T100 Evaluation Software (GE Healthcare Japan Corp.) to calculate the binding affinity as $K_D=2.2\times10^{-8}$ (M) in terms of equilibrium dissociation constant $K_D$, demonstrating its high binding affinity.

Subsequently, in order to analyze in detail the molecule-recognizing properties of the 2A1 peptide, the 2A1 peptide was immobilized onto a sensor chip CM5 by the amine coupling method and analyzed for its binding affinity for human IgG or an Fc region treated under a plurality of conditions shown below. The assay samples used were as follows: (1) a human Fc region manufactured by Jackson ImmunoResearch Laboratories, Inc., (2) undenatured human monoclonal IgG having a natural structure (Chugai Pharmaceutical Co., Ltd.), (3) an Fc region prepared from the IgG (2) (the Fc region was prepared by the papain digestion of the IgG according to the instruction manual attached to Pierce® Fab Preparation Kit (Thermo Fisher Scientific Inc.) followed by purification by affinity chromatography using MabSelect SuRe (GE Healthcare Japan Corp.), HiTrap DEAE anion-exchange chromatography (GE Healthcare Japan Corp.), and gel filtration chromatography using Superdex 200 (GE Healthcare Japan Corp.)), (4) acid-denatured IgG obtained by the treatment of the IgG (2) with an acidic buffer solution (20 mM sodium acetate, pH 4.5) at 50° C. for 10 days, and (5) an Fc region obtained by the reduction treatment of the Fc region (3) with 50 mM 2-mercaptoethylamine (Thermo Scientific Pierce) at 37° C. for 90 minutes.

Figure 3:
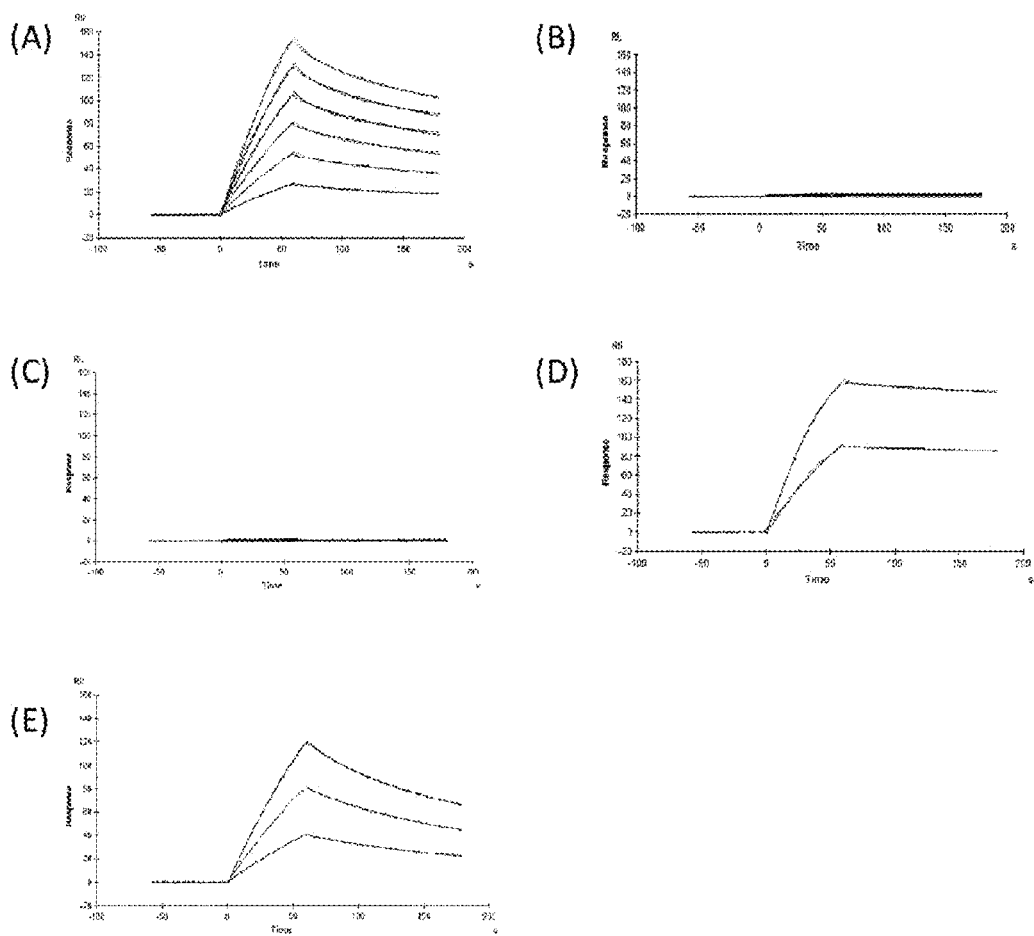
FIG. 3(A) shows results of the binding affinity analysis of 2A1 peptide for a human Fc region (Jackson ImmunoResearch Laboratories, Inc.) by surface plasmon resonance. The diagram depicts the binding curve of each human Fc region diluted to a concentration of 600, 500, 400, 300, 200, or 100 nM for the 2A1 peptide immobilized on a sensor chip.
FIG. 3(B) shows results of the binding affinity analysis of 2A1 peptide for natural human monoclonal IgG by surface plasmon resonance. The diagram depicts the binding curve of each natural IgG diluted to a concentration of 600, 500, 400, 300, 200, or 100 nM for the 2A1 peptide immobilized on a sensor chip.
FIG. 3(C) shows results of the binding affinity analysis of 2A1 peptide for a natural human Fc region by surface plasmon resonance. The diagram depicts the binding curve of each natural human Fc region diluted to a concentration of 600, 500, 400, 300, 200, or 100 nM for the 2A1 peptide immobilized on a sensor chip.
FIG. 3(D) shows results of the binding affinity analysis of 2A1 peptide for acid-denatured human IgG by surface plasmon resonance. The diagram depicts the binding curve of each acid-denatured human IgG diluted to a concentration of 250 or 125 nM for the 2A1 peptide immobilized on a sensor chip.
FIG. 3(E) shows results of the binding affinity analysis of 2A1 peptide for a reduced human Fc region by surface plasmon resonance. The diagram depicts the binding curve of each reduced human Fc region diluted to a concentration of 600, 400, or 200 nM for the 2A1 peptide immobilized on a sensor chip.

As a result of the surface plasmon resonance test, the 2A1 peptide binds to (1) the human Fc region purchased from Jackson ImmunoResearch Laboratories, Inc. (FIG. 3A), but does not exhibit binding to (2) the human IgG having a natural structure (FIG. 3B) or (3) the Fc region derived therefrom (FIG. 3C). On the other hand, the 2A1 peptide bound to each of (4) the acid-denatured IgG (FIG. 3D) with binding affinity of $K_D=2.2\times10^{-9}$ (M) and (5) the reduced Fc region (FIG. 3E) with binding affinity of $K_D=1.0\times10^{-7}$ (M). These results suggest that the 2A1 peptide does not recognize the natural structure of the Fc region, but rather specifically recognizes a nonnatural structure resulting from acid treatment or reduction treatment and/or thermal denaturation or the like and specifically distinguishes the nonnatural structure from the natural structure. This property is a function homogeneous to specific recognition ability achieved as a result of the sophisticated conformation of a protein consisting of a high-molecular-weight polypeptide typified by so-called "key and keyhole". The results described above demonstrated that although the 2A1 peptide comprising an 8-residue chignolin variant as a backbone is 25 residues long and is much smaller than the conventional protein backbone scaffolds (see Table 1), this peptide exhibits sufficient functionality, as with high-molecular-weight proteins, independently of cyclization.

6) Binding Affinity Analysis of H6 Peptide

In order to evaluate the effect of elongation in stages carried out for the purpose of the stable conformation formation and high functionalization of a functional molecule, the sequence obtained in the section 3) of Example 1 was evaluated for its properties. Specifically, a synthetic peptide consisting of the amino acid sequence represented by SEQ ID NO: 8 (hereinafter, this peptide is referred to as H6 peptide) was analyzed for its binding affinity by the surface plasmon resonance method.

Figure 4:
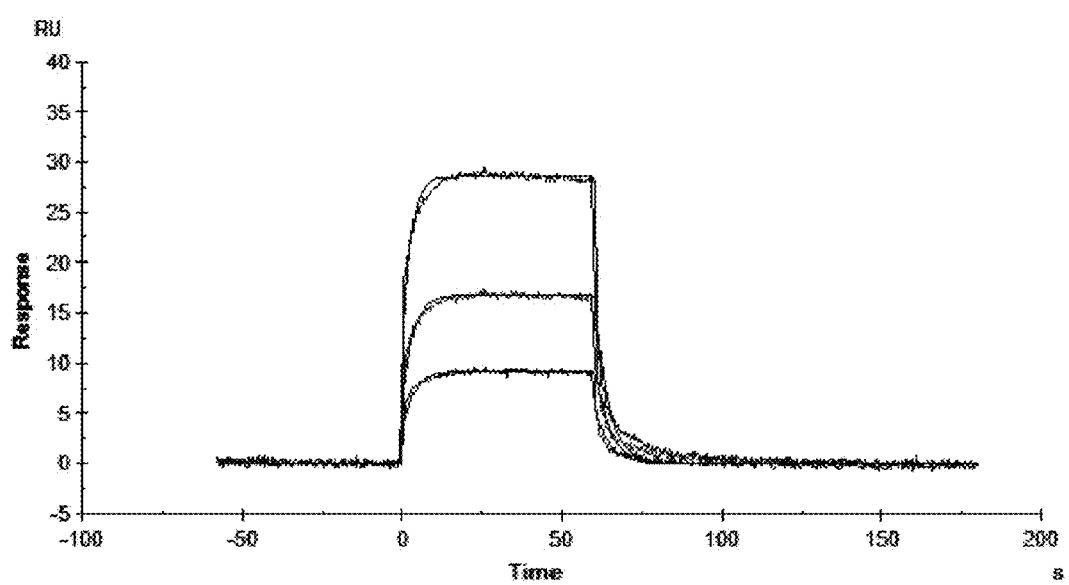
FIG. 4 shows results of the binding affinity analysis of H6 peptide for a human Fc region (Jackson ImmunoResearch Laboratories, Inc.) by surface plasmon resonance. The diagram depicts the binding curve of each H6 peptide diluted to a concentration of 50, 25, or 12.5 µM for the human Fc region immobilized on a sensor chip.

The organically chemically synthesized H6 peptide was purchased from Bio-Synthesis Inc. The surface plasmon resonance measurement apparatus used was Biacore T100 (GE Healthcare Japan Corp.). A human Fc region manufactured by Jackson ImmunoResearch Laboratories, Inc. was immobilized onto a sensor chip CM5 (GE Healthcare Japan Corp.) by the amine coupling method using Amine Coupling Kit (GE Healthcare Japan Corp.). Subsequently, the H6 peptide was diluted to 50, 25, or 12.5 µM with an HBS-T buffer solution (10 mM HEPES, 150 mM NaCl, and 0.05% (v/v) Tween 20, pH 7.4), and each dilution was subjected to binding affinity analysis at a reaction temperature of 25° C. (FIG. 4). The measurement data was processed with Biacore T100 Evaluation Software (GE Healthcare Japan Corp.) to calculate the binding affinity as $K_D=7.9\times10^{-5}$ (M) in terms of equilibrium dissociation constant $K_D$. This value revealed that the 2A1 peptide that underwent elongation in stages on the basis of the H6 peptide exhibits approximately 3600-fold improvement in affinity as a result of the elongation. These results demonstrated that functions can be improved in stages by the preparation of a molecular library by the addition in stages of an elongation region comprising a microprotein.

7) Binding Affinity Analysis of 2A1 Variant-Type Peptide

Figure 5:
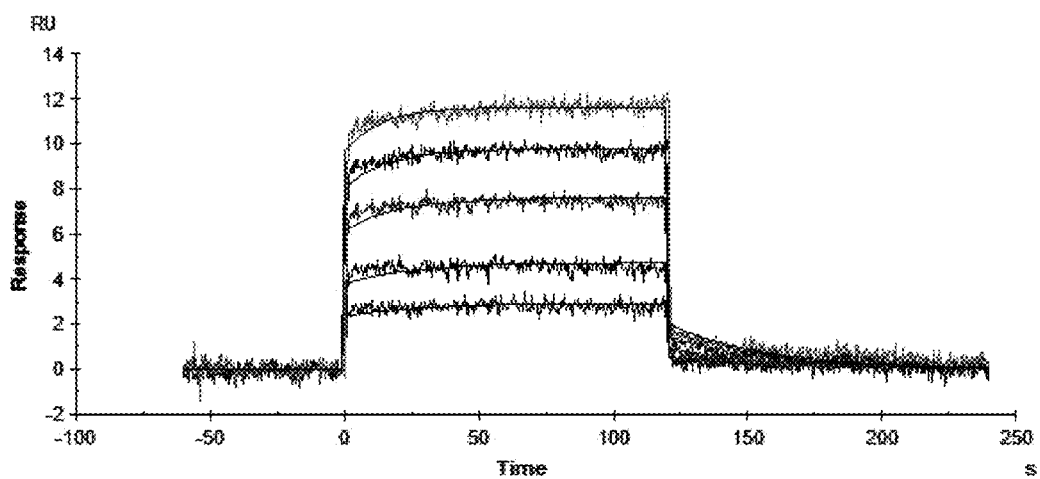
FIG. 5 shows results of the binding affinity analysis of 2A1Gly peptide for a human Fc region (Jackson ImmunoResearch Laboratories, Inc.) by surface plasmon resonance. The diagram depicts the binding curve of each 2A1Gly peptide diluted to a concentration of 40, 30, 20, 10, or 5 µM for the human Fc region immobilized on a sensor chip.

In this section, in order to examine the advantageous influence of the microprotein chignolin variant incorporated in the 2A1 peptide on the binding affinity as a function, an organically chemically synthesized variant-type peptide (2A1Gly peptide) consisting of the amino acid sequence represented by SEQ ID NO: 14 was purchased from Bio-Synthesis Inc. and evaluated for its binding affinity for a human Fc region manufactured by Jackson ImmunoResearch Laboratories, Inc. This variant-type peptide was derived from the 2A1 peptide by the replacement of the chignolin variant region (Tyr Asp Pro Arg Thr Gly Thr Trp) (SEQ ID NO: 71) incorporated therein with a glycine-rich linker (Gly Gly Gly Ser Gly Gly Gly Gly) (SEQ ID NO: 72). In general, a linker rich in glycine in its sequence is known to fail to maintain a particular structure due to its flexibility (References 43 and 44). Specifically, the binding affinity of this variant-type peptide can be evaluated to reveal the influence of the chignolin backbone on the functions exhibited by the 2A1 peptide. The binding affinity was evaluated by the surface plasmon resonance method using Biacore T100 in the same way as in the section 5) of Example 1. The variant-type peptide was adjusted to 40, 30, 20, 10, or 5 µM with an HBS-T buffer solution and analyzed for its binding affinity for the human Fc region (manufactured by Jackson ImmunoResearch Laboratories, Inc.) immobilized on a sensor chip CM5 by the amine coupling method in the same way as in the section 5) of Example 1 (FIG. 5). As a result, the variant-type peptide exhibited largely reduced binding affinity of $K_D=2.3\times10^{-5}$ (M) which was 1/1000 or less of that of the 2A1 peptide, demonstrating that the 2A1 peptide exhibits remarkable improvement in binding affinity by the incorporation of the microprotein chignolin variant.

8) Conformation Analysis of 2A1 Peptide

Figure 6:
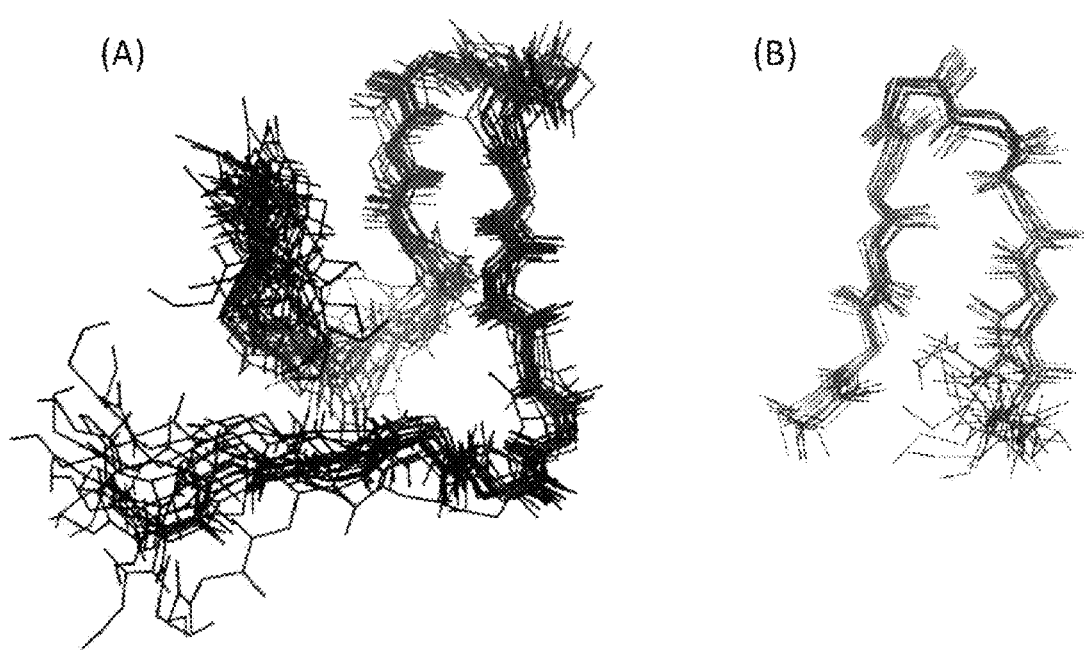
FIG. 6(A) shows the NMR structure of the 2A1 peptide.
FIG. 6(B) shows the NMR structure of the microprotein chignolin. The structure coordinate was obtained from Protein Data Bank (PDB code, 1UAO).

In order to demonstrate the incorporation of the microprotein chignolin variant was involved in the conformation formation of the 2A1 peptide, the 2A1 peptide was analyzed for its conformation by nuclear magnetic resonance (NMR). The 2A1 peptide was dissolved in a 10 mM acetic acid-d4 sodium buffer solution (pH 4.5) (Cambridge Isotope Laboratories, Inc.) containing 5% (v/v) $D_2O$ and 0.01% (v/v) sodium 2,2-dimethyl-2-silapentane-5-sulfonate to adjust its concentration to 1.8 mM. The 1H homonuclear NOESY-TOCSY spectral data was obtained using Bruker AMX 500, and 1H was attributed to all amino acid residues using an analysis program Sparky (Goddard T D and Kneller D G. SPARKY 3. University of California, San Francisco). Structural analysis was conducted by distance-restrained molecular dynamic calculation using CYANA-3.1 (Reference 45) to obtain a convergence structure having principal chain rmsd=1.51 angstroms (FIG. 6A).

As a result of NOESY, the long-range NOE between the tyrosine residue at position 9 and the tryptophan residue at position 16 attributed to the chignolin conformation was observed as obtained in the past. As a result of the structural calculation, 2A1 maintained a large portion of the β-hairpin structure of chignolin determined by NMR in the past (FIG. 6B) (Reference 4). Two regions respectively elongated from the N terminus and C terminus of the chignolin variant were spatially located closely to each other with respect to the core chignolin variant introduced as a microprotein. Its whole structure formed was similar to that of a spherical protein. Also, a plurality of bonds between residues were confirmed between the N-terminal and C-terminal regions. This indicates that the structure formation and structure stabilization of an obtained molecule are achieved by the elongation in stages of the amino acid sequence via the microprotein chignolin variant. In addition, the tryptophan residue at position 16 of the chignolin variant was buried so as to be surrounded by the C-terminal elongated region and was involved in the formation of a hydrophobic core similar to that of a spherical protein. These results of the structural analysis showed that the chignolin variant introduced as a protein backbone functions to stabilize the structure, and, together with the results of the binding affinity analysis of the variant 2A1Gly peptide in the section 6) of Example 1, demonstrated that the incorporation of the microprotein chignolin contributes to the formation of a stable conformation, thereby exhibiting remarkable improvement in binding affinity.

The novel polypeptide identified in this Example 1 is 25 residues long, and this size is remarkably small as compared with other protein backbones listed in Table 1 in Background Art. As shown in Table 1, short-chain polypeptides of less than dozens of residues usually need to be cyclized for structure stabilization. By contrast, the novel polypeptide identified here realized structure formation sufficient for the exhibition of its functions independently of cyclization, because its structure was stabilized by the introduction of a core microprotein of only 8 residues as a backbone. Specifically, this Example 1 demonstrated that the introduction of the microprotein is a rational approach of preparing a novel low-molecular-weight functional polypeptide and is effective.

The elongation in stages using random regions offers an efficient method for obtaining a novel molecule for use of existing display methods of libraries. This is because the essential problem of the existing display methods of libraries such as phage display and mRNA display methods is that these methods are physically limited by the sizes of the libraries and cannot completely cover long-chain random sequences. For example, the display methods at a laboratory scale allegedly yield, in principle, a library size of approximately $10^{14}$ at the maximum. By contrast, the random regions introduced in Example 1 were a total of 16 residues long, i.e., produce diversity of $20^{16}$, which require a library size of approximately $10^{20}$ for completely covering this diversity. This library size is very difficult to achieve at a usual laboratory scale. Thus, the elongation in stages using the microprotein and the random regions is rational to the efficient inclusion of diversity.

Example 2

This Example describes a method comprising preparing a polypeptide library of molecules containing a known particular sequence and a chignolin variant, and using this library to identify a novel polypeptide having enhanced binding affinity for an Fc region, which is a portion of a constant region of human immunoglobulin G (IgG). The library was prepared by a method involving adding a known particular sequence and a random sequence to a chignolin variant. Specifically, a library was prepared in which a 13-residue-long particular sequence known to have very low binding affinity for the target human IgG Fc region, and a 10 residue-long random sequence were added to the chignolin variant. A novel polypeptide having high binding affinity for the target was identified from this population.

1) Construction of C-Terminal Elongation Library and Identification of Affinity Polypeptide A cyclic peptide Fc III of 13 residues exhibiting binding affinity for the human IgG Fc region (Reference 46) reduces its binding affinity to 1/2000 or lower by losing disulfide cross-link by reduction treatment (Reference 47). A chignolin variant and a 10-residue-long random sequence $(Xaa)_{10}$ were added to variant FcIII-Ala peptide (Asp Ala Ala Trp His Leu Gly Glu Leu Val Trp Ala Thr) resulting from the replacement of the cysteine residue with an alanine residue to prepare a library.

For the construction of a C-terminal elongation library (FIG. 7), first, a DNA (SEQ ID NO: 16) was designed in which restriction enzyme sites EcoRI and HindIII were added to a DNA encoding the amino acid sequence of SEQ ID NO: 15 (in which the 10-residue-long random sequence $(Xaa)_{10}$ was added to the C terminus of a chignolin variant consisting of the amino acid sequence represented by SEQ ID NO: 3, the amino acid sequence of FcIII-Ala was added to the N terminus of the chignolin variant, and a 5-residue-long linker sequence Gly Gly Gly Gly Ser was further added to the N terminus thereof). In this context, the arbitrary natural amino acid residue Xaa is encoded by a mixed base triplet NNK. In the sequence, N represents a mixed base A, C, G, or T, and K represents a mixed base G or T. Subsequently, two organically synthesized DNAs respectively consisting of the nucleotide sequences represented by SEQ ID NOs: 17 and 18 were purchased from Rikaken Co., Ltd., and these DNAs were used in PCR to enzymatically synthesize and amplify the DNA of SEQ ID NO: 16. The PCR was carried out using KOD DNA polymerase (Toyobo Co., Ltd.) under reaction conditions that followed the attached manual. The amplified DNA was digested with restriction enzymes EcoRI and HindIII and then ligated to the 3' end of g10 gene on the T7 phage genomic DNA. The T7 phage genomic DNA used was a sample attached to T7Select 10-3 Cloning Kit (Novagen/Merck KGaA), and the procedures followed the attached T7Select® System Manual.

The ligated T7 phage genomic DNA was used in the in vitro packaging and amplification of the T7 phage using T7Select Packaging Kit (Novagen/Merck KGaA). These operational procedures followed similar procedures as in the section 1) of Example 1 to prepare a T7 phage display library composed of $1 \times 10^8$ clones.

Subsequently, use of the constructed T7 phage display library is shown in the steps of: contacting the library with the target substance human IgG Fc region; and selecting and recovering phages bound with the human IgG Fc region. The Fc region was prepared by the papain digestion of a human monoclonal antibody IgG (Chugai Pharmaceutical Co., Ltd.) according to the instruction manual attached to Pierce® Fab Preparation Kit (Thermo Fisher Scientific Inc. Pierce) followed by purification by affinity chromatography using MabSelect SuRe (GE Healthcare Japan Corp.), HiTrap DEAE anion-exchange chromatography (GE Healthcare Japan Corp.), and gel filtration chromatography using Superdex 200 (GE Healthcare Japan Corp.). The prepared Fc region was chemically biotinylated via an amino group using D-Biotinoyl-γ-Aminocaproic Acid N-Hydroxysuccinimide Ester (F. Hoffmann-La Roche, Ltd.) according to the attached instruction manual. According to similar procedures as in the sections 2) and 3) of Example 1, the steps of contacting the library with the Fc region and selecting and recovering phages bound therewith, the step of confirming phages displaying polypeptides having binding affinity by ELISA, and DNA sequence analysis by the dideoxy method were subsequently carried out. As a result, 4 phages respectively displaying polypeptides comprising the amino acid sequences represented by SEQ ID NOs: 19 to 22 were identified as phages displaying polypeptides exhibiting binding affinity. Hereinafter, the polypeptides displayed on these phage surface layers are respectively referred to as pep11 peptide (SEQ ID NO: 19), pep14 peptide (SEQ ID NO: 20), pep21 peptide (SEQ ID NO: 21), and pep24 peptide (SEQ ID NO: 22).

2) Binding Affinity Analysis of Identified Polypeptide

In this section, the polypeptides displayed on the surface layers of the identified 4 types of phages having binding affinity were prepared as synthetic peptides and analyzed for their functions by binding affinity analysis using surface plasmon resonance to examine improvement in the binding affinity of the particular sequence by the incorporation of the microprotein and the elongation region.

Figure 9:
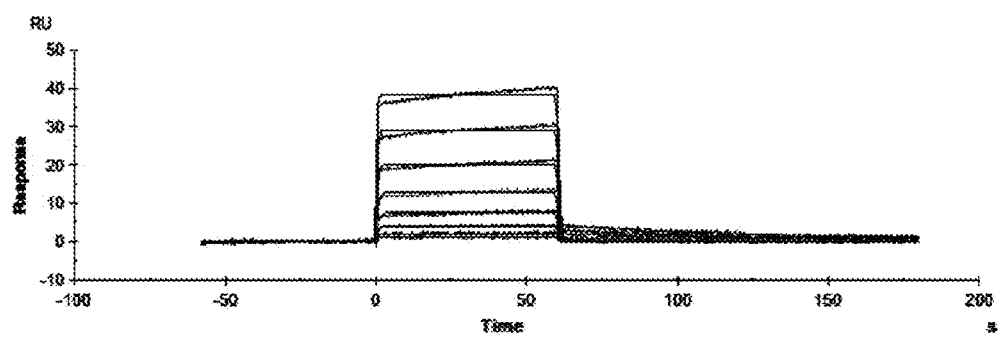
FIG. 9(A) shows results of the binding affinity analysis of FcIII-Ala peptide for a human Fc region by surface plasmon resonance. The diagram depicts the binding curve of each FcIII-Ala peptide diluted to a concentration of 100, 50, 25, 12.5, 6.25, 3.13, 1.56, or 0.78 μM for the human Fc region immobilized on a sensor chip.
FIG. 9(B) shows a Scatchard plot derived from the binding curve of the FcIII-Ala peptide for the human Fc region.
Figure 9:
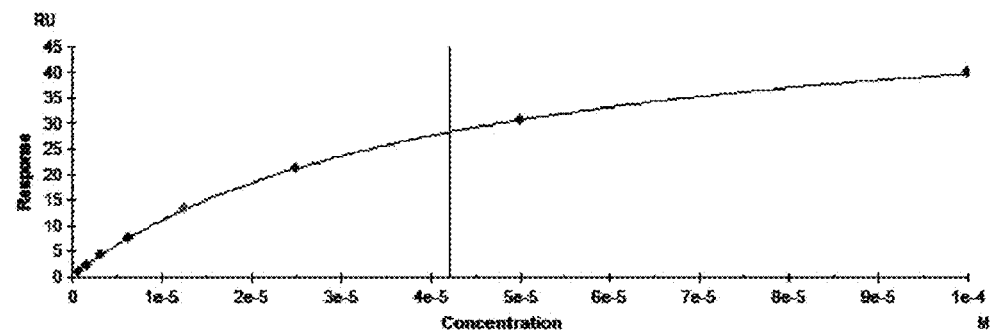
Figure 10:
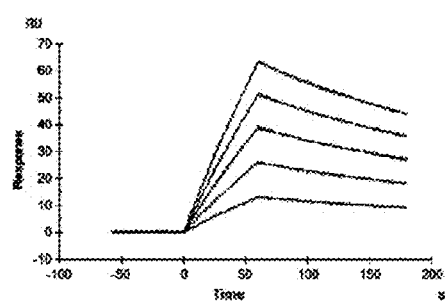
FIG. 10(A) shows results of the binding affinity analysis of a thioredoxin fusion protein Trx-p2 for a human Fc region by surface plasmon resonance. The diagram depicts the binding curve of each thioredoxin fusion protein Trx-p2 diluted to a concentration of 20, 16, 12, 8, or 4 nM for the human Fc region immobilized on a sensor chip.
FIG. 10(B) shows results of the binding affinity analysis of a thioredoxin fusion protein Trx-p5 for a human Fc region by surface plasmon resonance. The diagram depicts the binding curve of each thioredoxin fusion protein Trx-p5 diluted to a concentration of 20, 16, 12, 8, or 4 nM for the human Fc region immobilized on a sensor chip.
FIG. 10(C) shows results of the binding affinity analysis of a thioredoxin fusion protein Trx-p14 for a human Fc region by surface plasmon resonance. The diagram depicts the binding curve of each thioredoxin fusion protein Trx-p14 diluted to a concentration of 20, 16, 12, 8, or 4 nM for the human Fc region immobilized on a sensor chip.
FIG. 10(D) shows results of the binding affinity analysis of a thioredoxin fusion protein Trx-p17 for a human Fc region by surface plasmon resonance. The diagram depicts the binding curve of each thioredoxin fusion protein Trx-p17 diluted to a concentration of 20, 16, 12, 8, or 4 nM for the human Fc region immobilized on a sensor chip.
Figure 10:
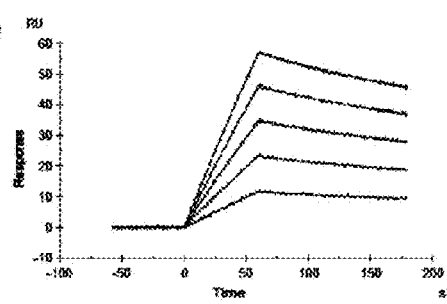
Figure 10:
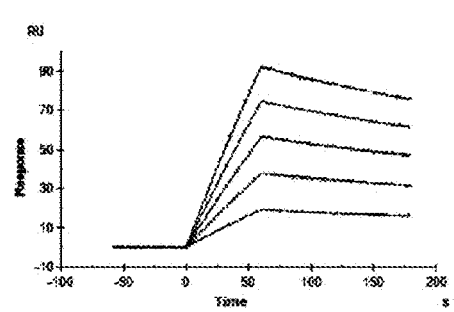
Figure 10:
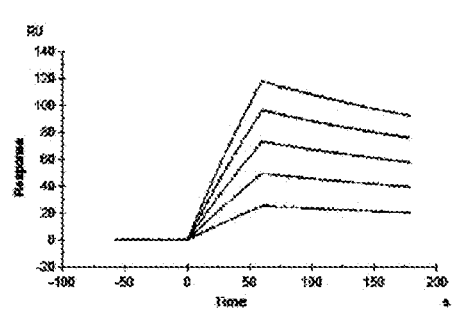

The pep11 peptide, the pep14 peptide, the pep21 peptide, the pep24 peptide, and the FcIII-Ala peptide (Asp Ala Ala Trp His Leu Gly Glu Leu Val Trp Ala Thr), which was the particular sequence before the addition of the microprotein, were purchased as synthetic peptides from Bio-Synthesis Inc. These peptides were each diluted with an HBS-T buffer solution to adjust the concentrations of the pep11 peptide, the pep14 peptide, the pep21 peptide, and the pep24 peptide to 500, 400, 300, 200, or 100 nM and the concentration of the FcIII-Ala peptide to 100, 50, 25, 12.5, 6.25, 3.13, 1.56, or 0.78 μM. The surface plasmon resonance test employed Biacore T100 (GE Healthcare Japan Corp.). The Fc region prepared in the section 1) of Example 2 was immobilized onto a sensor chip CM5 (GE Healthcare Japan Corp.) by the amine coupling method. The prepared synthetic peptides were used in binding affinity analysis (FIGS. 8A to 8D) to measure the equilibrium dissociation constants of the pep11 peptide, the pep14 peptide, the pep21 peptide, the pep24 peptide, and the FcIII-Ala peptide. The equilibrium dissociation constant of the FcIII-Ala peptide was obtained by a Scatchard plot using an equilibrium value, because its binding affinity is significantly low (FIGS. 9A and 9B). The data was processed using Biacore T100 Evaluation Software (GE Healthcare Japan Corp.) to calculate the equilibrium dissociation constants $K_D$ of $5.1 \times 10^{-7}$ (M), $1.2 \times 10^{-7}$ (M), $1.0 \times 10^{-7}$ (M), $2.2 \times 10^{-7}$ (M), and $4.2 \times 10^{-5}$ (M) for the pep11 peptide, the pep14 peptide, the pep21 peptide, the pep24 peptide, and the FcIII-Ala peptide, respectively. As a result, the most strongly binding pep21 peptide exhibited approximately 420-fold improvement in affinity as compared with the FcIII-Ala peptide used as the unelongated particular sequence.

This Example 2 shows that the incorporation of the microprotein chignolin variant as a backbone is also effective for the high functionalization of the particular functional amino acid sequence. The design of a molecular library in which a microprotein is incorporated in a particular sequence enhances the performance of the functional peptide, as a matter of course, and enables effective exploitation of even existing amino acid sequences that have not been sufficiently exploited due to their low functionality. This approach permits for modification to novel highly functional molecules on the basis of previously accumulated functional peptides.

As in Example 1, the polypeptides identified in Example 2 as molecules having binding affinity are polypeptides classified into polypeptides very small in size compared with the protein backbones shown in Table 1. Since the 9-residue microprotein chignolin variant is used as a backbone, these polypeptides, albeit 32 residues long, can exhibit their functions independently of cyclization.

Example 3

This Example shows a successful example of higher functionalization by the combination of the method shown in Example 1 and the method shown in Example 2. Specifically, a novel highly functionalized molecule having very high binding affinity for the target human IgG Fc region was identified by the further application of the "method involving elongation in stages to sequentially add random sequences" shown in Example 1 to the polypeptides identified from the "molecular library containing a known particular sequence and a microprotein" shown in Example 2. Also, this highly functionalized molecule was separately synthesized as a fusion protein bound with another protein and further analyzed for its properties.

1) Construction of N-Terminal Elongation Library and Identification of Affinity Polypeptide First, an N-terminal elongation library was prepared in which a chignolin variant (SEQ ID NO: 4) and a 10-residue-long random sequence $(Xaa)_{10}$ were added to the N terminus of each of the four amino acid sequences pep11 peptide, pep14 peptide, pep21 peptide, pep24 peptide identified in the section 1) of Example 2 (FIG. 7).

DNAs (SEQ ID NO: 27 to 30) were each designed in which restriction enzyme sites EcoRI and HindIII were added to DNAs respectively encoding the amino acid sequences represented by SEQ ID NOs: 23 to 26. Subsequently, each organically synthesized DNA (Rikaken Co., Ltd.) consisting of the nucleotide sequences represented by SEQ ID NOs: 31, 32, and 33, SEQ ID NOs: 31, 32, and 34, SEQ ID NOs: 31, 32, and 35, or SEQ ID NOs: 31, 32, and 36 was used in PCR to synthesize and amplify the 4 types of DNAs (SEQ ID NOs: 27 to 30). The PCR was carried out using KOD DNA polymerase (Toyobo Co., Ltd.) under reaction conditions that followed the attached manual. Each amplified DNA was digested with restriction enzymes EcoRI and HindIII and then ligated to the 3' end of g10 gene on the T7 phage genomic DNA. The T7 genome used was a sample attached to T7Select 10-3b (Novagen/Merck KGaA), and the procedures followed the attached T7Select® System Manual. The ligated T7 phage genome was used in the in vitro packaging and amplification of the T7 phage. The experimental procedures followed similar procedures as in the section 1) of Example 1 to prepare a T7 phage display library composed of $3 \times 10^8$ clones. The "steps of contacting the library with the Fc region and selecting and recovering phages bound therewith" followed similar procedures as in the section 1) of Example 2 and were repeated 10 times. The binding affinity test by ELISA and the DNA sequence analysis followed similar procedures as in the section 1) of Example 2. In this way, phages displaying, on their surface layers, polypeptides respectively comprising four amino acid sequences designated as p2 (SEQ ID NO: 37), p5 (SEQ ID NO: 38), p14 (SEQ ID NO: 39), and p17 (SEQ ID NO: 40) were identified as phages having binding affinity. These 4 types of polypeptides all had the sequence of the pep24 peptide at their C termini.

2) Expression and Binding Affinity Analysis of Thioredoxin Fusion Protein

This section shows an example of the intracellular expression and preparation of the polypeptides identified in the section 1) of Example 3 in the form of fusion proteins. The expression in the form of fusion proteins allows novel polypeptides to be stably expressed in cells irrespective of their physical properties. In addition, the linkage to an arbitrary protein also allows the functions of the novel polypeptide and the arbitrary protein to be included in one molecule. This section employed thioredoxin as one example of the protein to be linked, and shows an example of the expression of fusion proteins of this protein and the polypeptides identified in the section 1) of Example 3 in *E. coli*.

The T7 phage DNAs comprising the DNAs encoding the amino acid sequences of the four types of polypeptides, p2, p5, p14, and p17, identified in the section 1) of Example 3 were used as templates in PCR. The amplified DNAs were each digested with EcoRI and HindIII and introduced to a region of pET-48b (Invitrogen Corp) digested at its EcoRI/HindIII site to construct expression vectors for the four types of fusion proteins in which the identified polypeptides were linked to the C terminus of thioredoxin (hereinafter, these fusion proteins of the identified polypeptides with thioredoxin are referred to as Trx-p2, Trx-p5, Trx-p14, and Trx-p17 (SEQ ID NOs: 41 to 44), respectively). An E. coli BL21 (DE3) strain (Novagen/Merck KGaA) was transformed with each of the constructed expression vectors. This strain was subcultured in 200 ml of a 2×YT medium and shake-cultured until O.D. 600 around 0.8. The protein expression was induced by the addition of 1 mM (final concentration) isopropyl-β-thiogalactopyranoside (IPTG), followed by culture at 37° C. for 12 hours. The bacterial cells were recovered by centrifugation at 5000×g for 20 minutes and suspended in a buffer solution (20 mM Tris-HCl and 500 mM NaCl, pH 7.4). The bacterial cells were sonicated by Astrason Model S3000 (Wakenyaku Co., Ltd.), and an intracellular soluble fraction was recovered by centrifugation at 14000×g for 20 minutes. This soluble fraction was purified by metal chelate affinity chromatography using Ni Sepharose® 6 Fast Flow (GE Healthcare Japan Corp.) to prepare the thioredoxin fusion proteins of interest. The protein yields per litter of the medium (mg/L) were as high as 41, 43.6, 73.6, and 78.3 (mg/L) for Trx-p2, Trx-p5, Trx-p14, and Trx-p17, respectively, showing that the novel polypeptides identified in this Example 2 characterized in that the microprotein is incorporated therein can be stably expressed in the form of fusion proteins in cells.

Subsequently, an example of binding affinity analysis by the surface plasmon resonance method is shown as to the functions of the thioredoxin fusion proteins with the prepared polypeptides. The analysis apparatus used was Biacore T100 (GE Healthcare Japan Corp.). The Fc region prepared according to similar procedures as in the section 1) of Example 2 was immobilized onto a sensor chip CM5 (GE Healthcare Japan Corp.) by the amine coupling method. Subsequently, the prepared 4 thioredoxin fusion proteins (Trx-p2, Trx-p5, Trx-p14, and Trx-p17) were each adjusted to 20, 16, 12, 8, or 4 nM with an HBS-T buffer solution and subjected to binding affinity analysis at 25° C. (FIGS. 10A to 10D). The data was processed with Biacore T100 Evaluation Software (GE Healthcare Japan Corp.). The binding dissociation constants $K_D$ of Trx-p2, Trx-p5, Trx-p14, and Trx-p17 were calculated to be $K_D=2.4\times10^{-8}$ (M), $K_D=1.4\times10^{-8}$ (M), $K_D=8.8\times10^{-9}$ (M), and $K_D=7.8\times10^{-9}$ (M), respectively.

The results of the expression in E. coli and the quantitative binding affinity analysis revealed that the polypeptides with the microprotein incorporated therein, even when linked to thioredoxin in the fusion proteins, have high expression yields and high binding affinity without losing the high solubility of thioredoxin and the affinity of the identified polypeptides. This indicates that by appropriate linkage to an arbitrary protein as fusion proteins, the polypeptides with the microprotein incorporated therein can include both the properties of the arbitrary protein and the polypeptides in one molecule, and also supports the evidence that also exhibit sufficient functions in the "molecular library wherein each member is a fusion protein" as shown in claim 6.

3) Preparation of Identified Polypeptide by Protease Treatment of Fusion Protein, and Binding Affinity Analysis This section shows an example in which a polypeptide comprising the region identified as a polypeptide having binding affinity in the section 1) of Example 3 was prepared from the thioredoxin fusion protein and analyzed for its binding affinity by surface plasmon resonance.

As for Trx-p17 that exhibited the highest binding affinity in the section 2) of Example 3, the thioredoxin moiety was removed to prepare the polypeptide. Since the thioredoxin fusion protein produced by the expression vector pET-48b (Novagen/Merck KGaA) has an HRV 3C protease cleavage site in its amino acid sequence, the polypeptide of interest linked to the C terminus can be obtained using this protease.

In order to remove as much as possible redundant amino acid sequences located close to the protease cleavage site, a DNA (SEQ ID NO: 46) encoding a novel thioredoxin fusion protein represented by the amino acid sequence of SEQ ID NO: 45 was synthesized by PCR (this novel thioredoxin fusion protein was derived from Trx-p17 by the removal of the amino acid sequence Tyr Gln Asp Pro Asn Ser Gly Gly Gly Gly Ser (SEQ ID NO: 73) between thioredoxin and p17), and this DNA was transferred to an expression vector pET-48b (Novagen/Merck KGaA). According to similar procedures as in the section 2) of Example 3, this expression vector was used to prepare a thioredoxin fusion protein. The thioredoxin fusion protein (40 mg) was subjected to digestion reaction with 100 units of HRV 3C Protease (Novagen/Merck KGaA) at 4° C. The reaction conditions followed the attached manual. The reaction product was diluted with a 6 M guanidine hydrochloride solution and purified by gel filtration chromatography using Superdex Peptide 10/300 GL (GE Healthcare Japan Corp.) and subsequently reverse-phase chromatography using µRPC C2/C18 ST 4.6/100 (GE Healthcare Japan Corp.). The purified polypeptide is newly designated as p17_2 peptide (SEQ ID NO: 47), because this polypeptide contains 3 amino acid residues (Gly, Pro, and Gly) at the N terminus of the amino acid sequence of p17.

Figure 11:
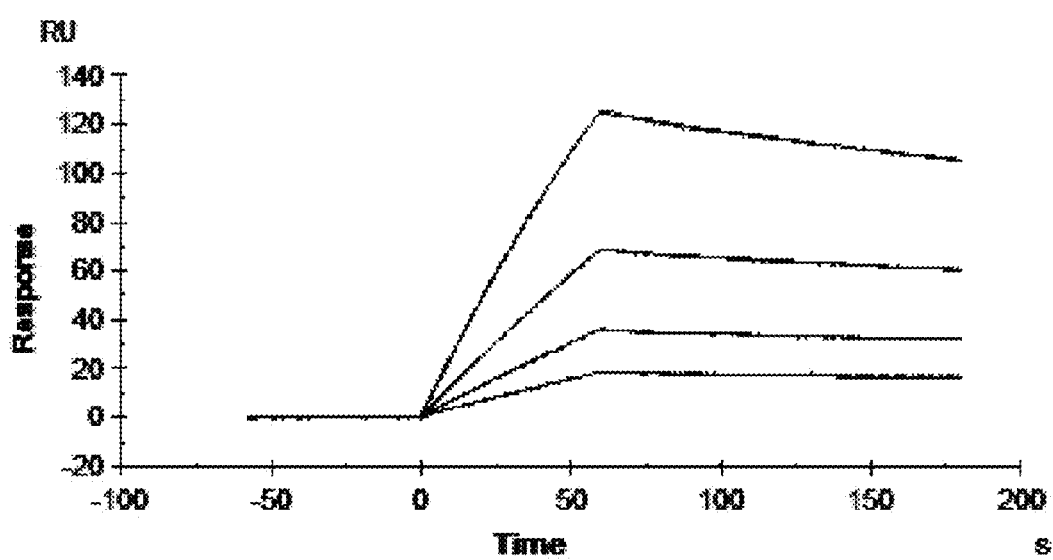
FIG. 11 shows results of the binding affinity analysis of p17_2 peptide for a human Fc region by surface plasmon resonance. The diagram depicts the binding curve of each p17_2 peptide diluted to a concentration of 25, 12.5, 6.25, or 8.13 nM for the human Fc region immobilized on a sensor chip.

Subsequently, the prepared p17_2 peptide was analyzed for its binding affinity by surface plasmon resonance. The assay employed Biacore T100 (GE Healthcare Japan Corp.). The p17_2 peptide was diluted with HBS-T to adjust its concentration to 25, 12.5, 6.25, or 3.13 nM. The immobilization of the Fc region onto a sensor chip CM5 and the binding affinity analysis were carried out according to similar procedures as in the section 2) of Example 2. As a result of the analysis (FIG. 11), p17_2 bound to the Fc region with binding affinity of equilibrium dissociation constant $K_D=1.6\times10^{-9}$ (M), and this value was 138-fold improvement and approximately 26000-fold improvement in binding affinity compared with the pep24 peptide and the FcIII-Ala peptide initially used as the particular sequence, respectively.

The p17_2 peptide prepared in Example 3 is 54 residues long, and this size is found as small as the smallest class of protein backbones having no cyclic backbone as shown in Table 1. The regions randomized in Examples 2 and 3 for obtaining p17_2 have a total of 20 residues, and this range of the randomized regions is sufficiently large, as compared with the protein backbones of 50 to 100 residues in Table 1. This is because the two microproteins introduced as backbones each consist of only 9 residues and also because regions other than the backbones can be sufficiently exploited as randomized regions. Because of these sufficiently randomized regions, the resulting library can create high molecular diversity, and the prepared p17_2 peptide realized high affinity (equilibrium dissociation constant $K_D=1.6\times10^{-9}$ (M)) for the target comparable to the strong antibody-antigen interaction.

In Examples 2 and 3, 190 times higher affinity for the target Fc region as a result of one-stage elongation and 138 times higher affinity for the target as a result of two-stage elongation were achieved by the elongation in stages of the particular sequence with the amino acid sequence consisting of the microprotein and the randomized region. The results described above demonstrated that high functionalization can be achieved in succession through the conformation stabilization of the molecule and/or its multivalent binding effect on the target by the repetitive addition in stages of microprotein-containing random sequences.

Example 4

This Example shows an example in which binding affinity was measured by surface plasmon resonance for each of variants (SEQ ID NOs: 51 to 57) mutagenized at an amino acid residue from the 2A1 peptide consisting of the amino acid sequence represented by SEQ ID NO: 13 to evaluate the influence of each amino acid residue on the binding affinity.

Seven types of organically chemically synthesized variant peptides, 2A1_Q5R (SEQ ID NO: 51), 2A1_W6A (SEQ ID NO: 52), 2A1_S7A (SEQ ID NO: 53), 2A1_R17A (SEQ ID NO: 54), 2A1_S18A (SEQ ID NO: 55), 2A1_S19A (SEQ ID NO: 56), and 2A1_I20A (SEQ ID NO: 57), were purchased from Bio-Synthesis Inc. The surface plasmon resonance measurement apparatus used was Biacore T100 (GE Healthcare Japan Corp.). A human Fc region having a nonnatural structure was prepared by the dialysis of a natural human Fc region against a glycine-HCl buffer solution (10 mM glycine-HCl, and 150 mM NaCl, pH 2.0). This nonnatural human Fc region was immobilized onto a sensor chip CM5 (GE Healthcare Japan Corp.) by the amine coupling method using Amine Coupling Kit (GE Healthcare Japan Corp.). Subsequently, each peptide was diluted to 62.5, 31.3, or 15.6 nM for 2A1_Q5R, 500, 250, or 125 nM for 2A1_W6A, 1000, 500, or 250 nM for 2A1_S7A, 500, 250, or 125 nM for 2A1_R17A, 125, 62.5, or 31.3 nM for 2A1_S18A, 1000, 500, or 250 nM for 2A1_S19A, and 500, 250, or 125 nM for 2A1_I20A with an HBS-T buffer solution (10 mM HEPES, 150 mM NaCl, and 0.05% Tween 20®, pH 7.4) and subjected to binding affinity measurement at a reaction temperature of 25° C.

The measurement data was processed with Biacore T100 Evaluation Software (GE Healthcare Japan Corp.) to calculate the respective binding dissociation constants $K_D$ of 2A1_Q5R, 2A1_W6A, 2A1_S7A, 2A1_R17A, 2A1_S18A, 2A1_S19A, and 2A1_I20A (Table 2). The results revealed that the mutation of the glutamine residue at position 5 to an arginine residue elevates the binding activity by 2.5 times. Also, amino acid residues that largely decreased binding affinity by mutation to an alanine residue were identified, and reduction in binding affinity was observed for the tryptophan residue at position 6 (approximately 1/8), the serine residue at position 7 (approximately 1/5), the arginine residue at position 17 (approximately 1/16), the serine residue at position 19 (approximately 1/10), and the isoleucine residue at position 20 (approximately 1/50). These results show that these residues are largely involved in binding affinity.

TABLE 2

Table 2. Binding dissociation constant of 2A1 variant

| Variant | $K_D$ (nM) | SEQ ID NO |
|---|---|---|
| 2A1_Q5R | 8.7 | 51 |
| 2A1_W6A | 180 | 52 |
| 2A1_S7A | 110 | 53 |
| 2A1_R17A | 350 | 54 |
| 2A1_S18A | 23 | 55 |
| 2A1_S19A | 220 | 56 |
| 2A1_I20A | 920 | 57 |

Example 5

This Example shows an example of the recovery of the target human IgG Fc region from a solution containing foreign proteins in order to evaluate the binding specificity of the 2A1 peptide consisting of the amino acid sequence represented by SEQ ID NO: 13.

The 2A1 peptide (0.5 mg) was dissolved in 1.5 ml of a sodium carbonate buffer solution (0.2 M NaHCO$_3$, and 0.5 M NaCl, pH 8.3), and this solution was immobilized onto 0.1 ml of NHS-activated Sepharose® (GE Healthcare Japan Corp.) by the amine coupling method. The immobilization procedures followed the attached document. The immobilization produced a reaction rate of 42%. The solution containing foreign proteins used was a supernatant obtained by: suspending an E. coli BLT5403 strain cultured in 1 ml of an LB medium in 1 ml of a TBS-T buffer solution (50 mM Tris-HCl, 150 mM NaCl, and 0.05% (w/v) Tween 20®, pH 7.4); and sonicating the suspension, followed by centrifugation. A human Fc region having a nonnatural structure was prepared by the dialysis of a natural human Fc region against a glycine-HCl buffer solution (10 mM glycine-HCl, and 150 mM NaCl, pH 2.0). This nonnatural Fc region (corresponding to 5 μg) was added to 62 μl of the E. coli lysate, and this mixture was diluted to 1 ml with a TBS-T buffer solution. The resulting solution was used as a sample solution for binding specificity evaluation. An E. coli lysate containing no nonnatural Fc region was prepared as a control solution for a comparative test.

Figure 12:
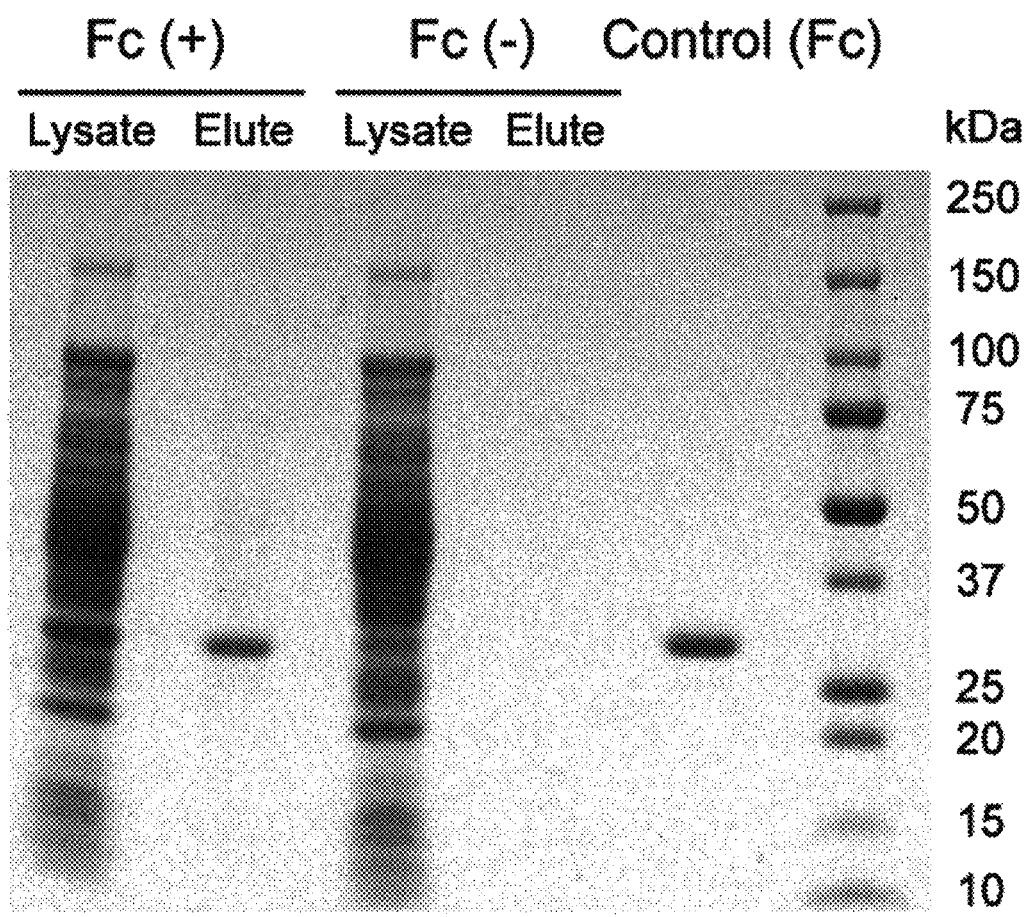
FIG. 12 shows results of binding specificity evaluation using a 2A1 peptide-immobilized resin. The diagram depicts results of the SDS polyacrylamide gel electrophoresis of a sample solution (Lysate) and an eluate (Elute) in the presence and absence of a nonnatural Fc region (Fc(+) and Fc(−), respectively). Control depicts the band of the Fc region.

The prepared sample solution was mixed with the 2A1 peptide-immobilized Sepharose for 20 minutes. Then, the mixture was washed with 0.5 ml of a TBS-T buffer solution five times, followed by elution with 0.2 ml of 50 mM NaOH. The eluate was neutralized with 10 μl of 3 M sodium acetate (pH 5.2). The eluate and the sample solution were analyzed by SDS polyacrylamide gel electrophoresis (FIG. 12). Only a band corresponding to the Fc region was significantly present in the eluate, as compared with other foreign proteins. These results show that the polypeptide 2A1 specifically recognizes the target Fc region from among many foreign proteins, and show that the molecule obtained according to the present invention has high target specificity as seen in usual protein-protein interaction.

Example 6

This Example shows an example in which the 2A1 peptide consisting of the amino acid sequence represented by SEQ ID NO: 13 was evaluated for its resistance to thermal deactivation. The organically synthesized 2A1 peptide was diluted to 27 μM with an HBS-T buffer solution (10 mM HEPES, 150 mM NaCl, and 0.05% Tween 20®, pH 7.4), and this dilution was heated at 100° C. for 15 minutes. The heat-treated sample and a non-heat-treated sample were each diluted to 125, 62.5, or 31.2 nM with an HBS-T buffer solution and evaluated for their binding affinity by surface plasmon resonance.

Figure 13:
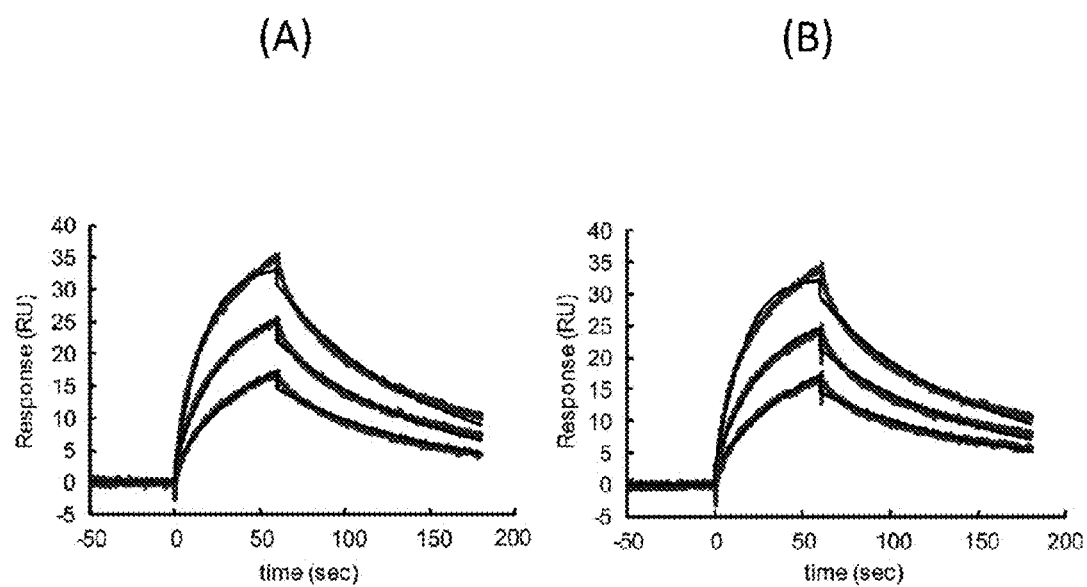
FIG. 13 shows results of an SPR test using a 2A1 peptide solution before 100° C. heat treatment (A) and after the treatment (B).

The surface plasmon resonance measurement apparatus used was Biacore T100 (GE Healthcare Japan Corp.). A human Fc region having a nonnatural structure used was prepared by the dialysis of a natural human Fc region against a glycine-HCl buffer solution (10 mM glycine-HCl, and 150 mM NaCl, pH 2.0). This nonnatural Fc region was immobilized onto a sensor chip CM5 (GE Healthcare Japan Corp.) by the amine coupling method using Amine Coupling Kit (GE Healthcare Japan Corp.) and subjected to binding affinity measurement at a reaction temperature of 25° C. (FIG. 13). The measurement data was processed with Biacore T100 Evaluation Software (GE Healthcare Japan Corp.). The binding affinity of the heat-treated and non-heat-treated samples was calculated to be $2.0 \times 10^{-8}$ (M) and $2.2 \times 10^{-8}$ (M), respectively, in terms of binding dissociation constant $K_D$. The total amount of binding responses was also identical between the samples. These results show that the binding affinity of the 2A1 peptide is not irreversibly impaired even by heat treatment, and show that this peptide has high resistance to thermal deactivation. Such high resistance to thermal deactivation is a property characteristic of the reversible denaturation and regeneration of small proteins, showing that the small protein obtained according to the present invention is more highly convenient than giant proteins, such as an antibody IgG, which generate irreversible denaturation and aggregates by heat treatment.

Example 7

This Example shows an example of a competitive evolution experiment that demonstrated that the molecular library (SEQ ID NO: 9) containing the microprotein in each amino acid sequence comprises a larger number of molecules having high binding affinity than that of a molecular library (SEQ ID NO: 58) containing an amino acid sequence having no particular structure as a substitute for the microprotein.

A phage library displaying a molecular library consisting of the amino acid sequence of SEQ ID NO: 58 on the T7 bacteriophage surface layers was constructed as the molecular library containing an amino acid sequence having no particular structure. This molecular library has the same amino acid sequence as that of the molecular library of SEQ ID NO: 9 except that its amino acid sequence has a glycine-rich linker (Gly Gly Gly Ser Gly Gly Gly Gly) containing many glycine residues, as a substitute for the microprotein. In general, a polypeptide rich in glycine is known to fail to maintain a particular structure due to its structural flexibility (References 43 and 44).

First, a DNA (SEQ ID NO: 59) was designed which comprised a sequence in which restriction enzyme sites EcoRI and HindIII were added to a DNA region encoding the amino acid sequence represented by SEQ ID NO: 58 (in this context, the arbitrary natural amino acid residue Xaa is encoded by a mixed base triplet NNK; and in the sequence, N represents a mixed base A, C, G, or T, and K represents a mixed base G or T). According to similar procedures as in the section 4) of Example 1, this designed DNA was enzymatically synthesized and amplified by PCR.

According to similar procedures as in the section 1) of Example 1, the ligation of the amplified DNA to the T7 phage genomic DNA, the in vitro packaging of the phage, and the construction of a T7 phage display library were carried out. In this context, the phage library displaying the polypeptides containing the microprotein in their amino acid sequences as shown in SEQ ID NO: 9 is referred to as a CLN library, and a phage library displaying the polypeptides containing the glycine-rich linker in their amino acid sequences as shown in SEQ ID NO: 58 is referred to as a Gly library. After the in vitro packaging, the CLN library and the Gly library were constituted by $1.7 \times 10^8$ clones and $1.6 \times 10^8$ clones, respectively.

Figure 14:
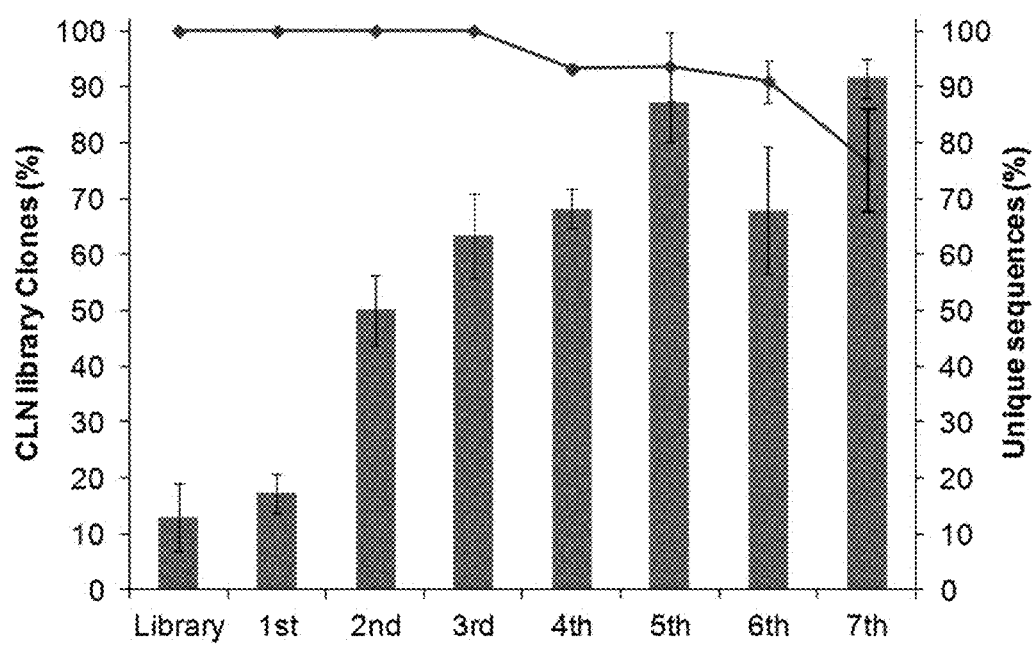
FIG. 14 shows results of a competitive evolution experiment. The diagram shows the ratios of a mixed library before function selection and a CLN library-derived clone in a molecule population after each round of the selection step (bar graph) and the ratio of a clone having an independent amino acid sequence (line graph). Sequence determination was carried out for a total of 48 clones (3 rounds each involving 16 clones).

The CLN library and the Gly library were mixed at a ratio of 1:10 in terms of phage titer (plaque forming unit, pfu). This mixed library was used in selection for a human IgG Fc region. The steps of: contacting the library with the target substance Fc region; and selecting and recovering bound phages followed similar procedures as in the section 2) of Example 1 and were repeated 7 times. Arbitrary 48 clones were isolated from each of the mixed library and a molecule population obtained after each of the seven rounds of the steps. The DNA sequences of the regions encoding the displayed polypeptides were analyzed on a 16-clone basis by the dideoxy method using ABI PRISM® 3100 (Applied Biosystems, Inc.) to calculate the ratio of a clone derived from the CLN library and the ratio of a clone having an independent amino acid sequence (FIG. 14). The ratio of a CLN library-derived clone initially set to 10% was increased with increase in the number of rounds of selection for the Fc region. The independency of the clone sequence exhibited 70% or more even after the 7 repetitive rounds of the steps. This indicates that a plurality of clones having high binding affinity were present as a molecule population, not that one type of clone was accidentally selected as a high-affinity clone. Thus, the molecular library containing the microprotein in the amino acid sequences was shown to comprise a larger number of clones having high binding affinity than that of a library comprising flexible amino acid sequences having no particular structure.

Example 8

This Example shows a method and results of determining the conformation of a complex of the polypeptide p17_2 consisting of SEQ ID NO: 47 and a human IgG Fc region by X-ray crystallography.

The polypeptide p17_2 was prepared according to similar procedures as in the section 3) of Example 3. The human IgG Fc region was prepared according to similar procedures as in the section 1) of Example 2. A complex of the polypeptide p17_2 and the Fc region was dialyzed against a buffer solution (20 mM Tris-HCl, and 10% (v/v) dimethyl sulfoxide, pH 7.4) and enriched into a concentration of 10 mg/ml by ultrafiltration. The precipitant and buffer solution used for crystallization were 40% polyethylene glycol 4000, 0.1 M sodium citrate (pH 5.6), and 0.2 M ammonium acetate to obtain crystals by the sitting-drop vapor diffusion method. Diffraction data was collected by Photon Factory NW-12A (High Energy Accelerator Research Organization, KEK) using the obtained crystals. Phase determination was carried out by the molecular replacement method using a search model (Protein Data Bank (PDB) code, 1DN2). The structure was refined by CNS, ccp4i, coot (References 48 to 50) to determine the crystal structure of the complex at a resolution of 2.9 angstroms. Asymmetric units contained four complexes, i.e., four Fc regions and eight p17_2 molecules.

Figure 15:
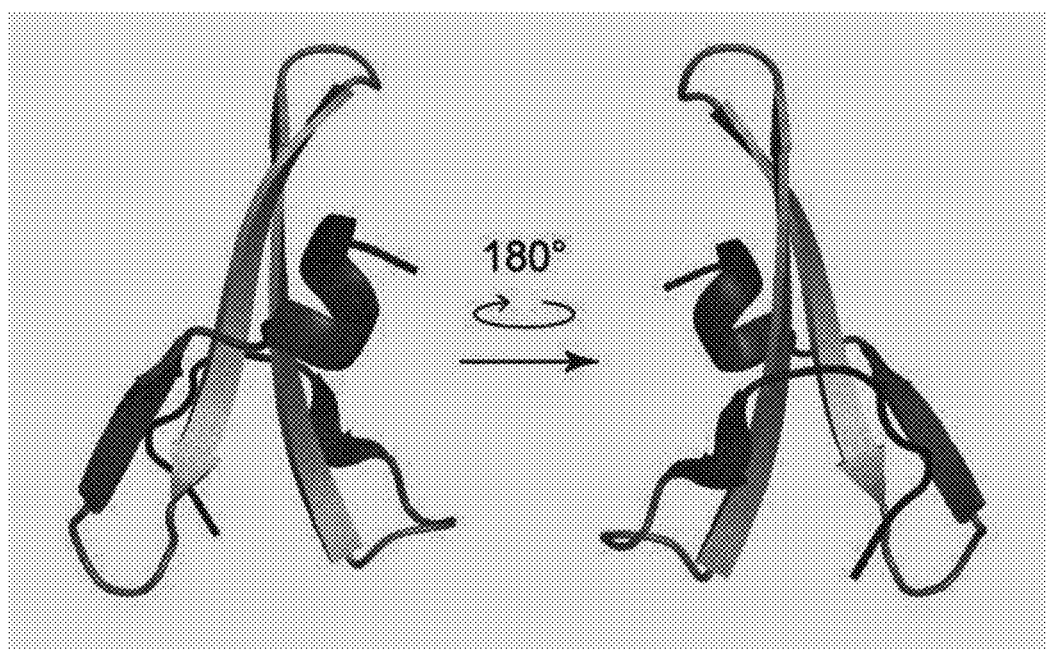
FIG. 15 shows the ribbon model of the whole structure of a polypeptide p17_2.
Figure 16:
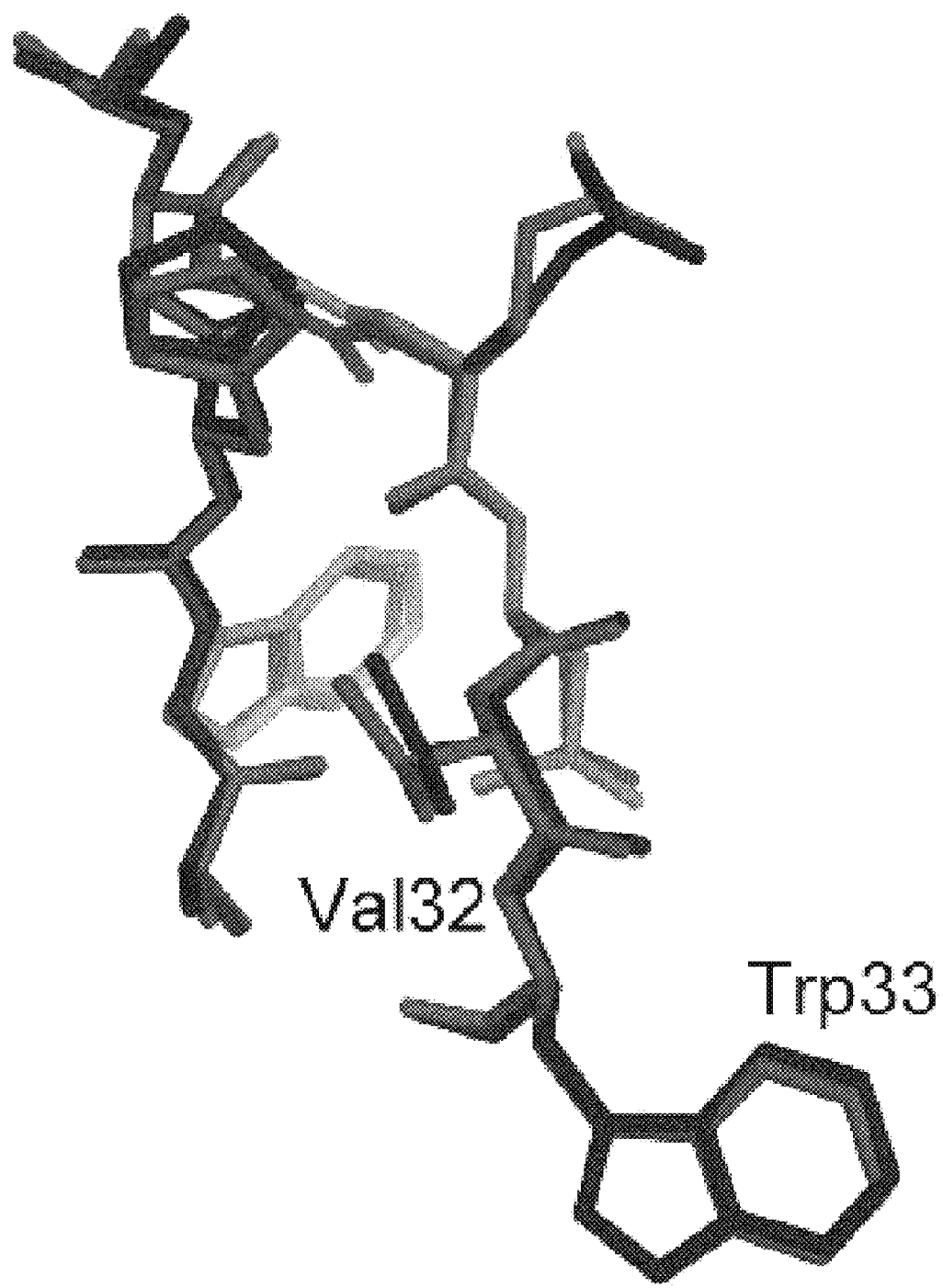
FIG. 16 shows the structural superposition of the polypeptide p17_2 and Fc III.
Figure 17:
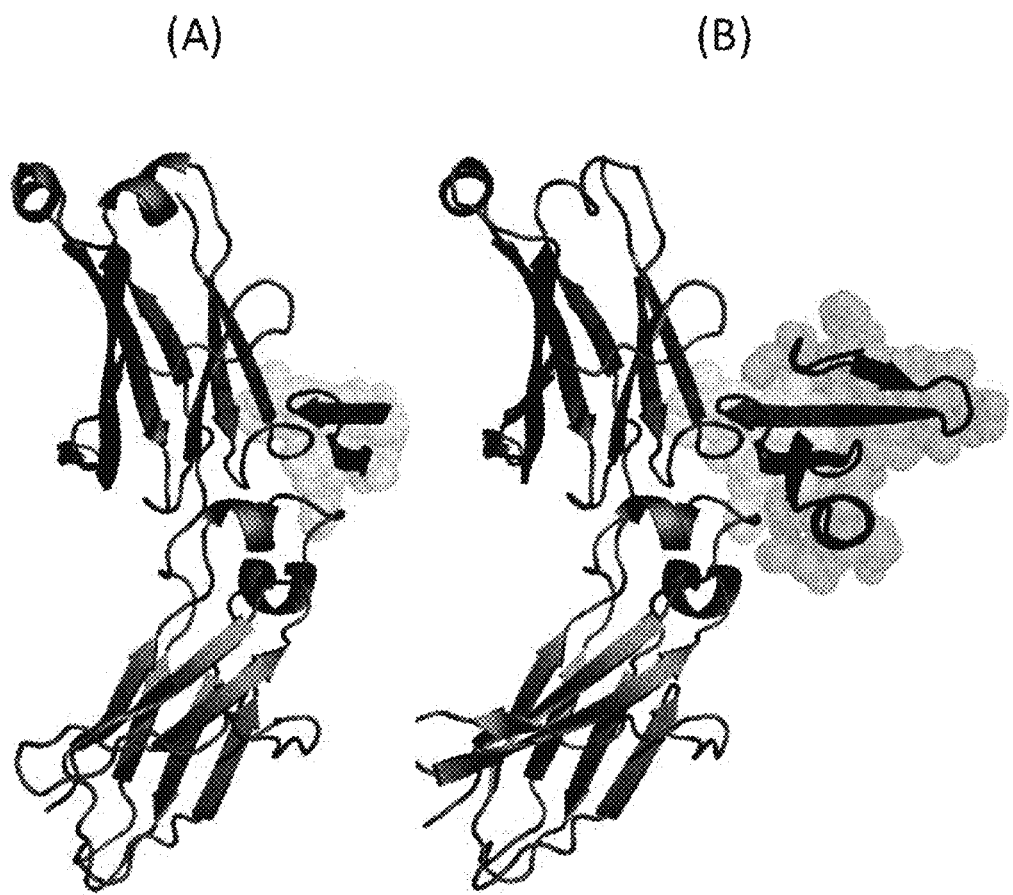
FIG. 17 shows the complex structure of Fc III and an Fc region (A) and the complex structure of the polypeptide p17_2 and an Fc region (B).
Figure 18:
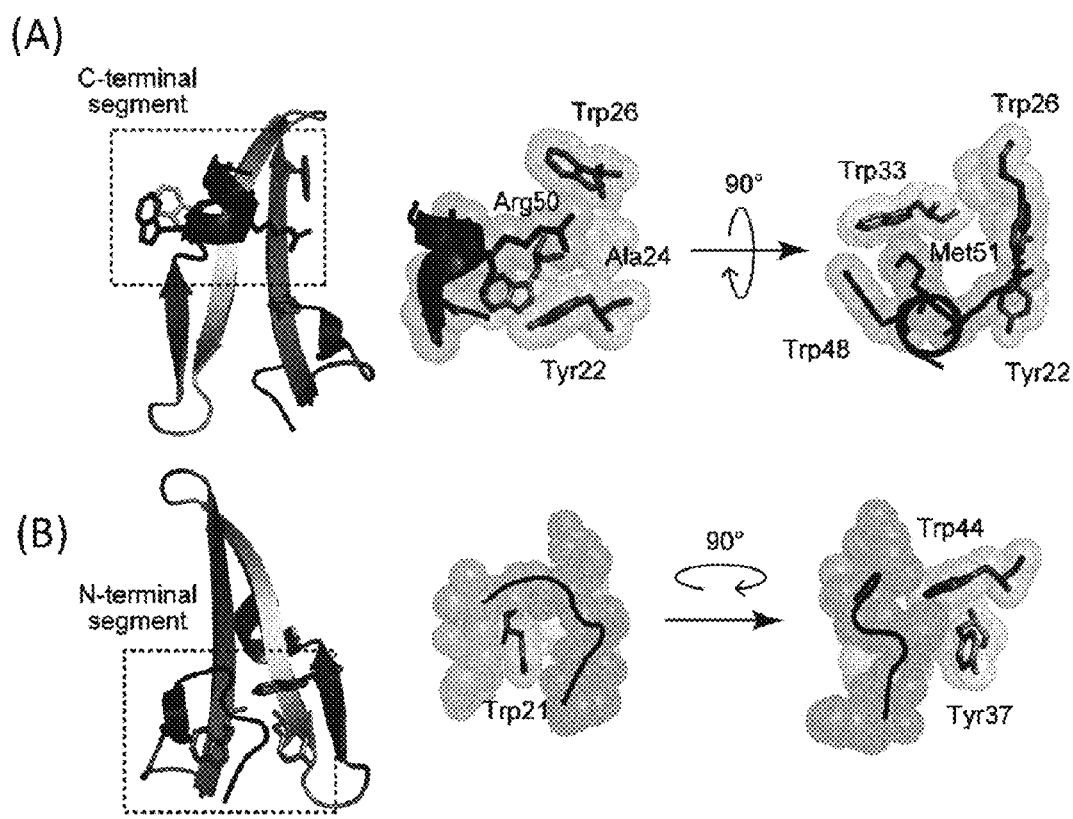
FIG. 18 shows α-helix formed by a C-terminal segment (A) and a loop structure formed by an N-terminal segment (B).

The polypeptide p17_2 was constituted by four β-strands, three β-hairpins, one short α-helix, and one loop structure (FIG. 15). The structure of the FcIII-Ala moiety contained in p17_2 exhibited high structural homology (r.m.s.d.=0.639 angstroms) to the conformation (PDB code, 1DN2) of the templated Fc III peptide in terms of both principal and side chains (FIG. 16), and its Fc region-binding site also recognized a position equivalent thereto (FIG. 17). This indicates that the high functionalization of a peptide according to the present invention can enhance the properties of the original functions without impairing these properties. The chignolin-derived region introduced in the library formed β-hairpin as with chignolin and was responsible for positioning regions elongated as random amino acid sequences to the neighborhood of FcIII-Ala. This indicates that use of the microprotein forming β-hairpin is responsible for effectively locating two segments close to each other. Two regions elongated as random amino acid sequences formed totally different conformations. The C-terminal region formed short α-helix such that a side chain protruded from the helix surface was contacted with the amino acid residue of FcIII-Ala to support a conformation advantageous for binding (FIG. 18). The previous studies have suggested that the orientation of a Trp residue is important for the binding of the templated Fc III peptide to the Fc region (References 46 and 47). The corresponding aromatic ring residue Trp33 in FcIII-Ala was directly supported by the side chain of Met51 present in the α-helix (FIG. 18). In contrast to the C-terminal region, the N terminus formed a loop structure such that this structure was contacted with the introduced chignolin moiety, which corresponded to the scaffold of FcIII-Ala, to support this scaffold (FIG. 18). These results demonstrated that the segments introduced as random amino acid sequences form a conformation suitable for each situation as a result of function selection to achieve the high functionalization of the polypeptide.

Example 9

This Example shows an example in which variants were prepared by the replacement of an amino acid residue in the C-terminal segment of the p17_2 polypeptide (SEQ ID NO: 47) with alanine and assayed for their binding affinity to evaluate the influence of the amino acid residue on the binding affinity, while the obtained results were checked against the conformational information obtained in Example 8 to analyze in detail the roles of these amino acid residues.

DNAs (SEQ ID NOs: 65 to 69) encoding the amino acid sequences represented by SEQ ID NOs: 60 to 64, respectively, were designed and synthesized by PCR. According to similar procedures as in the section 3) of Example 3, thioredoxin fusion proteins were expressed and treated with protease to prepare variant polypeptides, which were designated as follows: p17_P46A (SEQ ID NO: 60), p17_D47A (SEQ ID NO: 61), p17_W48A (SEQ ID NO: 62), p17_R50A (SEQ ID NO: 63), and p17_M51A (SEQ ID NO: 64).

Subsequently, the prepared 5 types of polypeptides were analyzed for their binding affinity by surface plasmon resonance. The assay employed Biacore T100 (GE Healthcare Japan Corp.). The immobilization of the Fc region to a sensor chip CM5 (GE Healthcare Japan Corp.) and the binding affinity analysis were carried out according to similar procedures as in the section 2) of Example 2. The binding affinity of each polypeptide obtained as a result of the analysis is shown in Table 3. Reduction in binding affinity was confirmed in all of the variants resulting from the replacement with alanine, suggesting that these residues are involved in the binding affinity. Particularly, p17_W48A and p17_M51A caused 100-fold or more reduction in binding affinity as a result of the replacement with alanine.

TABLE 3

Table 3. Binding dissociation constant of p17_2 variant

| Variant | $K_D$ (nM) | SEQ ID NO |
|---|---|---|
| p17_P46A | 5.6 | 60 |
| p17_D47A | 45 | 61 |
| p17_W48A | 200 | 62 |
| p17_R50A | 7.8 | 63 |
| p17_M51A | 180 | 64 |

Figure 19:
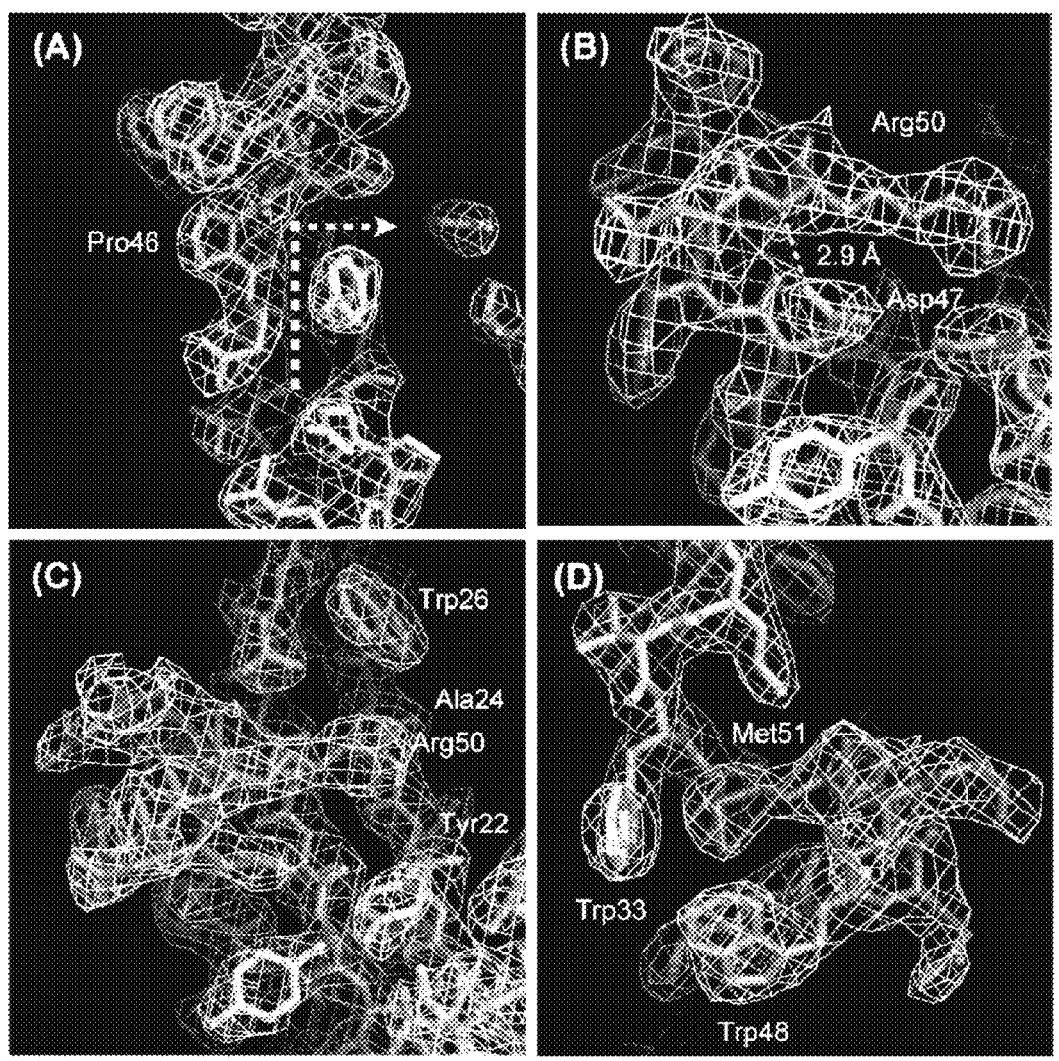
FIG. 19 shows an electron density map in the neighborhood of Pro46 (A), an electron density map in the neighborhood of Asp47 (B), an electron density map in the neighborhood of Arg50 (C), and an electron density map in the neighborhood of Trp48 and Met51 (D).

Subsequently, the alanine-replaced sites were investigated from a structural viewpoint. At the site Pro46, the direction of the principal chain of each polypeptide was shifted due to the structure orientation characteristic of proline residues. Thus, this site is responsible for fine adjustment to orient the following α-helix to an appropriate position (FIG. 19A). Asp47 is hydrogen-bonded to Arg50 in the vicinity thereof (FIG. 19B) and finely adjusts the orientation of the α-helix, as with Pro46. Arg50 present in the α-helix assisted, through the contact of its side chain with Ala24, in the cross-link between β-strands at positions 23 to 35 forming a binding site (FIG. 19C) Likewise, the hydrophobic residues Trp48 and Met51 present in the α-helix were contacted with each other with Met 51 as a center to directly stabilize the aromatic ring of Trp33 present in the binding site (FIG. 19D). The previous studies (References 46 and 47) have showed that the orientation of the aromatic ring side chain of this Trp33 largely influences the binding to the Fc region. The aforementioned binding affinity test revealed that the replacement of Met51 with alanine caused 100-fold or more reduction in binding affinity. These two facts imply that the involvement of Met51 in binding enhances binding affinity by supporting the aromatic ring of Trp33.

These results experimentally demonstrated, in terms of both binding function analysis and conformation analysis, that the random amino acid sequences introduced into the molecular library adopt functionally and structurally suitable amino acid residues as a result of function selection to effectively highly functionalize the polypeptide.

REFERENCE

Reference 43; Freund C, Ross A, Guth B, Pluckthun A and Holak T A. (1993) Characterization of the linker peptide of the single-chain Fv fragment of an antibody by NMR spectroscopy. FEBS Lett. 320 97-100.

Reference 44; Iwakura M and Nakamura T. (1998) Effects of the length of a glycine linker connecting the N- and C-termini of a circularly permuted dihydrofolate reductase. Protein Eng. 11(8) 707-713.

Reference 45; Guntert P, Mumenthaler C and Wuthrich K. (1997) Torsion angle dynamics for NMR structure calculation with the new program DYANA. J. Mol. Biol. 273, 283-298.

Reference 46; DeLano W L, Ultsch M H, de Vos A M and Wells J A. (2000) Convergent solutions to binding at a protein-protein interface. Science 287(5456) 1279-1283.

Reference 47; Dias R L, Fasan R, Moehle K, Renard A, Obrecht D and Robinson J A. (2006) Protein ligand design: from phage display to synthetic protein epitope mimetics in human antibody Fc-binding peptidomimetics. J Am Chem Soc. 2006 128(8) 2726-2732.

Reference 48; Brunger A T, Adams P D, Clore G M, DeLano W L, Gros P, Grosse-Kunstleve R W, Jiang J S, Kuszewski J, Nilges M, Pannu N S, Read R J, Rice L M, Simonson T, and Warren G L. (1998) Crystallography &

NMR system: A new software suite for macromolecular structure determination. Acta Crystallogr D Biol Crystallogr. 54, 905-921), CCP4 suite Reference 49; Winn M D, Ballard C C, Cowtan K D, Dodson E J, Emsley P, Evans P R, Keegan R M, Krissinel E B, Leslie A G, McCoy A, McNicholas S J, Murshudov G N, Pannu N S, Potterton E A, Powell H R, Read R J, Vagin A and Wilson K S. (2011) Overview of the CCP4 suite and current developments. Acta Crystallogr D Biol Crystallogr. 67, 235-242), Coot Reference 50; Emsley P and Cowtan K. (2004) Coot: model-building tools for molecular graphics. Acta Crystallogr D Biol Crystallogr. 60, 2126-2132.

All publications, patents, and patent applications cited herein are incorporated herein by reference in their entirety.

INDUSTRIAL APPLICABILITY

In recent years, the evolutionary molecular engineering has been widely used as basic technology for the development of biopharmaceutical products and diagnostic testing drugs. The present invention can provide a novel functional molecule having a small molecular weight, a novel small protein, or a novel noncyclic oligopeptide as a candidate of these pharmaceutical products, etc. The smaller-size molecule exhibits superiority in improvement in tissue infiltration or immunogenicity during administration to human bodies, reduction in production cost required for large-scale synthesis, improvement in storage stability, etc. The conformation formation of such a molecule, albeit having a low molecular weight, is driven by the spontaneous folding of the microprotein incorporated therein and therefore results in stable conformation without the need of chemical cross-link and introduction of a functional group necessary therefor. This can achieve high affinity and high selectivity, which cannot be provided by short-chain peptide libraries. These points are also beneficial to fields other than the pharmaceutical field, for example, research reagents or biosensors. Thus, the present invention is largely industrially applicable.

FREE TEXT OF SEQUENCE LISTING

SEQ ID NO: 1: Chignolin
SEQ ID NO: 2: Chignolin variant
SEQ ID NO: 3: Chignolin variant
SEQ ID NO: 4: Chignolin variant
SEQ ID NO: 5: Chignolin variant
SEQ ID NO: 6: Chignolin library
SEQ ID NO: 7: Chignolin library gene
SEQ ID NO: 8: Selected sequence
SEQ ID NO: 9: Chignolin library
SEQ ID NO: 10: Chignolin library gene
SEQ ID NO: 11: Oligo DNA
SEQ ID NO: 12: Oligo DNA
SEQ ID NO: 13: Selected sequence, 2A1
SEQ ID NO: 14: Control peptide, 2A1Gly
SEQ ID NO: 15: Chignolin library
SEQ ID NO: 16: Chignolin library gene
SEQ ID NO: 17: Oligo DNA
SEQ ID NO: 18: Oligo DNA
SEQ ID NO: 19: Selected sequence
SEQ ID NO: 20: Selected sequence
SEQ ID NO: 21: Selected sequence
SEQ ID NO: 22: Selected sequence
SEQ ID NO: 23: Chignolin library
SEQ ID NO: 24: Chignolin library
SEQ ID NO: 25: Chignolin library
SEQ ID NO: 26: Chignolin library
SEQ ID NO: 27: Chignolin library gene
SEQ ID NO: 28: Chignolin library gene
SEQ ID NO: 29: Chignolin library gene
SEQ ID NO: 30: Chignolin library gene
SEQ ID NO: 31: Oligo DNA
SEQ ID NO: 32: Oligo DNA
SEQ ID NO: 33: Oligo DNA
SEQ ID NO: 34: Oligo DNA
SEQ ID NO: 35: Oligo DNA
SEQ ID NO: 36: Oligo DNA
SEQ ID NO: 37: Selected sequence
SEQ ID NO: 38: Selected sequence
SEQ ID NO: 39: Selected sequence
SEQ ID NO: 40: Selected sequence, p17
SEQ ID NO: 41: Selected sequence
SEQ ID NO: 42: Selected sequence
SEQ ID NO: 43: Selected sequence
SEQ ID NO: 44: Selected sequence
SEQ ID NO: 45: Selected sequence
SEQ ID NO: 46: Oligo DNA
SEQ ID NO: 47: Selected sequence, p17_2
SEQ ID NO: 48: Trp-cage protein
SEQ ID NO: 49: FSD-1
SEQ ID NO: 50: Lanthanide-binding peptide
SEQ ID NO: 51: Selected sequence, 2A1_Q5R
SEQ ID NO: 52: Selected sequence, 2A1_W6A
SEQ ID NO: 53: Selected sequence, 2A1_S7A
SEQ ID NO: 54: Selected sequence, 2A1_R17A
SEQ ID NO: 55: Selected sequence, 2A1_S18A
SEQ ID NO: 56: Selected sequence, 2A1_S19A
SEQ ID NO: 57: Selected sequence, 2A1_I20A
SEQ ID NO: 58: Glycine library
SEQ ID NO: 59: Glycine library gene
SEQ ID NO: 60: Selected sequence, p17_P46A
SEQ ID NO: 61: Selected sequence, p17_D47A
SEQ ID NO: 62: Selected sequence, p17_W48A
SEQ ID NO: 63: Selected sequence, p17_R50A
SEQ ID NO: 64: Selected sequence, p17_M51A
SEQ ID NO: 65: Oligo DNA
SEQ ID NO: 66: Oligo DNA
SEQ ID NO: 67: Oligo DNA
SEQ ID NO: 68: Oligo DNA
SEQ ID NO: 69: Oligo DNA

The invention claimed is:

1. A molecular library comprising a group of a plurality of molecules, wherein each member of the library is a polypeptide having a randomized sequence moiety and a microprotein moiety, and
   wherein each member of the library is a polypeptide molecule comprising the following amino acid sequence:
   -[(Xaa)$_n$-Tyr-Asp-Pro-Xaa-Thr-Gly-Thr-Trp-(Xaa)$_m$]$_k$-
   wherein Xaa represents an arbitrary amino acid residue, k represents an integer of 2 or larger, each n independently represents an integer of 0 or larger, and each m independently represents an integer of 0 or larger.

2. The molecular library according to claim 1, wherein each member of the library further comprises a fixed sequence moiety.

3. The library according to claim 2, wherein the fixed sequence moiety comprises a whole or partial amino acid sequence of a known polypeptide, or a whole or partial amino acid sequence of a polypeptide selected from the molecular library according to claim 1.

4. The molecular library according to claim 1, wherein the polypeptide as each member of the library is present in a form associated with a polynucleotide encoding this polypeptide.

5. The molecular library according to claim 4, wherein the polypeptide as each member of the library is linked to the polynucleotide encoding this polypeptide.

6. The molecular library according to claim 4, wherein the polypeptide as each member of the library is displayed on the surface layer of a bacteriophage, and the polynucleotide encoding this polypeptide is incorporated in the bacteriophage.

7. A polynucleotide library comprising a group of polynucleotides encoding members of the molecular library according to claim 1.

8. A method for identifying a polypeptide molecule capable of binding to a target substance, comprising the following steps (a) to (c):
   (a) contacting a library according to claim 2 with the target substance;
   (b) selecting a member binding to the target substance from the library; and
   (c) determining the amino acid sequence of the selected member.

9. The method according to claim 8, wherein the determination of the amino acid sequence is carried out by the sequencing of the polynucleotide associated with the polypeptide.

10. The method according to claim 8, wherein the target substance is a human immunoglobulin.

* * * * *